United States Patent
Masukawa et al.

(10) Patent No.: US 7,842,357 B2
(45) Date of Patent: Nov. 30, 2010

(54) TETRAHYDROPYRAN COMPOUND, LIQUID CRYSTAL, COMPOSITION AND LIQUID CRYSTAL DISPLAY DEVICE CONTAINING THE LIQUID CRYSTAL COMPOSITION

(75) Inventors: Tokifumi Masukawa, Ichihara (JP); Atsuko Fujita, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 929 days.

(21) Appl. No.: 11/244,243

(22) Filed: Oct. 4, 2005

(65) Prior Publication Data

US 2006/0071194 A1 Apr. 6, 2006

(30) Foreign Application Priority Data

Oct. 4, 2004 (JP) ............................ 2004-291570

(51) Int. Cl.
C09K 19/34 (2006.01)
C09K 19/30 (2006.01)
C07D 309/02 (2006.01)
C07D 309/04 (2006.01)

(52) U.S. Cl. .............. 428/1.1; 252/299.61; 252/299.63; 549/356; 549/427; 549/428

(58) Field of Classification Search ............ 252/299.61, 252/299.63; 549/356, 427, 428; 428/1.1
See application file for complete search history.

(56) References Cited

U.S. PATENT DOCUMENTS

| 4,818,431 | A | 4/1989 | Eidenschink et al. ... | 252/299.61 |
|---|---|---|---|---|
| 6,329,027 | B1 * | 12/2001 | Kondo et al. ............... | 428/1.1 |
| 6,395,353 | B2 * | 5/2002 | Yanai et al. ............... | 428/1.1 |
| 6,558,758 | B1 | 5/2003 | Yanai et al. ............... | 428/1.1 |
| 6,649,227 | B2 * | 11/2003 | Kato et al. ............... | 428/1.1 |
| 2001/0038091 | A1 | 11/2001 | Yanai et al. ............ | 252/299.63 |
| 2002/0015804 | A1 | 2/2002 | Haseba et al. ............... | 428/1.1 |
| 2002/0030179 | A1 | 3/2002 | Miyazawa et al. ..... | 252/299.01 |
| 2004/0140452 | A1 * | 7/2004 | Hirschmann et al. ... | 252/299.61 |

FOREIGN PATENT DOCUMENTS

| DE | 4132006 | 4/1993 |
|---|---|---|
| DE | 4222371 | 1/1994 |
| DE | 4238377 | 5/1994 |
| DE | 19611096 | 9/1997 |
| DE | 19625100 | 1/1998 |
| DE | 19733199 | 2/1999 |
| DE | 19950194 | 5/2000 |
| EP | 0376294 | 7/1990 |
| EP | 0630892 | 11/1999 |
| EP | 0967261 | 12/1999 |
| EP | 0982388 | 3/2000 |
| EP | 1302523 | 4/2003 |
| GB | 2310669 | 9/1997 |
| JP | 10-236989 | 9/1998 |
| JP | 10-237000 | 9/1998 |
| WO | WO 91/05029 | 4/1991 |
| WO | WO 92/13928 | 8/1992 |
| WO | WO 96/23851 | 8/1996 |

OTHER PUBLICATIONS

Leticia Ayaia et al, "Stereochemistry of Nucleophilic Substitution Reactioins Depending upon Substituent: Evience for Electrostatic Stabilization of Pseudoxial Conformers of Oxocarbenium Ions by Heteroatom Substituents" American Chemical Society, vol. 125, No. 50, Nov. 21, 2003, pp. 15521-15528.

Jan Antoinette C. Romero, et al, "Ssterechemical Reversal of Nucleophilic Substitution Reactions depending upon Substituent: Reactions of Heteroatom-Substituted Six-Membered-Ring Oxocarbenium ions through Pseudoaxial Conformers" American Chemical Society, vol. 122, No. 1, 2000, pp. 168-169.

Igor Tvaroska et al, "One-bond carbon-proton coupling constants: angular dependence in α-linked oligosaccharides" Carbohydrate Research, vol. 221, 1991-Elsevier Science Publishers B.V., pp. 83-94.

\* cited by examiner

*Primary Examiner*—Shean C Wu
(74) *Attorney, Agent, or Firm*—J.C. Patents

(57) ABSTRACT

A compound represented by the following formula (1):

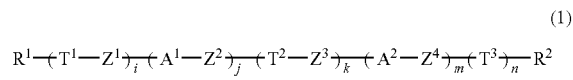

wherein $R^1$ and $R^2$ are, for example alkyl; $T^1$, $T^2$ and $T^3$ are independently tetrahydropyran-2,5-diyl or tetrahydropyran-3,6-diyl; $A^1$ and $A^2$ are, for example 1,4-cyclohexylene; $Z^1$, $Z^2$, $Z^3$ and $Z^4$ are, for example, a single bond; i, j, k, m and n are, for example 0 or 1; and i+j+k+m+n is, for example 2 or 3.

26 Claims, No Drawings

TETRAHYDROPYRAN COMPOUND, LIQUID CRYSTAL, COMPOSITION AND LIQUID CRYSTAL DISPLAY DEVICE CONTAINING THE LIQUID CRYSTAL COMPOSITION

BACKGROUND OF THE INVENTION

1. Field of the Invention

The present invention relates to a liquid crystal composition, a liquid crystal compound and a liquid crystal display device and more in particular, it relates to a tetrahydropyran compound, a liquid crystal composition containing the same and having a nematic phase and a liquid crystal display device containing the liquid crystal composition.

2. Related Art

A liquid crystal display device utilizes optical anisotropy and dielectric anisotropy inherent to a liquid crystal substance. The liquid crystal display device is classified into various types including a TN type (twisted nematic type), a DS type (dynamic scattering type), a guest-host type, a DAP type (deformation of aligned phase type), an STN type (super twisted nematic type) and a TFT type (thin film transistor type), and the TN type, the STN type and the TFT type are becoming mainstream in recent years. It is necessary that a liquid crystal material used in any of these types of display devices has stability to water, air, heat and light, and also it exhibits a liquid crystal phase in a wide temperature range as much as possible centering on room temperature, has a low viscosity, has an optimum dielectric anisotropy value ($\Delta\in$), and has an optimum refractive index anisotropy value ($\Delta n$), an optimum elastic constant K and an optimum elastic constant ratio $K_{33}/K_{11}$ ($K_{33}$: bend elastic constant, $K_{11}$: splay elastic constant). It is the current situation that there is no single substance that satisfies these requirements, and several to several dozen kinds of liquid crystal substances are mixed to fulfill the aforementioned required characteristics. Upon preparing a liquid crystal composition, there are some cases where the required characteristics cannot be fulfilled due to a too small $\Delta\in$ and a too large $\Delta n$, for example.

The requirements to the characteristics of the liquid crystal composition are currently becoming severe for attaining a liquid crystal display device having high performance. In order to satisfy the requirements, such a liquid crystal compound is demanded that can highly adjust the properties of the liquid crystal composition.

It is currently demanded that a liquid crystal display can be driven at a low temperature. In general, compounds used in a composition having a low $\Delta n$ contain a large amount of cyclohexane rings, and a smectic phase or crystals are liable to deposit from the composition due to the poor compatibility of the composition at a low temperature. Under the circumstances, development of a liquid crystal compound having a small $\Delta\in$ and a high clear point or a liquid crystal compound having a small $\Delta\in$ and being excellent in compatibility is demanded.

As a liquid crystal compound that are used in the aforementioned purposes, a compound represented by the following formula (16) has been reported in German Patent No. 3,306,960, for example. However, the compound (16) has a large $\Delta n$ and an insufficient compatibility at a low temperature.

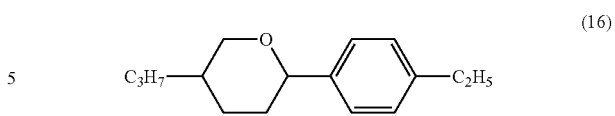

(16)

The related art of the invention is disclosed in the following patent documents: EP 1 302 523, DE 19 950 194, DE 19 733 199, DE 19 625 100, GB 2 310 669, DE 19 611 096, WO 9 632 851, DE 4 238 377, DE 4 222 371, WO 9 213 928, DE 4 132 006, WO 9 105 029 and EP 376 294. Further preferred liquid crystal compound, liquid crystal composition and liquid crystal display device are demanded.

SUMMARY OF THE INVENTION

The invention concerns a compound represented by the following formula (1):

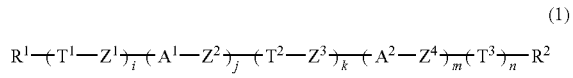

(1)

wherein $R^1$ and $R^2$ each independently represents hydrogen or alkyl having from 1 to 10 carbons, provided that in the alkyl arbitrary —$CH_2$— may be replaced by —O—, —S—, —CO— or —$SiH_2$—, and arbitrary —$(CH_2)_2$— may be replaced by —CH=CH— or —C≡C—; $T^1$, $T^2$ and $T^3$ each independently represents tetrahydropyran-2,5-diyl or tetrahydropyran-3,6-diyl; $A^1$ and $A^2$ each independently represents 1,4-cyclohexylene, 1,4-phenylene, decahydronaphthalene-2,6-diyl, 1,2,3,4-tetrahydronaphthalene-2,6-diyl or naphthalene-2,6-diyl, provided that in these rings one of —$CH_2$— may be replaced by —O—, —S—, —CO— or —$SiH_2$—, and arbitrary —$(CH_2)_2$— may be replaced by —CH=CH—, and in the 1,4-phenylene one of —CH=may be replaced by —N=; $Z^1$, $Z^2$, $Z^3$ and $Z^4$ each independently represents a single bond or alkylene having from 1 to 4 carbons, provided that in the alkylene arbitrary —$CH_2$— may be replaced by —O—, —S—, —CO— or —$SiH_2$—, and arbitrary —$(CH_2)_2$— may be replaced by —CH=CH— or i represents 0 to 1; j, k and m each independently represents 0, 1 or 2; n and b each independently represents 0 or 1; i+j+k+m+n is 2, 3 or 4; i+k+n is 1, 2, 3 or 4; when i+j+k+m+n is 2 or 3, j, k and m each independently represents 0 or 1; when i+j+k+m+n is 4, j+m is 3 and n is 1, j represents 1; when i represents 0, j represents 1 or 2; when n is 0, m represents 1 or 2; when i is 1, $R^1$ represents alkyl having from 1 to 10 carbons, provided that in the alkyl arbitrary —$CH_2$— may be replaced by —O—, —S—, —CO— or —$SiH_2$—, and arbitrary —$(CH_2)_2$— may be replaced by —CH=CH— or —C≡C—;

when n is 0, $Z^4$ represents a single bond; when i+k+n is 1, $T^1$, $T^2$ and $T^3$ each independently represents tetrahydropyran-2,5-diyl; when i+j+k+m+n is 2, $A^1$ and $A^2$ each independently represents 1,4-cyclohexylene or decahydronaphthalene-2,6-diyl, provided that in these rings one of —$CH_2$— may be replaced by —O—, —S—, —CO— or —$SiH_2$—; when i+j+k+m+n is 3, at least one of independent $A^1$ and $A^2$ represents 1,4-cyclohexylene or decahydronaphthalene-2,6-diyl, provided that in these rings one of —$CH_2$— may be replaced by —O—, —S—, —CO— or —$SiH_2$—; when i+j+k+m+n is 4, at least two of independent $A^1$ and $A^2$ each represents 1,4- cyclohexylene or decahydronaphthalene-2,6-diyl, provided that in these rings one of —$CH_2$— may be replaced by —O—, —S—, —CO— or —$SiH_2$—; and when i+j+k+m+n is 3, i+k is 0, $A^1$ is 1,4-cyclohexylene and $A^2$ is 1,4-phenylene, at least one of $R^1$ and $R^2$ represents alkenyl.

The invention also concerns a liquid crystal composition comprising of the compounds.

The invention also concerns a liquid crystal display device comprising the liquid crystal composition, the use of the composition, and so forth.

DETAILED DESCRIPTION

The terms used in the specification are defined as follows. A liquid crystal composition is a general term for a compound having a liquid crystal phase, such as a nematic phase and a smectic phase, and a compound having no liquid crystal phase but being useful as a component of the liquid crystal composition. The liquid crystal compound, the liquid crystal composition and the liquid crystal display device may occasionally be abbreviated as a compound, a composition and a device, respectively. A liquid crystal display device is a general term for a liquid crystal display panel and a liquid crystal display module. The higher limit temperature of a nematic phase is a phase transition temperature of from the nematic phase to the isotropic phase and may be occasionally abbreviated as a higher limit temperature. The lower limit temperature of a nematic phase may be occasionally abbreviated as a lower limit temperature. At least one compound selected from a group of compounds represented by the formula (1) may be occasionally abbreviated as a compound (1). The compounds represented by any other formula, such as the formula (2), may also be occasionally abbreviated in the same manner. In the formulae (1) to (11), the symbols $A^1$, $B^1$, E, M and the like correspond to the ring $A^1$, ring $B^1$, ring E, ring M and the like. The proportions (in terms of percentage) of the components or the liquid crystal compounds are in terms of percentage by weight (% by weight) based on the total weight of the liquid crystal composition. The invention will be described in detail below.

A first object of the invention is to provide such a liquid crystal composition that has a wide temperature range of a nematic phase, a small viscosity, a suitable optical anisotropy and a low threshold voltage. A second object of the invention is to provide such a liquid crystal composition that has properties that are ordinary to the compound, a small viscosity, a suitable optical anisotropy, a suitable dielectric anisotropy, and also has good compatibility with another liquid crystal compound. A third object of the invention is to provide such a liquid crystal display device that contains a composition containing the liquid crystal compound, and has a short response time, a small electric power consumption, a large contrast and a high voltage holding ratio.

The invention includes the liquid crystal compound represented by the formula (1), the liquid crystal composition and the liquid crystal display device shown below. Preferred examples of the end groups and the bonding groups in the formula (1) will also be described.

1. The invention relates to a compound represented by the following formula (1):

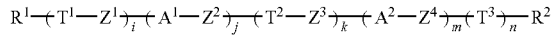

(1)

wherein $R^1$ and $R^2$ are independently hydrogen or alkyl having from 1 to 10 carbons, provided that in the alkyl arbitrary —$CH_2$— may be replaced by —O—, —S—, —CO— or —$SiH_2$—, and arbitrary —$(CH_2)_2$— may be replaced by —CH=CH— or —C≡C—; $T^1$, $T^2$ and $T^3$ are independently tetrahydropyran-2,5-diyl or tetrahydropyran-3,6-diyl; $A^1$ and $A^2$ are independently 1,4-cyclohexylene, 1,4-phenylene, decahydronaphthalene-2,6-diyl, 1,2,3,4-tetrahydronaphthalene-2,6-diyl or naphthalene-2,6-diyl, provided that in these rings one of —$CH_2$— may be replaced by —O—, —S—, —CO— or —$SiH_2$—, and arbitrary —$(CH_2)_2$— may be replaced by —CH=CH—, and in the 1,4-phenylene one of —CH= may be replaced by —N=; $Z^1$, $Z^2$, $Z^3$ and $Z^4$ are independently a single bond or alkylene having from 1 to 4 carbons, provided that in the alkylene arbitrary —$CH_2$— may be replaced by —O—, —S—, —CO— or —$SiH_2$—, and arbitrary —$(CH_2)_2$— may be replaced by —CH=CH— or —C≡C—; i is 0 to 1; j, k and m are independently 0, 1 or 2; n is 0 or 1; i+j+k+m+n is 2, 3 or 4; i+k+n is 1, 2, 3 or 4; when i+j+k+m+n is 2 or 3, j, k and m are independently 0 or 1; when i+j+k+m+n is 4, j+m is 3 and n is 1, j is 1; when i represents 0, j is 1 or 2; when n is 0, m is 1 or 2; when i is 1, $R^1$ is alkyl having from 1 to 10 carbons, provided that in the alkyl arbitrary —$CH_2$— may be replaced by —O—, —S—, —CO— or —$SiH_2$—, and arbitrary —$(CH_2)_2$— may be replaced by —CH=CH— or —C≡C—; when n is 0, $Z^4$ is a single bond; when i+k+n is 1, $T^1$, $T^2$ and $T^3$ are independently tetrahydropyran-2,5-diyl; when i+j+k+m+n is 2, $A^1$ and $A^2$ are independently 1,4-cyclohexylene or decahydronaphthalene-2,6-diyl, provided that in these rings one of —$CH_2$— may be replaced by —O—, —S—, —CO— or —$SiH_2$—; when i+j+k+m+n is 3, at least one of $A^1$ and $A^2$ is 1,4-cyclohexylene or decahydronaphthalene-2,6-diyl, provided that in these rings one of —$CH_2$— may be replaced by —O—, —S—, —CO— or —$SiH_2$—; when i+j+k+m+n is 4, at least two of $A^1$ and $A^2$ each is 1,4-cyclohexylene or decahydronaphthalene-2,6-diyl, provided that in these rings one of —$CH_2$— may be replaced by —O—, —S—, —CO— or —$SiH_2$—; and when i+j+k+m+n is 3, i+k is 0, $A^1$ is 1,4-cyclohexylene and $A^2$ is 1,4-phenylene, at least one of $R^1$ and $R^2$ is alkenyl.

An example of the meaning expressed by the phrase "in the alkyl arbitrary —$CH_2$— may be replaced by —O—, —S—, —CO— or —$SiH_2$—, and arbitrary —$(CH_2)_2$— may be replaced by —CH=CH— or —C≡C—" will be described. Examples of the group obtained from $C_4H_9$— by substituting arbitrary —$CH_2$— therein by —O— and substituting arbitrary —$(CH_2)_2$— therein by —CH=CH— include $C_3H_7O$—, $CH_3$—O—$(CH_2)_2$—$CH_3$—O—$CH_2$—O—, $H_2C$=CH$(CH_2)_2$—, $CH_3$—CH=CH—$CH_2$— and $CH_2$=CH—$CH_2$—O—. Accordingly, the term "arbitrary" means "one that is selected with no distinction". Taking the stability of the compound into consideration, $CH_3$—O—$CH_2$—O— where two oxygen atoms are not adjacent to each other is preferred than $CH_3$—O—O—$CH_2$— where two oxygen atoms are adjacent to each other.

Preferred examples of $R^1$ or $R^2$ include alkyl having from 2 to 10 carbons, alkenyl, alkoxy, alkoxyalkyl and alkenyloxy. Of these groups, a linear group is preferred than a branched group. A branched group is preferred as $R^1$ and $R^2$ when the branched group is optically active. More preferred examples of $R^1$ or $R^2$ include alkyl having from 2 to 10 carbons, alkenyl, alkoxy, alkoxyalkyl and alkenyloxy. Most preferred examples of $R^1$ or $R^2$ include alkyl having from 2 to 10 carbons, alkoxy and alkenyl.

A preferred steric configuration of —CH=CH— in alkenyl depends on the position of the double bond. A trans configuration is preferred for such alkenyl as 1-propenyl, 1-butenyl, 1-pentenyl, 1-hexenyl, 3-pentenyl and 3-hexenyl. A cis configuration is preferred for such alkenyl as 2-butenyl, 2-pentenyl and 2-hexenyl.

Specific examples of $R^1$ or $R^2$ include methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy and 2-pentenyloxy.

More preferred examples of $R^1$ or $R^2$ include ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy and 2-pentenyloxy. Most preferred examples of $R^1$ or $R^2$ include ethyl, propyl, butyl, pentyl, hexyl, heptyl, octyl, methoxy, ethoxy, propoxy, butoxy, pentyloxy, hexyloxy, heptyloxy, vinyl, 1-propenyl, 2-propenyl, 1-butenyl, 2-butenyl, 3-butenyl, 1-pentenyl, 2-pentenyl, 3-pentenyl and 4-pentenyl.

$A^1$ and $A^2$ are independently 1,4-cyclohexylene, 1,4-phenylene, decahydronaphthalene-2,6-diyl, 1,2,3,4-tetrahydronaphthalene-2,6-diyl or naphthalene-2,6-diyl, provided that in these rings one of —CH$_2$— may be replaced by —O—, —S—, —CO— or —SiH$_2$—, and arbitrary —(CH$_2$)$_2$— may be replaced by —CH=CH—, and in the 1,4-phenylene one of —CH= may be replaced by N=.

Preferred examples of $A^1$ and $A^2$ include 1,4-cyclohexylene, 1,4-phenylene, decahydronaphthalene-2,6-diyl, 1,2,3,4-tetrahydronaphthalene-2,6-diyl and naphthalene-2,6-diyl. More preferred examples of $A^1$ and $A^2$ include 1,4-cyclohexylene and 1,4-phenylene.

$Z^1$, $Z^2$, $Z^3$ and $Z^4$ are independently a single bond or alkylene having from 1 to 4 carbons, provided that in the alkylene arbitrary —CH$_2$— may be replaced by —O—, —S—, —CO— or —SiH$_2$—, and arbitrary —(CH$_2$)$_2$— may be replaced by —CH=CH—, —C≡C—, —CO— or —SiH$_2$—.

Preferred examples of $Z^1$, $Z^2$, $Z^3$ and $Z^4$ include a single bond, —(CH$_2$)$_2$—, —CH=CH—, —CH$_2$O—, —OCH$_2$—, —(CH$_2$)$_4$—, —C≡C—, —COO—, —OCO—, —CH$_2$CO—, —COCH$_2$—, —CH$_2$SiH$_2$—, —SiH$_2$CH$_2$—, —O(CH$_2$)$_2$O—, —(CH$_2$)$_2$COO—, —(CH$_2$)$_2$OCO—, —COO(CH$_2$)$_2$—, —OCO(CH$_2$)$_2$—, —CH=CH—CH$_2$O— and —OCH$_2$—CH=CH—. The steric configuration of the double bond in such a bonding group as —CH=CH—, —CH=CH—CH$_2$O— and —OCH$_2$—CH=CH— is preferably trans configuration rather than cis configuration.

More preferred examples of $Z^1$, $Z^2$, $Z^3$ and $Z^4$ include a single bond, —(CH$_2$)$_2$—, —CH=CH—, —CH$_2$O—, —OCH$_2$—, —(CH$_2$)$_4$— and —C≡C—. Most preferred examples of $Z^1$, $Z^2$, $Z^3$ and $Z^4$ include a single bond, —(CH$_2$)$_2$— and —CH=CH—.

The compound of the invention, for example, has ordinary properties that are necessary for the compound, stability to heat and light, a suitable optical anisotropy, a suitable dielectric anisotropy and good compatibility with another liquid crystal compound. The liquid crystal composition of the invention, for example, contains at least one of the compound and has a high higher limit temperature of a nematic phase, a low lower limit temperature of a nematic phase, a small viscosity, a suitable optical anisotropy and a low threshold voltage. The liquid crystal display device of the invention contains the composition and has a wide usable temperature range, a short response time, a large contrast ratio and a low driving voltage.

2. The compound according to item 1, wherein the compound is represented by one of the following formulae (1-1), (1-2), (1-4) to (1-6) and (1-11) to (1-14):

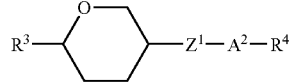

(1-1)

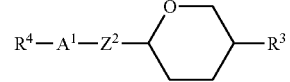

(1-2)

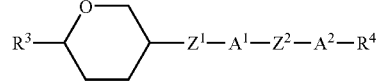

(1-4)

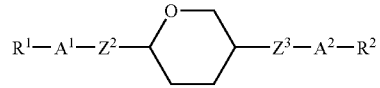

(1-5)

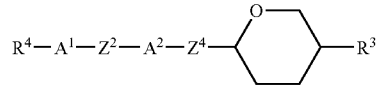

(1-6)

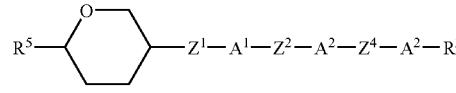

(1-11)

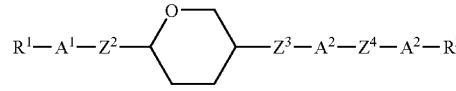

(1-12)

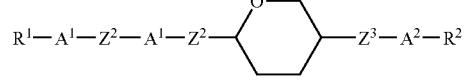

(1-13)

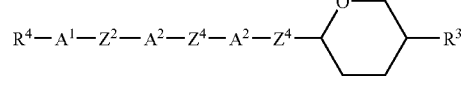

(1-14)

wherein $R^1$, $R^2$ and $R^4$ are independently hydrogen or alkyl having from 1 to 10 carbons, provided that in the alkyl arbitrary —CH$_2$— may be replaced by —O—, —S—, —CO— or —SiH$_2$—, and arbitrary —(CH$_2$)$_2$— may be replaced by —CH=CH— or —C≡C—; $R^3$ and $R^5$ are independently alkyl having from 1 to 10 carbons, provided that in the alkyl arbitrary —CH$_2$— may be replaced by —O—, —S—, —CO— or —SiH$_2$—, and arbitrary —(CH$_2$)$_2$— may be replaced by —CH=CH— or —C≡C—; $A^1$ and $A^2$ are independently 1,4-cyclohexylene, 1,4-phenylene, decahydronaphthalene-2,6-diyl, 1,2,3,4-tetrahydronaphthalene-2,6-diyl or naphthalene-2,6-diyl, provided that in these rings one of —CH$_2$— may be replaced by —O—, —S—, —CO— or —SiH$_2$—, and arbitrary —(CH$_2$)$_2$— may be replaced by —CH=CH—, and in the 1,4-phenylene one of —CH= may be replaced by —N=; $Z^1$, $Z^2$, $Z^3$ and $Z^4$ are independently a single bond or alkylene having from 1 to 4 carbons, provided that in the alkylene arbitrary —CH$_2$— may be replaced by —O—, —S—, —CO— or —SiH₂—, and arbitrary —(CH₂)₂— may be replaced by —CH═CH— or —C≡C—; in the formula (1-6) when A¹ is 1,4-cyclohexylene and A² is 1,4-phenylene, at least one of R³ and R⁴ is alkenyl; in the formula (1-6) when A¹ and A² each is 1,4-phenylene, at least one of R³ and R⁴ is alkenyl; and in the formula (1-14) when A¹ is 1,4-cyclohexylene and A² is 1,4-phenylene, at least one of R³ and R⁴ is alkenyl.

3. The compound according to item 2, wherein in the formulae (1-1), (1-2), (1-4) to (1-6) and (1-11) to (1-14), R¹ to R⁵ are independently alkyl having from 2 to 10 carbons, alkenyl having from 2 to 10 carbons, alkoxy having from 1 to 9 carbons, alkoxyalkyl having from 2 to 9 carbons, alkenyloxy having from 3 to 9 carbons, polyfluoroalkyl having from 2 to 10 carbons A¹ and A² are independently 1,4-cyclohexylene, 1,4-phenylene, decahydronaphthalene-2,6-diyl, 1,2,3,4-tetrahydronaphthalene-2,6-diyl or naphthalene-2,6-diyl; and Z¹, Z², Z³ and Z⁴ are independently a single bond, —(CH₂)₂—, —CH═CH—, —CH₂O—, —OCH₂—, —(CH₂)₄—, —C≡C—, —COO—, —OCO—, —C≡C—, —CH₂CO—, —COCH₂—, —CH₂SiH₂—, —SiH₂CH₂—, —O(CH₂)₂O—, —(CH₂)₂COO—, —(CH₂)₂OCO—, —COO(CH₂)₂—, —OCO(CH₂)₂—, —CH═CH—CH₂O— or —OCH₂—CH═CH—.

4. The compound according to item 2, wherein in the formulae (1-1), (1-2), (1-4) to (1-6) and (1-11) to (1-14), R¹ to R⁵ are independently alkyl having from 2 to 10 carbons, alkenyl having from 2 to 10 carbons, alkoxy having from 1 to 9 carbons, alkoxyalkyl having from 2 to 9 carbons or alkenyloxy having from 3 to 9 carbons; A¹ and A² are independently 1,4-cyclohexylene or 1,4-phenylene; and Z¹, Z², Z³ and Z⁴ are independently a single bond, —(CH₂)₂—, —CH═CH—, —CH₂O—, —OCH₂—, —(CH₂)₄— or —C≡C—.

5. The compound according to item 2, wherein in the formulae (1-1), (1-2), (1-4) to (1-6) and (1-11) to (1-14), R¹ to R⁵ are independently alkyl having from 2 to 10 carbons, alkenyl having from 2 to 10 carbons or alkoxy having from 1 to 9 carbons; A¹ and A² are independently 1,4-cyclohexylene or 1,4-phenylne; and Z¹, Z², Z³ and Z⁴ are independently a single bond, —(CH₂)₂— or —CH═CH—.

6. The compound according to item 2, wherein in the formulae (1-1) and (1-2), A¹ and A² are 1,4-cyclohexylene; in the formulae (1-4) to (1-6), A¹ and A² are independently 1,4-cyclohexylene or 1,4-phenylene, and at least one of A¹ and A² is 1,4-cyclohexylene; and in the formulae (1-11) to (1-14), A¹ and A² are independently 1,4-cyclohexylene or 1,4-phenylene, and at least two of A¹ and A² are 1,4-cyclohexylene.

7. The compound according to any one of items 2 to 6, wherein the compound is represented by one of the following formulae (1-1-1), (1-2-1), (1-4-1) to (1-4-3), (1-5-1) to (1-5-3), (1-6-1) to (1-6-3), (1-11-1) to (1-11-4), (1-12-1) to (1-12-4), (1-13-1) to (1-13-4), and (1-14-1) to (1-14-4):

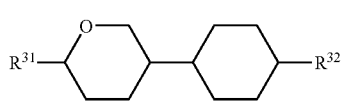

(1-1-1)

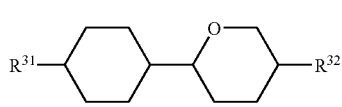

(1-2-1)

-continued

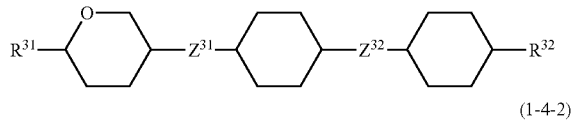

(1-4-1)

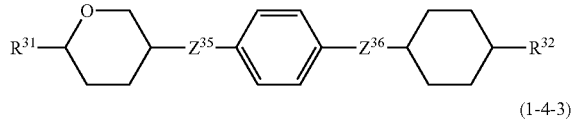

(1-4-2)

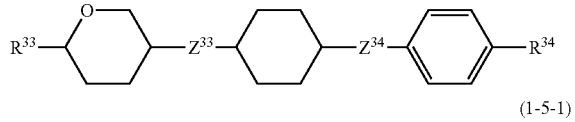

(1-4-3)

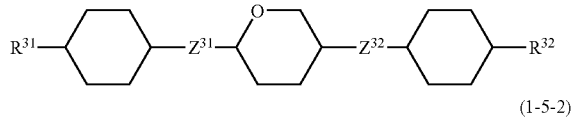

(1-5-1)

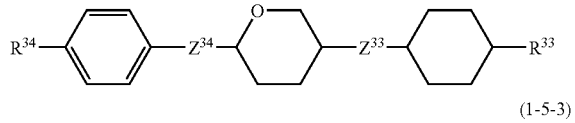

(1-5-2)

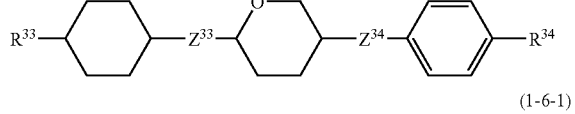

(1-5-3)

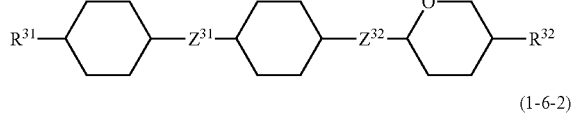

(1-6-1)

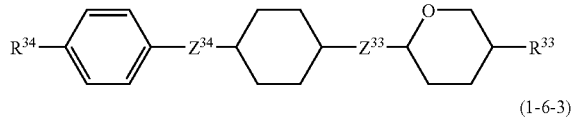

(1-6-2)

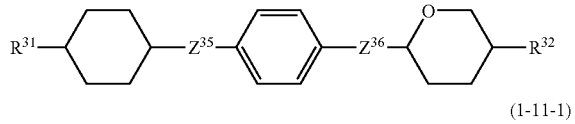

(1-6-3)

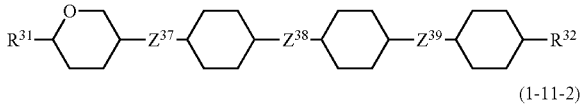

(1-11-1)

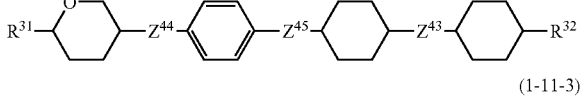

(1-11-2)

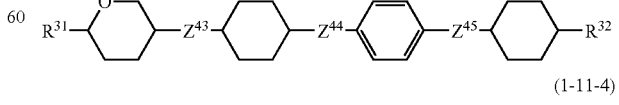

(1-11-3)

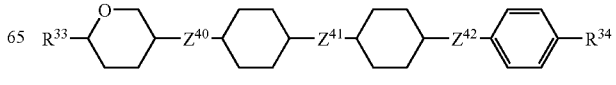

(1-11-4)

-continued

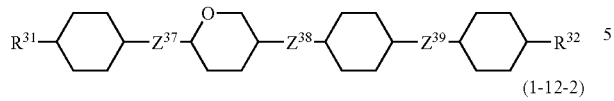
(1-12-1)

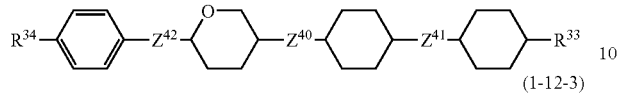
(1-12-2)

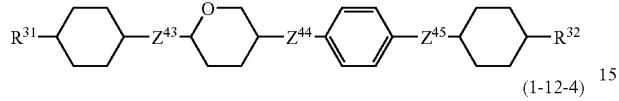
(1-12-3)

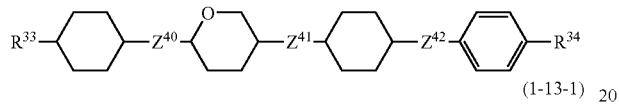
(1-12-4)

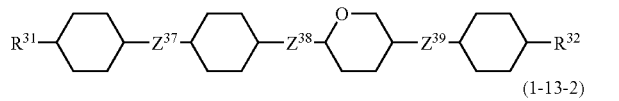
(1-13-1)

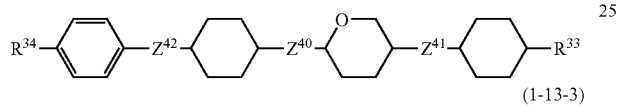
(1-13-2)

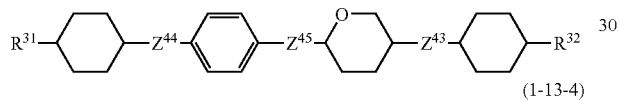
(1-13-3)

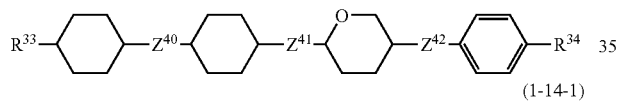
(1-13-4)

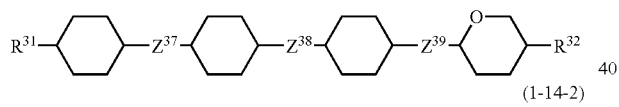
(1-14-1)

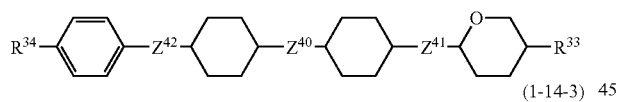
(1-14-2)

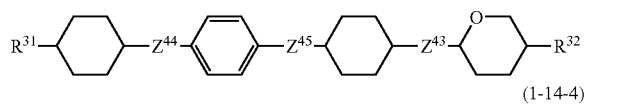
(1-14-3)

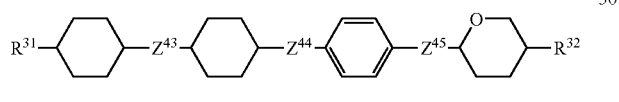
(1-14-4)

wherein $R^{31}$, $R^{32}$ and $R^{33}$ are independently alkyl having from 2 to 10 carbons, alkoxy having from 1 to 9 carbons or alkenyl having from 2 to 10 carbons; $R^{34}$ is alkyl having from 2 to 10 carbons, alkoxy having from 1 to 9 carbons or alkenyl having from 2 to 10 carbons other than 1-alkenyl; one of $R^{31}$ and $R^{32}$ is alkyl; one of $R^{33}$ and $R^{34}$ is alkyl; $Z^{31}$, $Z^{32}$, $Z^{33}$, $Z^{37}$, $Z^{38}$, $Z^{39}$, $Z^{40}$, $Z^{41}$ and $Z^{43}$ are independently a single bond, —(CH$_2$)$_2$— or —CH=CH—; $Z^{34}$, $Z^{35}$, $Z^{36}$, $Z^{42}$, $Z^{44}$ and $Z^{45}$ are independently a single bond or —(CH$_2$)$_2$—; one of $Z^{31}$ and $Z^{32}$ is a single bond; one of $Z^{33}$ and $Z^{34}$ is a single bond; one of $Z^{35}$ and $Z^{36}$ is a single bond; two of $Z^{37}$, $Z^{38}$ and $Z^{39}$ is a single bond; two of $Z^{40}$, $Z^{41}$ and $Z^{42}$ are a single bond; and two of $Z^{43}$, $Z^{44}$ and $Z^{45}$ are a single bond.

8. A compound represented by any one of the following formulae (1-1-1) and (1-2-1):

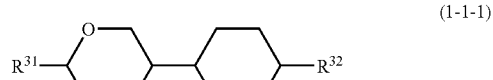
(1-1-1)

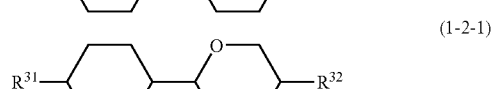
(1-2-1)

wherein $R^{31}$ and $R^{32}$ are independently alkyl having from 2 to 10 carbons, alkoxy having from 1 to 9 carbons or alkenyl having from 2 to 10 carbons; and one of $R^{31}$ and $R^{32}$ is alkyl.

9. A compound represented by any one of the following formulae (1-4-1), (1-5-1) and (1-6-1):

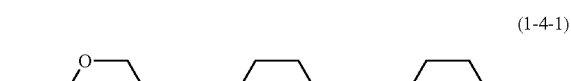
(1-4-1)

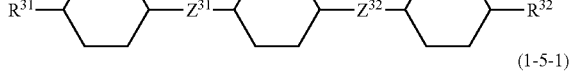
(1-5-1)

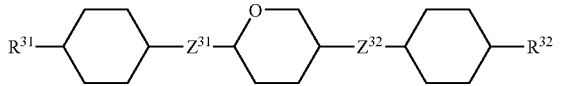
(1-6-1)

wherein $R^{31}$ and $R^{32}$ are independently alkyl having from 2 to 10 carbons, alkoxy having from 1 to 9 carbons or alkenyl having from 2 to 10 carbons; one of $R^{31}$ and $R^{32}$ is alkyl; $Z^{31}$ and $Z^{32}$ are independently a single bond, —(CH$_2$)$_2$— or —CH=CH—; and one of $Z^{31}$ and $Z^{32}$ is a single bond.

10. The compound according to item 8 or 9, wherein one of $R^{31}$ and $R^{32}$ is alkyl, and the other thereof is alkenyl.

11. The compound according to item 8 or 9, wherein $R^{31}$ and $R^{32}$ each represent alkenyl.

12. A liquid crystal composition comprising at least one of the compounds according to any one of items 1 to 11.

13. The liquid crystal composition according to item 12, wherein the composition further comprises at least one compound selected from compounds represented by the following formulae (2), (3) and (4):

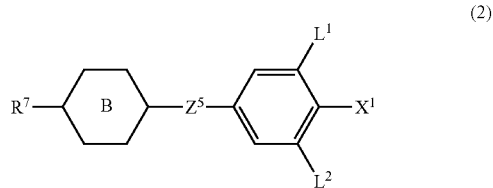
(2)

-continued

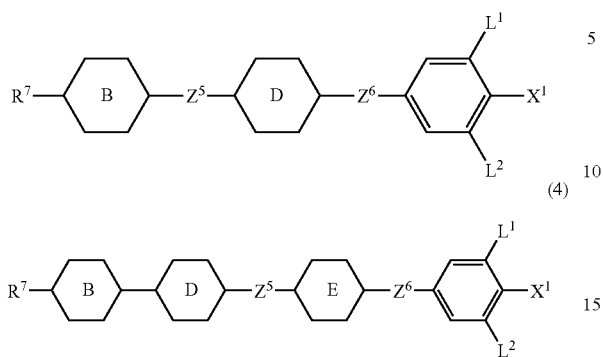

wherein $R^7$ is alkyl having from 1 to 10 carbons, provided that in the alkyl arbitrary —$CH_2$— may be replaced by —O— or —CH=CH—, and arbitrary hydrogen may be replaced by fluorine; $X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$; ring B and ring D are independently 1,4-cyclohexylene, 1,3-dioxane-2,5-diyl or 1,4-phenylene, provided that in the 1,4-phenylene arbitrary hydrogen may be replaced by fluorine; ring E is 1,4-cyclohexylene or 1,4-phenylene, provided that in the 1,4-phenylene arbitrary hydrogen may be replaced by fluorine; $Z^5$ and $Z^6$ are independently —$(CH_2)_2$—, —$(CH_2)_4$—, —COO—, —$CF_2O$—, —$OCF_2$—, —CH=CH— or a single bond; and $L^1$ and $L^2$ are independently hydrogen or fluorine.

14. The liquid crystal composition according to item 12, wherein the composition further comprises at least one compound selected from compounds represented by the following formulae (5) and (6):

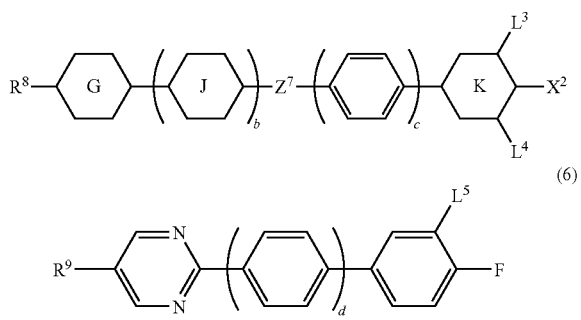

wherein $R^8$ and $R^9$ are independently alkyl having from 1 to 10 carbons, provided that in the alkyl arbitrary —$CH_2$— may be replaced by —O— or —CH=CH—, and arbitrary hydrogen may be replaced by fluorine; $X^2$ is —CH or —C≡C— CN; ring G is 1,4-cyclohexylene, 1,4-phenylene, 1,3-dioxane-2,5-diyl or pyrimidine-2,5-diyl; ring J is 1,4-cyclohexylene, pyrimidine-2,5-diyl or 1,4-phenylene, provided that in the 1,4-phenylene arbitrary hydrogen may be replaced by fluorine; ring K is 1,4-cyclohexylene or 1,4-phenylene; $Z^7$ is —$(CH_2)_2$—, —COO—, —$CF_2O$—, —$OCF_2$— or a single bond; $L^3$, $L^4$ and $L^5$ are independently hydrogen or fluorine; and b, c and d are independently 0 or 1.

15. The liquid crystal composition according to item 12, wherein the composition further comprises at least one compound selected from compounds represented by the following formulae (7), (8), (9), (10) and (11):

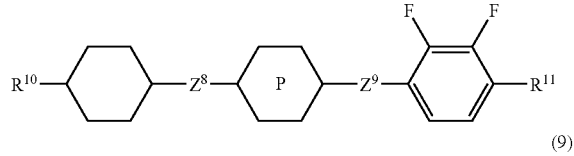

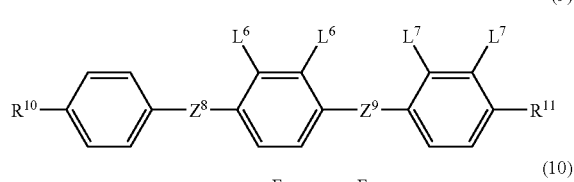

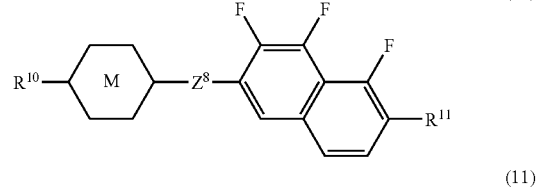

wherein $R^{10}$ and $R^{10}$ are independently alkyl having from 1 to 10 carbons, provided that in the alkyl arbitrary —$CH_2$— may be replaced by —O— or —CH=CH—, and arbitrary hydrogen may be replaced by fluorine, and $R^{10}$ may be fluorine; ring M and ring P are independently 1,4-cyclohexylene, 1,4-phenylene or decahydro-2,6-naphthylene; $Z^8$ and $Z^9$ are independently —$(CH_2)_2$—, —COO— or a single bond; $L^6$ and $L^7$ are independently hydrogen or fluorine; and at least one of $L^6$ and $L^7$ is fluorine.

16. The liquid crystal composition according to item 12, wherein the composition further comprises at least one compound selected from compounds represented by the following formulae (12), (13) and (14):

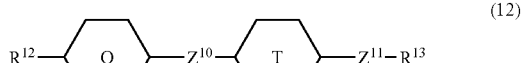

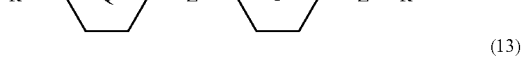

-continued

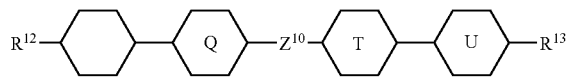
(14)

wherein $R^{12}$ and $R^{13}$ are independently alkyl having from 1 to 10 carbons, provided that in the alkyl arbitrary —$CH_2$— may be replaced by —O— or —CH=CH—, and arbitrary hydrogen may be replaced by fluorine; ring Q, ring T and ring U are independently 1,4-cyclohexylene, pyrimidine-2,5-diyl or 1,4-phenylene, provided that in the 1,4-phenylene arbitrary hydrogen may be replaced by fluorine; and $Z^{10}$ and $Z^{11}$ are independently —C≡C—, —COO—, —$(CH_2)_2$—, —CH=CH— or a single bond.

17. The liquid crystal composition according to item 13, wherein the composition further comprises at least one compound selected from compounds represented by the formulae (5) and (6) in item 14.

18. The liquid crystal composition according to item 13, wherein the composition further comprises at least one compound selected from compounds represented by the formulae (12), (13) and (14) in item 16.

19. The liquid crystal composition according to item 14, wherein the composition further comprises at least one compound selected from compounds represented by the formulae (12), (13) and (14) in item 16.

20. The liquid crystal composition according to item 15, wherein the composition further comprises at least one compound selected from compounds represented by the formulae (12), (13) and (14) in item 16.

21. The liquid crystal composition according to any one of items 12 to 20, wherein the composition further comprises at least one optically active compound.

22. The liquid crystal composition according to any one of items 12 to 21, wherein the composition comprises the compounds according to any one of items 1 to 11 in an amount of from approximately 5% to approximately 90% by weight based on the total weight of the liquid crystal composition.

23. A liquid crystal display device comprising the liquid crystal composition according to any one of items 12 to 22.

24. The liquid crystal display device according to item 23, wherein the display device is driven by active matrix based on a VA or ECB effect.

25. Use of the liquid crystal composition according to any one of items 12 to 22, in a liquid crystal display device.

First, the compound (1) of the invention will be described in more detail. A condensed ring, such as a naphthalene ring, is counted as one ring. The compound (1) includes a two-ring, three-ring or four-ring compound having a tetrahydrofuran ring. The compound is significantly stable physically and chemically under conditions, under which the device is used, and is good in compatibility with another liquid crystal compound. A composition containing the compound is stable under conditions, under which the device is used. Even when the composition is stored at a low temperature, the compound is not deposited as crystals (or a smectic phase). The compound has ordinary properties that are necessary for the compound, a suitable optical anisotropy and a suitable dielectric anisotropy.

The end groups, the rings and the bonding groups of the compound (1) can be appropriately selected to enable arbitrary control of the properties, such as the optical anisotropy. The effects of the end groups $R^1$ and $R^2$, the rings $A^1$ and $A^2$, and the bonding groups $Z^1$, $Z^2$, $Z^3$ and $Z^4$ on the properties of the compound (1) will be described below.

In the case where $R^1$ and $R^2$ are in a linear form, the compound has a wide temperature range of the liquid crystal phase, and has a small viscosity. In the case where $R^1$ and $R^2$ are in a branched form, the compound is good in compatibility with another liquid crystal compound. In the case where $R^1$ and $R^2$ are optically active groups, the compound is useful as a chiral dopant. By adding the compound to the composition, a reverse twisted domain occurring in the device can be prevented. The compound having $R^1$ and $R^2$ that are not optically active groups is useful as a component of the composition. In the case where $R^1$ and $R^2$ are alkenyls, a preferred steric configuration of the compound depends on the position of the double bond. An alkenyl compound having a preferred steric configuration has a high higher limit temperature or a wide temperature range of the liquid crystal phase. This is described in detail in *Mol. Cryst. Liq. Cryst.*, vol. 131, p. 109 (1985) and *Mol. Cryst. Liq. Cryst.*, vol. 131, p. 327 (1985).

In the case where the ring $A^1$ and $A^2$ are 1,4-phenylene, the compound has a large optical anisotropy. In the case where the ring $A^1$ and $A^2$ are 1,4-cyclohexylene, the compound has a small optical anisotropy.

In the case where at least two rings are 1,4-cyclohexylene, the compound has a higher higher limit temperature, a small optical anisotropy and a small viscosity. In the case where at least one ring is 1,4-phenylene, the compound has a relatively large optical anisotropy and a large orientational order parameter.

In the case where the bonding groups $Z^1$, $Z^2$, $Z^3$ and $Z^4$ are a single bond, —$(CH_2)_2$—, —$CH_2O$—, —CH=CH— or —$(CH_2)_4$—, the compound has a small viscosity. In the case where the bonding groups are a single bond, —$(CH_2)_2$— or —CH=CH—, the compound has a smaller viscosity. In the case where the bonding groups are —CH=CH—, the compound has a wide temperature range of the liquid crystal phase and a large elastic constant ratio $K_{33}/K_{11}$ ($K_{33}$: bend elastic constant, $K_{11}$: splay elastic constant). In the case where the bonding groups are —C≡C—, the compound has a large optical anisotropy.

In the case where the compound (1) has a two-ring or three-ring structure, the compound has a small viscosity. In the case where the compound (1) has a three-ring or four-ring structure, the compound has a higher higher limit temperature. As having been described, a compound having target properties can be obtained by appropriately selecting the kinds of the end groups, the ring and the bonding groups and the number of the rings. Therefore, the compound (1) is useful as a component of a compound used in various devices including PC, TN, STN, ECB, OCB, IPS and VA.

Preferred examples of the compound (1) include the compounds (1-1), (1-2), (1-4) to (1-6), and (1-11) to (1-14) described in the item 2. The meanings of the symbols $R^1$, $R^2$, $R^3$, $R^4$, $R^5$, $R^6$, $A^1$, $A^2$, $Z^1$, $Z^2$, $Z^3$ and $Z^4$ in these formulae are the same as the symbols described in the item 2.

The compound (1) can be synthesized by appropriately combining the methods known in the filed of synthetic organic chemistry. The methods for introducing the target end group, ring and bonding group to the starting material are disclosed in known publications, such as *Organic Synthesis*, published by John Wiley & Sons, Inc., *Organic Reactions*, published by John Wiley & Sons, Inc., *Comprehensive Organic Synthesis*, published by Pergamon Press, and *Shin Jikken Kagaku Koza* (Lectures on New Experimental Chemistry), published by Maruzen, Inc.

An example of the method for forming the bonding group $Z^1$, $Z^2$, $Z^3$ or $Z^4$ will be described with reference firstly to a reaction scheme and then to the items (I) to (XI) for describing the scheme. In the scheme, MSG$^1$ and MSG$^2$ each represents a monovalent organic group having at least one ring. The plural groups represented by MSG$^1$ (or MSG$^2$) used in the scheme may be the same as or different from each other. The compounds (1A) to (1K) correspond to the compound (1).

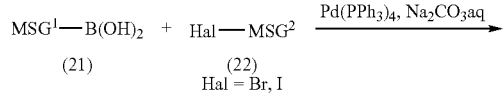

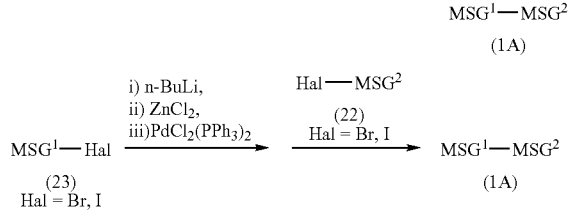

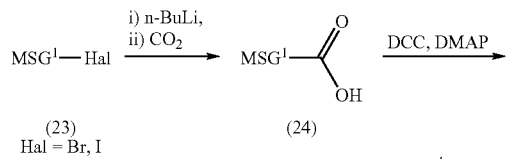

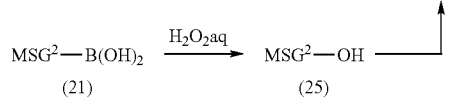

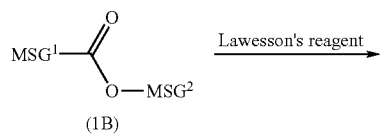

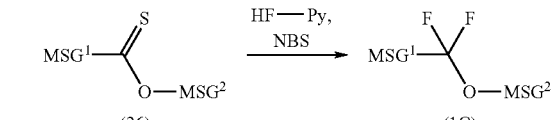

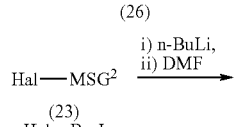

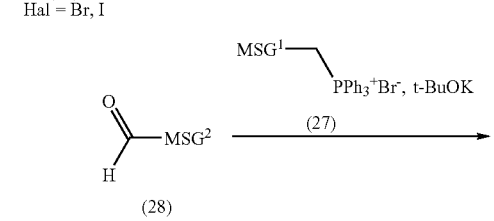

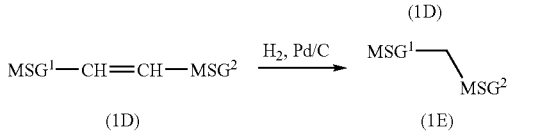

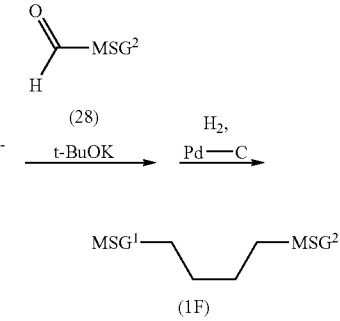

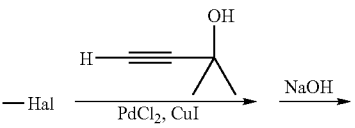

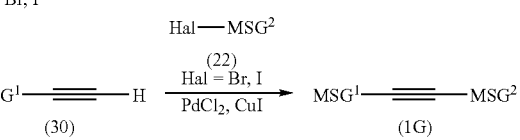

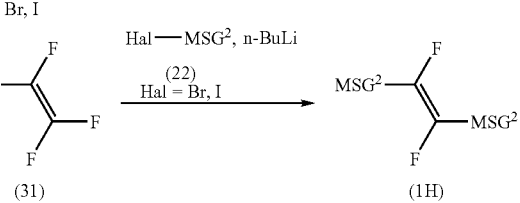

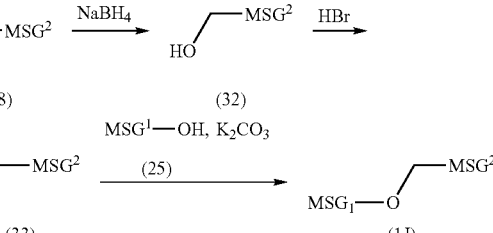

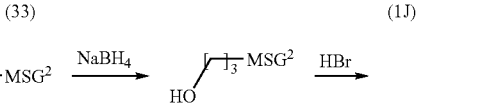

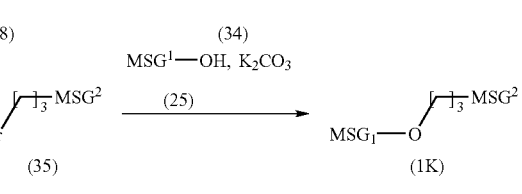

(I) Formation of Single Bond

Arylboric acid (21) and a compound (22), which is synthesized in the known method, are reacted in the presence of a carbonate aqueous solution and a catalyst, such as tetrakis(triphenylphosphine)palladium, to synthesize a compound (1A). The compound (1A) can also be synthesized in such a manner that a compound (23), which is synthesized in the known method, is reacted with n-butyllithium and then reacted with zinc chloride, and then reacted with a compound (22) in the presence of a catalyst, such as dichloro-bis(triphenylphsophine)palladium.

(II) Formation of —COO— and —OCO—

A compound (23) is reacted with n-butyllithium and then with carbon dioxide to obtain a carboxylic acid (24). The compound (24) and a phenol compound (25), which is synthesized in the known method, are subjected to dehydration in the presence of DCC (1,3-dicyclohexylcarbodiimide) and DMAP (4-dimethylaminopyridine) to synthesize a compound (1B) having —COO—. A compound having —OCO— is produced in the same manner.

(III) Formation of —CF$_2$O— and —OCF$_2$—

A compound (1B) is treated with a sulfurating agent, such as Lawson reagent, to obtain a compound (26). The compound (26) is fluorinated with hydrogen fluoride pyridine complex and NBS (N-bromosuccinimide) to synthesize a compound (1C) having —CF$_2$O—. The reaction is described in M. Kuroboshi, et al., *Chem. Lett.*, 1992, p. 827. The compound (1C) can also be synthesized by fluorinating the compound (26) with (diethylamino) sulfur trifluoride (DAST). The reaction is described in W. H. Bunnelle, et al., *J. Org. Chem.*, vol. 55, p. 768 (1990). A compound having —OCF$_2$— is produced in the same manner. These bonding groups can also be formed by the method described in Peer. Kirsch, et al., *Anbew. Chem. Int. Ed.*, vol. 40, p. 1480 (2001).

(IV) Formation of —CH═CH—

A compound (23) is treated with n-butyllithium and then reacted with a formamide, such as N,N-dimethylformamide (DMF), to obtain an aldehyde compound (28). A phosphonium salt (27), which is synthesized in the known method, is treated with a base, such as potassium tert-butoxide, to form phosphoylide, which is then reacted with the aldehyde compound (28) to synthesize a compound (1D). A cis-compound is formed depending on the reaction conditions, and the cis-compound is isomerized to a trans-compound by the known method depending on necessity.

(V) Formation of —(CH$_2$)$_2$—

A compound (1D) is hydrogenated in the presence of a catalyst, such as palladium charcoal, to synthesize a compound (1E).

(VI) Formation of —(CH$_2$)$_4$—

A compound having —(CH$_2$)$_2$—CH═CH— is obtained in the same manner as described in the item (IV) by using a phosphonium salt (29) instead of the phosphonium salt (27). The compound is subjected catalytic hydrogenation to synthesize a compound (1F).

(VII) Formation of —C≡C—

A compound (23) is reacted with 2-methyl-3-butyne-2-ol in the presence of a catalyst containing dichloropalladium and copper halogenide and then deprotected under the basic conditions to obtain a compound (30). The compound (30) is reacted with a compound (22) in the presence of a catalyst containing dichloropalladium and copper halogenide to synthesize a compound (1G).

(VIII) Formation of —C≡C—

A compound (23) is treated with n-butyllithium and then reacted with tetrafluoroethylene to obtain a compound (31). A compound (22) is treated with n-butyllithium and then reacted with the compound (31) to synthesize a compound (1H).

(IX) Formation of —CH$_2$O— or —OCH$_2$—

A compound (28) is reduced with a reducing agent, such as sodium borohydride, to obtain a compound (32), which is then halogenated with hydrobromic acid or the like to obtain a compound (33). The compound (33) is reacted with a compound (25) in the presence of potassium carbonate or the like to synthesize a compound (1J).

(X) Formation of —(CH$_2$)$_3$O— or —O(CH$_2$)$_3$—

A compound (1K) is synthesized in the same manner as in the item (IX) except that a compound (34) is used instead of the compound (32).

(XI) Formation of —(CF$_2$)$_2$—

A diketone (—COCO—) is fluorinated with sulfur tetrafluoride in the presence of a hydrogen fluoride catalyst according to the method described in *J. Am. Chem. Soc.*, vol. 123, p. 5414 (2001) to obtain a compound having —(CF$_2$)$_2$—.

An example of a method for synthesizing a tetrahydropyran compound represented by the formula (1) where i=0, k>0 and n=0 is shown by the following scheme. A scheme of synthesizing a synthetic intermediate (39) having a lactone skeleton is firstly described, and then an example of a method for synthesizing a tetrahydropyran compound (42) with the compound (39) as a starting material is described.

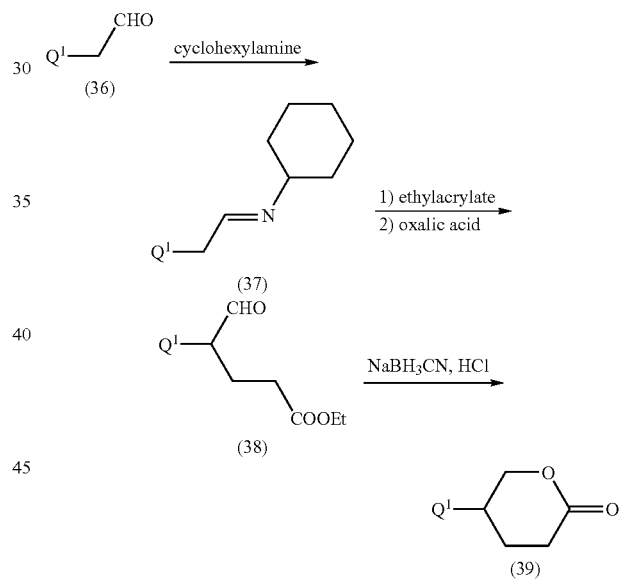

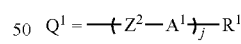

In the compounds (36) to (39), Q$^2$ represents the structural unit of the formula (1). The symbols R$^1$, A$^1$ and Z$^2$ in the compounds have the same meanings as those in the formula (1).

A compound (37) is synthesized by reacting a compound (36) and cyclohexylamine. The reaction is preferably carried out in a solvent, such as diethyl ether, in the presence of a catalyst, such as potassium carbonate, at a temperature between room temperature to the boiling point of the solvent used. A compound (38) is synthesized by adding ethyl acrylate to the compound (37) and then deprotecting the compound. The reaction is preferably carried out by using ethyl acrylate as a solvent by itself, and such a solvent may be used that is not reacted with the compound (37) and ethyl acrylate. In order to prevent ethyl acrylate from being polymerized, a polymerization inhibitor, such as hydroquinone, is preferably added. The reaction is carried out at a temperature between room temperature to the boiling point of the solvent used upon using an ordinary glass reactor, and the reaction can be carried out at a temperature higher than the boiling point of the solvent by using a pressure reactor, such as a stainless steel autoclave. After sufficiently effecting the addition reaction, cyclohexylamine is released by adding an acid, such as oxalic acid, to obtain the compound (38). The compound (39) is obtained by subjecting the compound (38) to a cyclization reaction. The reaction is preferably carried out in a solvent, such as isopropanol, in the presence of sodium cyanoborohydride at a temperature around room temperature. An acid, such as hydrochloric acid, may be added for accelerating the reaction.

The compound (36) as the starting material can be easily synthesized by the ordinary method known in the field of synthetic organic chemistry.

An example of a synthesis method of a compound (42) will be described.

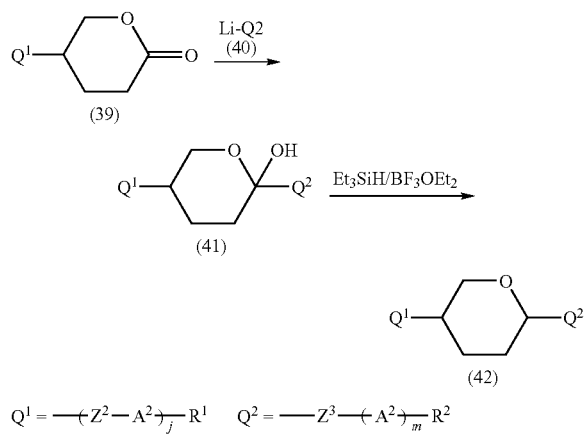

In the compounds (39) to (42), $Q^1$ and $Q^2$ each represents the structural unit of the formula (1). The structural unit is shown in the scheme. The symbols $R^1$, $R^2$, $A^1$, $A^2$, $Z^2$ and $Z^3$ in the compounds have the same meanings as those in the formula (1).

A compound (41) is synthesized by reacting a compound (39) with a compound (40). The reaction is preferably carried out in a solvent, such as tetrahydrofuran, at a temperature of approximately −30° C. A compound (42) is synthesized by reacting the compound (41) in a solvent, such as dichloromethane, in the presence of triethylsilane and boron trifluoride diethyl ether complex at a temperature of approximately −50° C. or lower.

The compound (40) can be easily synthesized by the ordinary method known in the field of synthetic organic chemistry.

The tetrahydropyran compound represented by the formula (1) in the case other than the case where i=0, k>0 and n=0 can be synthesized in the similar manner.

An example of a synthesis method of a compound (46) will be described.

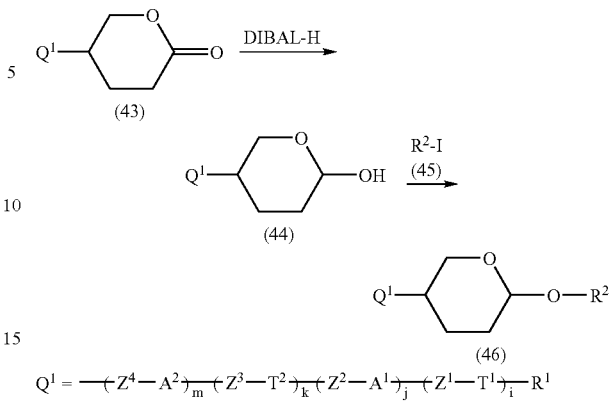

In the compounds (43) to (46), $Q^1$ and $Q^2$ each represents the structural unit of the formula (1). The structural unit is shown in the scheme. The symbols $R^1$, $R^2$, $A^1$, $A^2$, $Z^2$ and $Z^3$ in the compounds have the same meanings as those in the formula (1).

A compound (44) is synthesized by reducing a compound (43) with DIBAL-H. The reaction is preferably carried out in a solvent, such as toluene, at a temperature of approximately −60° C. or lower. A compound (46) is synthesized by reacting the compound (44) with the compound (45) in the presence of base, such as potassium carbonate.

The compound (45) can be easily synthesized by the ordinary method known in the field of synthetic organic chemistry.

Second, the composition of the invention will be then described in more detail. A preferred example of the composition contains at least one compound selected from the compounds represented by the formula (1) in a proportion of from approximately 1% to approximately 99%. The composition mainly contains a component selected from the compounds (2) to (14).

A preferred example of the composition containing the compound (1) is as follows. An example of the preferred composition contains at least one compound selected from the group consisting of the compounds (2), (3) and (4). Another example of the preferred composition contains at least one compound selected from the group consisting of the compounds (5) and (6). Still another example of the preferred composition contains at least two compounds selected from the aforementioned two groups, respectively. These compositions may further contain at least one compound selected from the group consisting of the compounds (12), (13) and (14) for such purposes as adjustments of the temperature range of the liquid crystal phase, the viscosity, the optical anisotropy, the dielectric anisotropy and the threshold voltage. The compositions may further contain at least one compound selected from the group consisting of the compounds (7) to (11) for further adjusting the properties. The compositions may further contain another liquid crystal compound and a compound, such as an additive, for optimizing to an AM-TN device and an STN device.

A further example of the preferred composition contains at least one compound selected from the group consisting of the compounds (7) to (11). The composition may further contain at least one compound selected from the group consisting of the compounds (12), (13) and (14). The composition may further contain at least one compound selected from the group consisting of the compounds (2) to (6) for further adjusting the properties. The composition may further contain another liquid crystal compound and a compound, such as an additive, for optimizing to a VA device.

The compounds (2), (3) and (4) are used mainly in a composition for an AM-TN device owing to the large positive dielectric anisotropy thereof. In the composition, the amount of these compounds is generally from approximately 1% to approximately 99%, preferably from approximately 10% to approximately 97%, and more preferably from approximately 40% to approximately 95%. In the case where the compounds (12), (13) and (14) are added to the composition, the amount of these compounds is preferably approximately 60% or less, and more preferably approximately 40% or less.

The compounds (5) and (6) are used mainly in a composition for an STN device owing to the extremely large positive dielectric anisotropy thereof. In the composition, the amount of these compounds is generally from approximately 1% to approximately 99%, preferably from approximately 10% to approximately 97%, and more preferably from approximately 40% to approximately 95%. In the case where the compounds (12), (13) and (14) are added to the composition, the amount of these compounds is preferably approximately 60% or less, and more preferably approximately 40% or less.

The compounds (7), (8), (9), (10) and (11) are used mainly in a composition for a VA device owing to the negative dielectric anisotropy thereof. In the composition, the amount of these compounds is preferably approximately 80% or less, and more preferably from approximately 40% to approximately 80%. In the case where the compounds (12), (13) and (14) are added to the composition, the amount of these compounds is preferably approximately 60% or less, and more preferably approximately 40% or less.

The compounds (12), (13) and (14) have a small dielectric anisotropy. The compound (12) is used mainly for adjusting the viscosity or the optical anisotropy. The compounds (13) and (14) increase the higher limit temperature and expand the temperature range of the liquid crystal phase. The compounds (13) and (14) are also used for adjusting the optical anisotropy. By increasing the amount of the compounds (12), (13) and (14), the threshold voltage of the composition is increased, and the viscosity thereof is decreased. Therefore, these compounds may be used in a large amount for satisfying a desired value of the threshold voltage of the composition.

Preferred examples of the compounds (2) to (14) include the compounds (2-1) to (2-9), the compounds (3-1) to (3-97), the compounds (4-1) to (4-33), the compounds (5-1) to (5-56), the compounds (6-1) to (6-3), the compounds (7-1) to (7-4), the compounds (8-1) to (8-6), the compounds (9-1) to (9-4), the compound (10-1), the compound (11-1), the compounds (12-1) to (12-11), the compounds (13-1) to (13-21), and the compounds (14-1) to (14-6), shown below. In the compounds, the symbols $R^7$, $R^9$ and $X^1$ have the same meanings as those in the compounds (2) to (14).

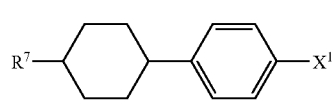
(2-1)

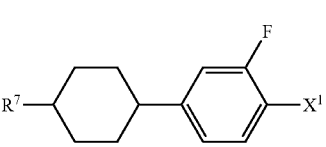
(2-2)

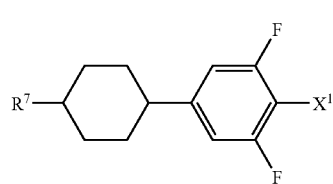
(2-3)

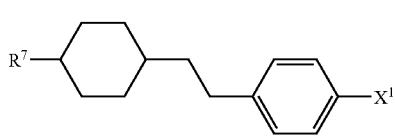
(2-4)

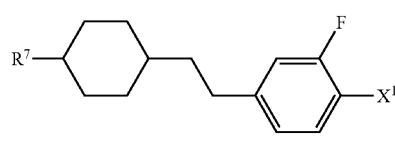
(2-5)

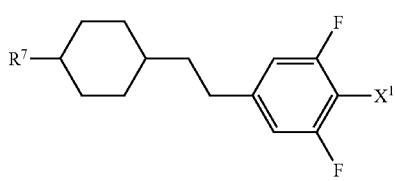
(2-6)

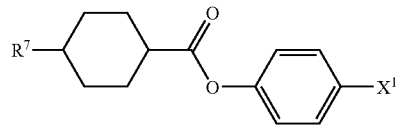
(2-7)

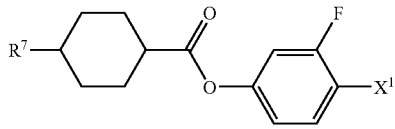
(2-8)

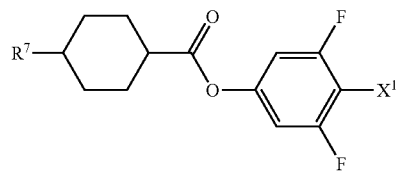
(2-9)

(3-1)

-continued
(3-2) 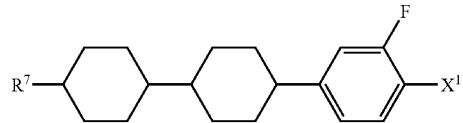
(3-3) 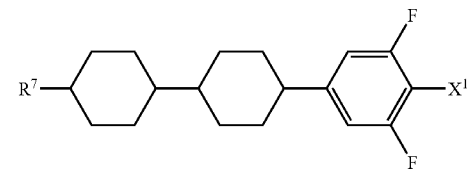
(3-4) 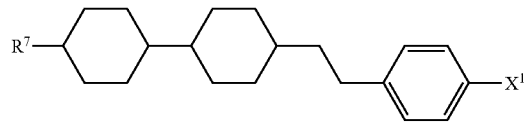
(3-5) 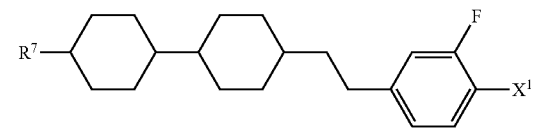
(3-6) 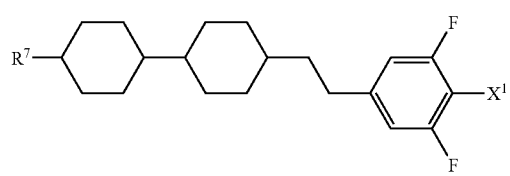
(3-7) 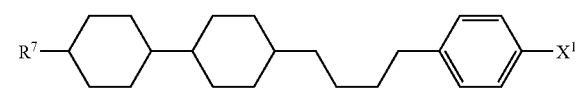
(3-8) 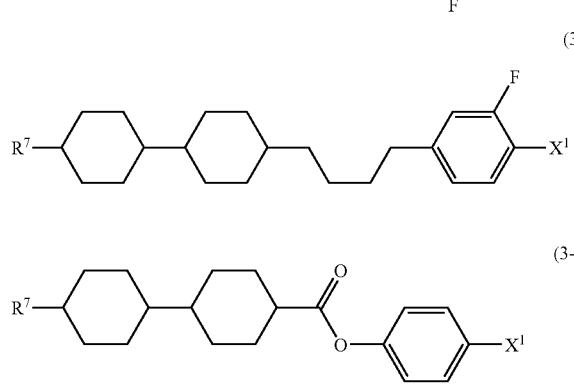
(3-9) 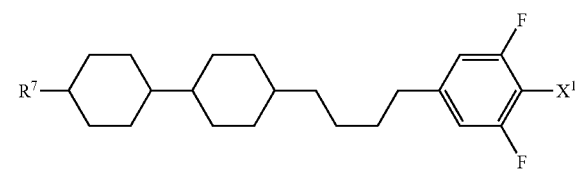
(3-10) 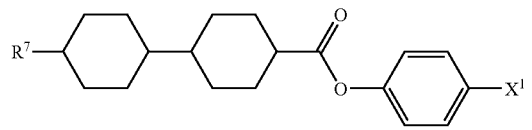
(3-11) 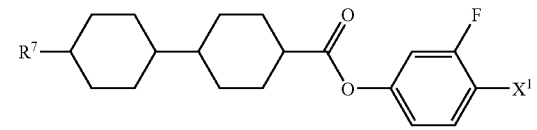
(3-12) 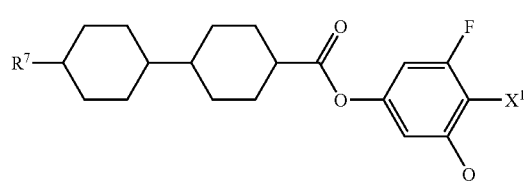
(3-13) 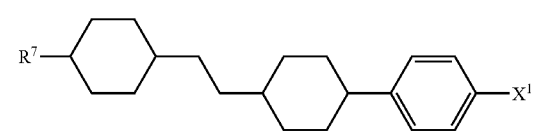
(3-14) 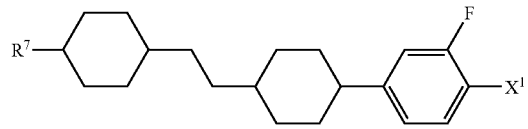
(3-15) 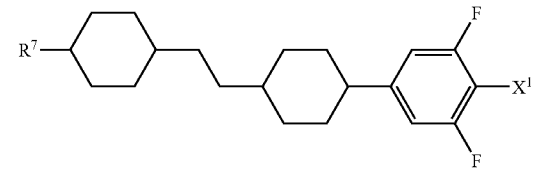
(3-16) 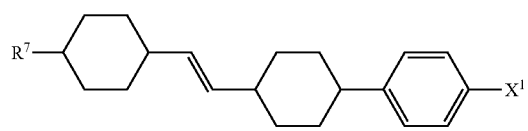
(3-17) 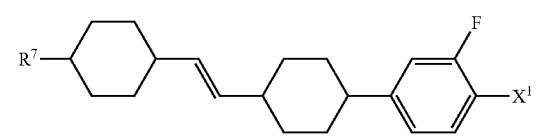
(3-18) 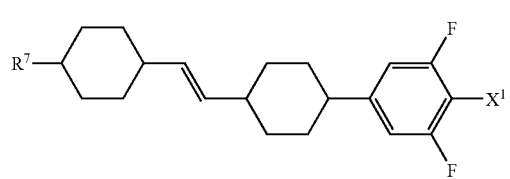
(3-19) 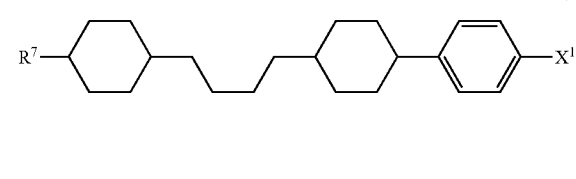

-continued
(3-20)
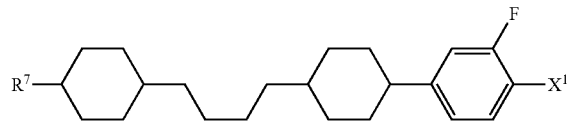
(3-21)
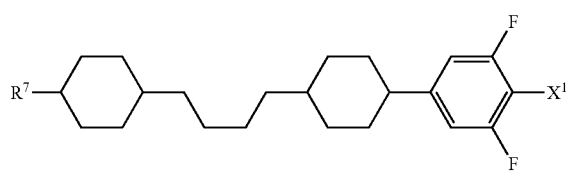
(3-22)
(3-23)
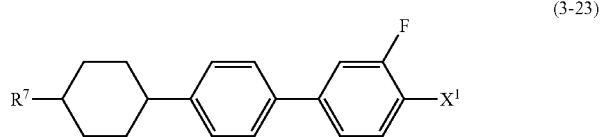
(3-24)
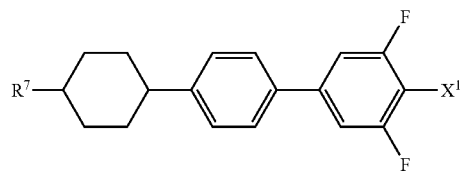
(3-25)
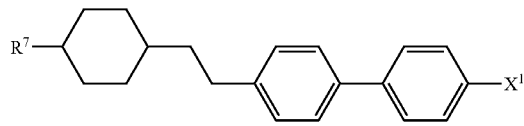
(3-26)
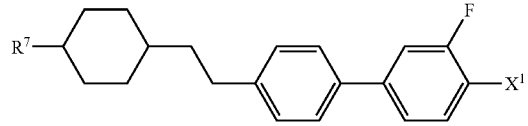
(3-27)
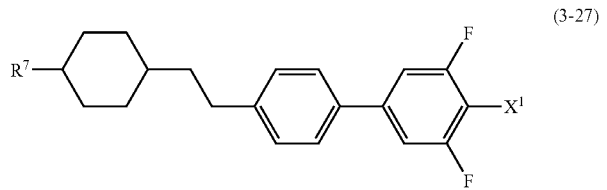
(3-28)
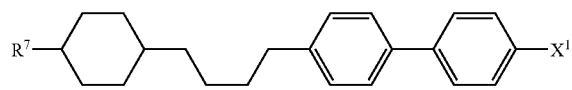
(3-29)
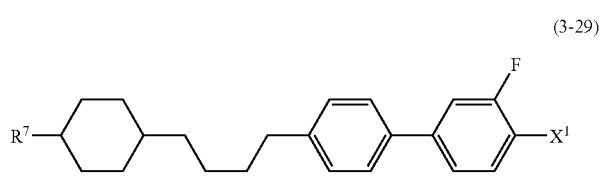
(3-30)
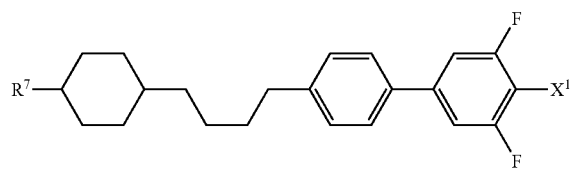
(3-31)
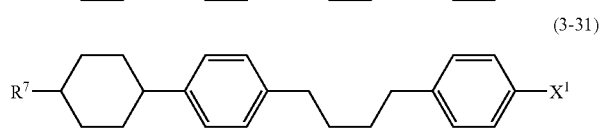
(3-32)
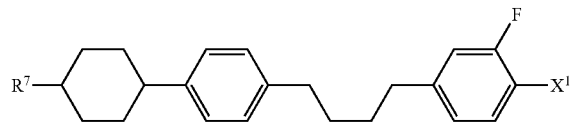
(3-33)
(3-34)
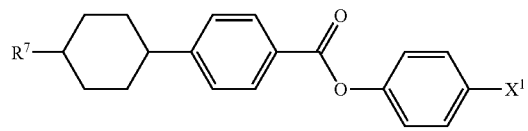
(3-35)
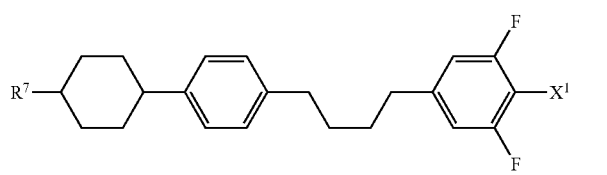
(3-36)
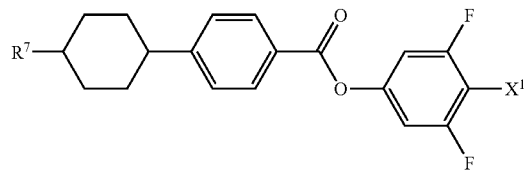
(3-37)
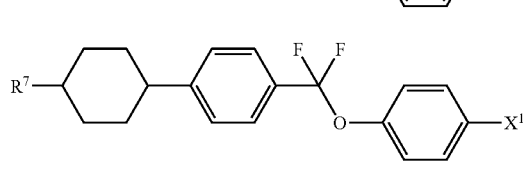

-continued
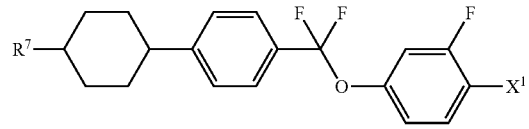 (3-38)
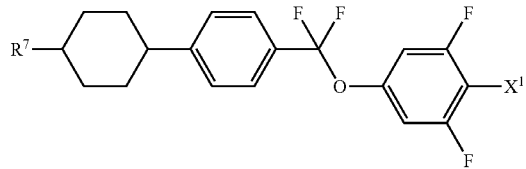 (3-39)
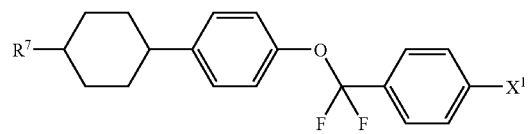 (3-40)
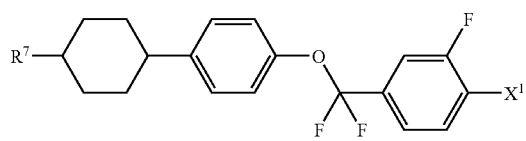 (3-41)
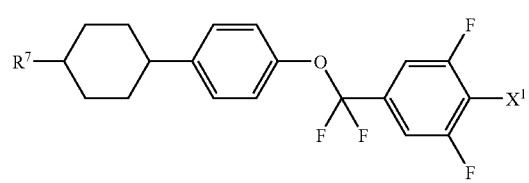 (3-42)
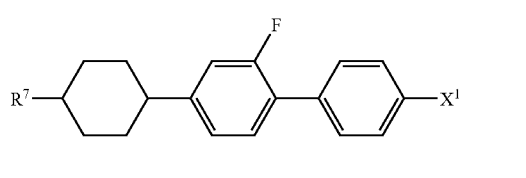 (3-43)
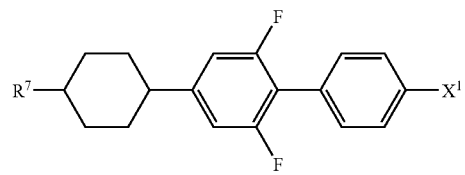 (3-44)
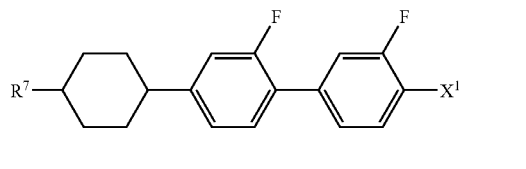 (3-45)
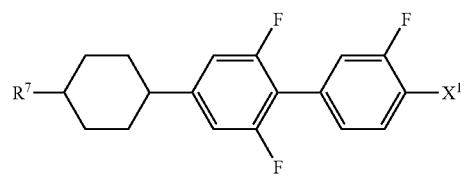 (3-46)
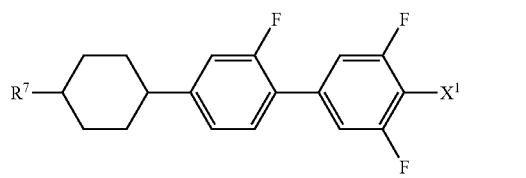 (3-47)
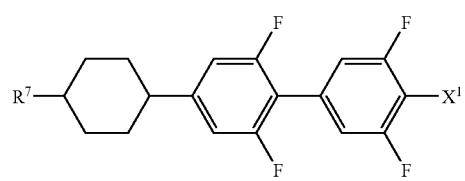 (3-48)
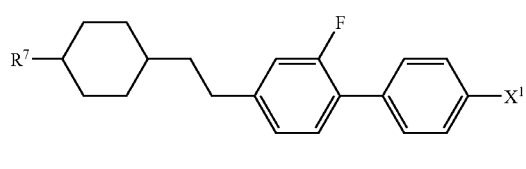 (3-49)
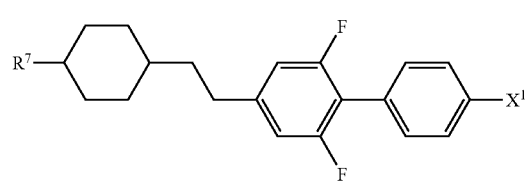 (3-50)
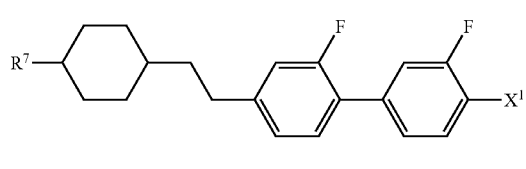 (3-51)
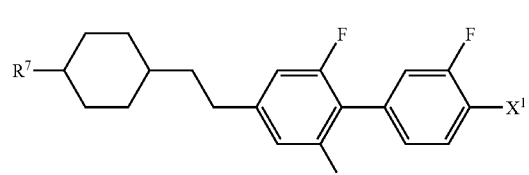 (3-52)
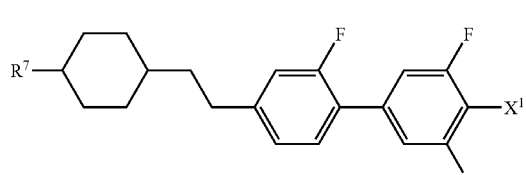 (3-53)
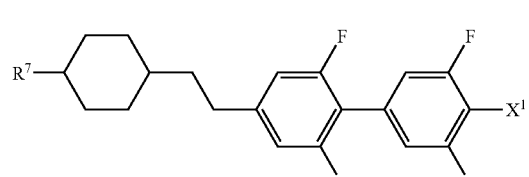 (3-54)
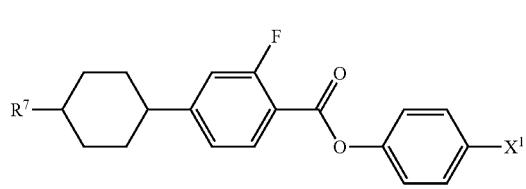 (3-55)

-continued
(3-56) 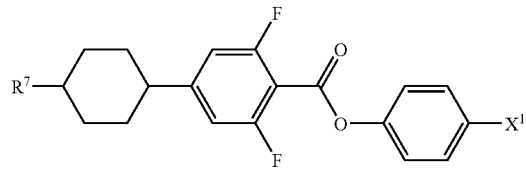
(3-57) 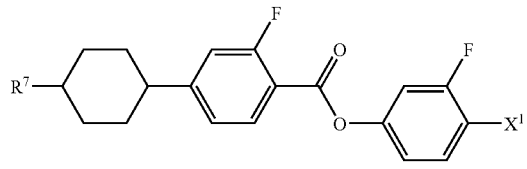
(3-58) 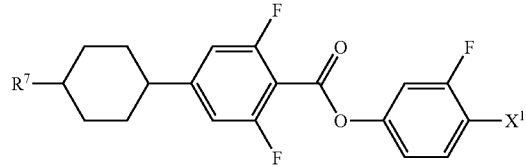
(3-59) 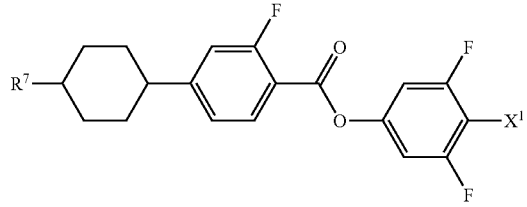
(3-60) 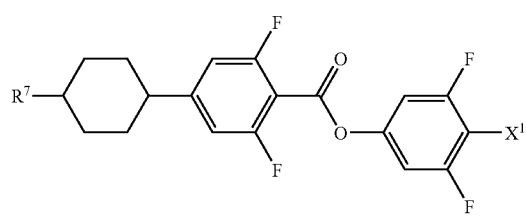
(3-61) 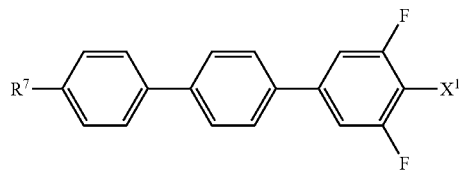
(3-62) 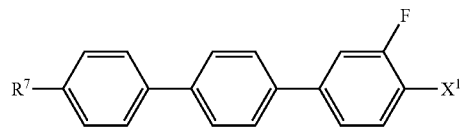
(3-63) 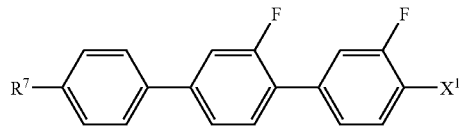
(3-64) 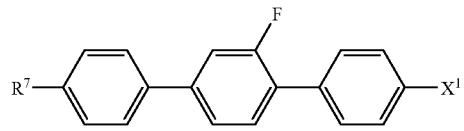
(3-65) 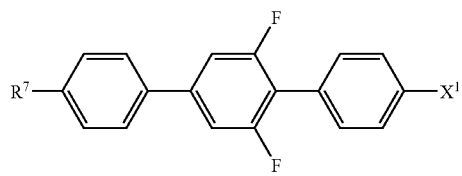
(3-66) 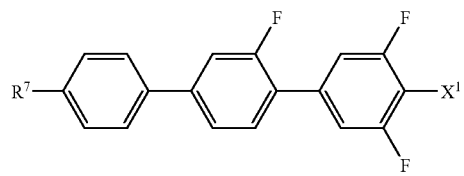
(3-67) 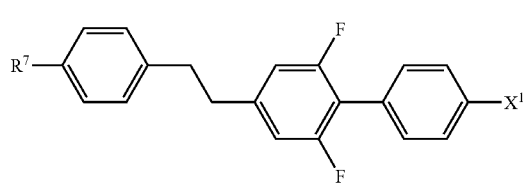
(3-68) 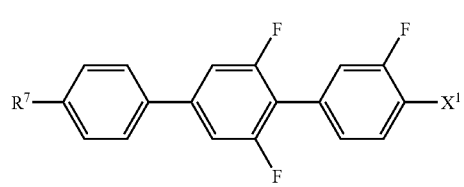
(3-69) 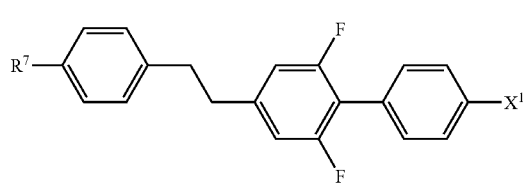
(3-70) 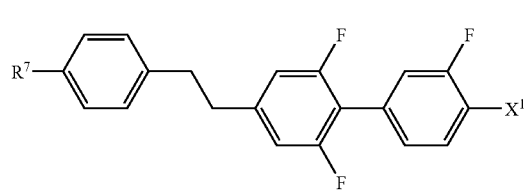
(3-71) 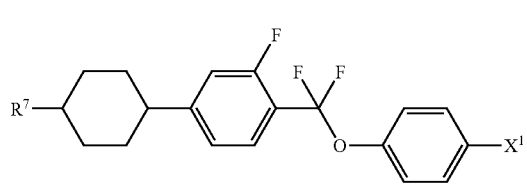

-continued
(3-72) 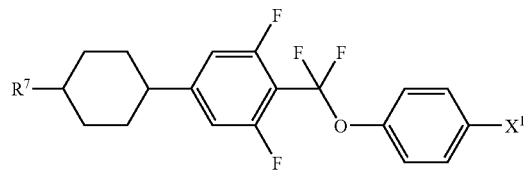
(3-73) 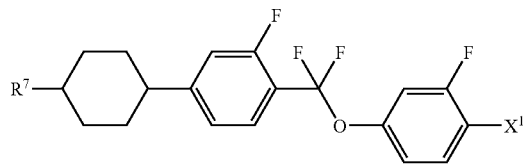
(3-74) 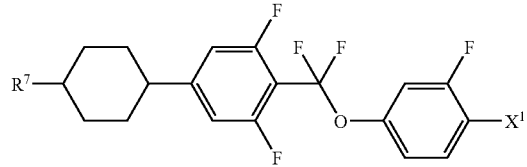
(3-75) 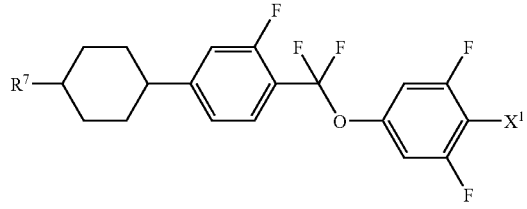
(3-76) 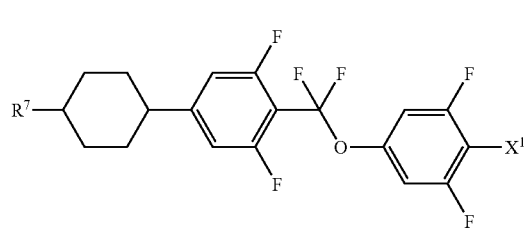
(3-77) 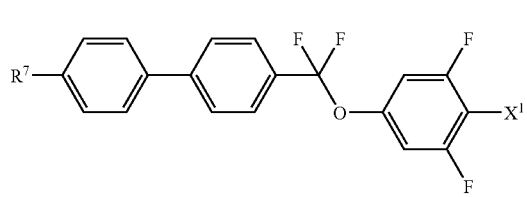
(3-78) 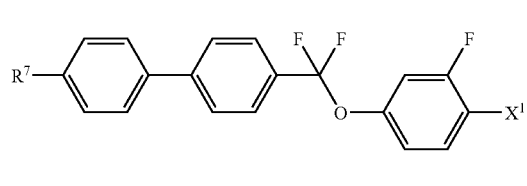
(3-79) 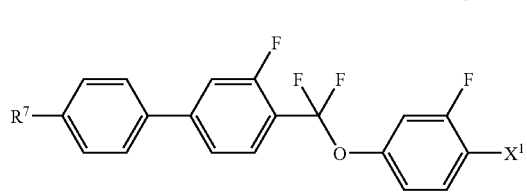
(3-80) 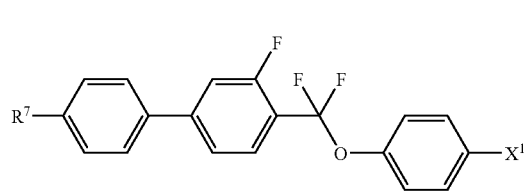
(3-81) 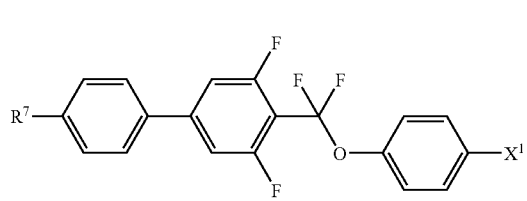
(3-82) 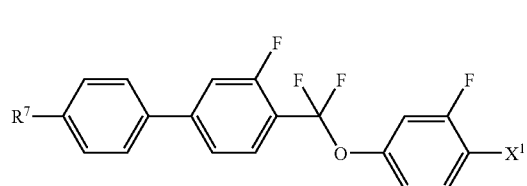
(3-83) 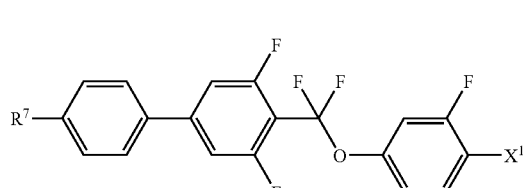
(3-84) 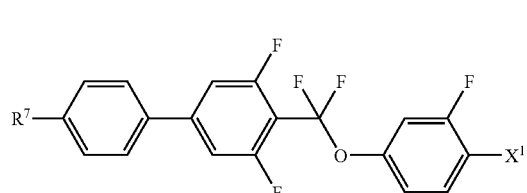
(3-85) 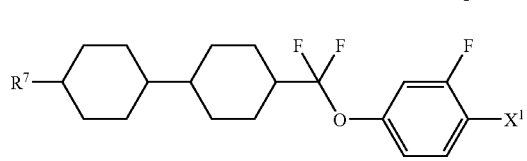
(3-86) 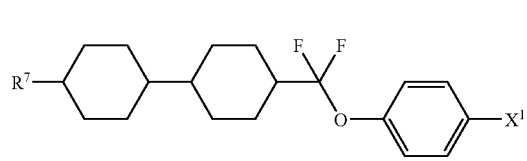
(3-87) 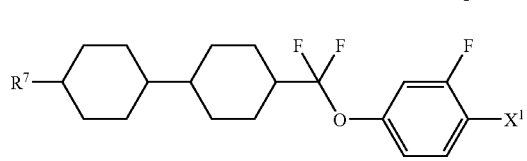

-continued
(3-88)
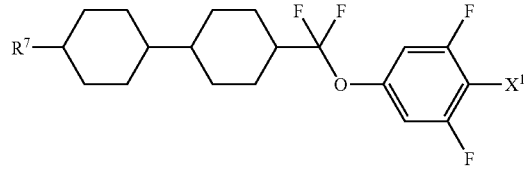
(3-89)
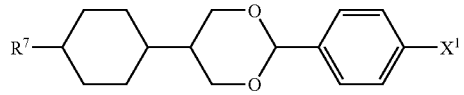
(3-90)
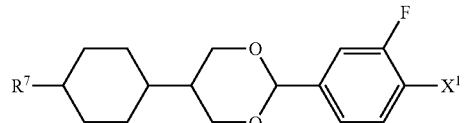
(3-91)
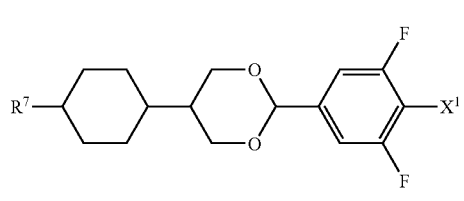
(3-92)
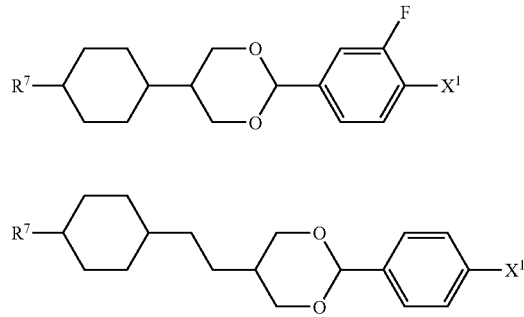
(3-93)
(3-94)
(3-95)
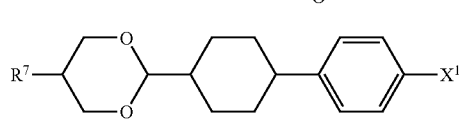
(3-96)
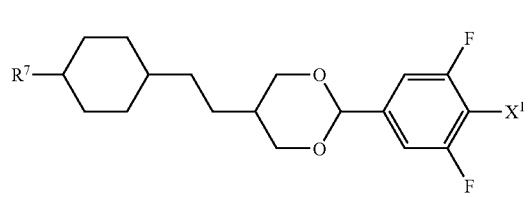
(3-97)
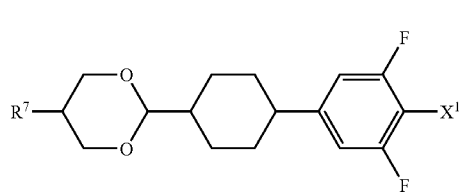
(4-1)
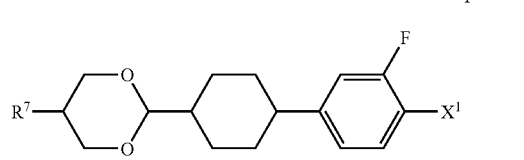
(4-2)
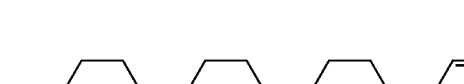
(4-3)
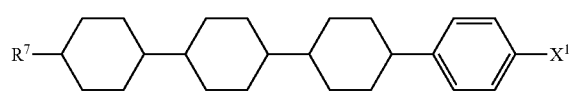
(4-4)
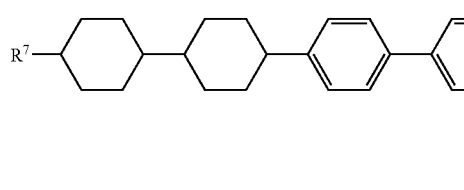
(4-5)
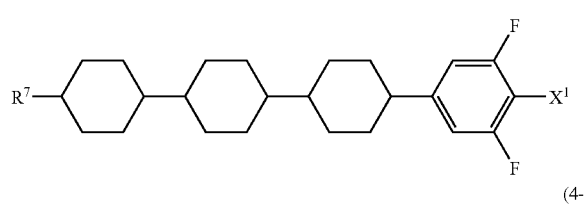
(4-6)
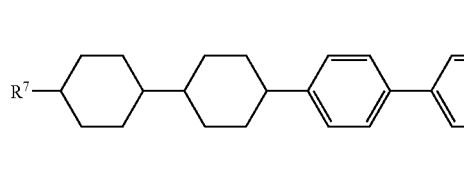
(4-7)
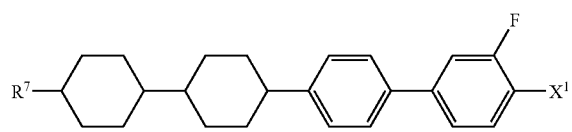
(4-8)
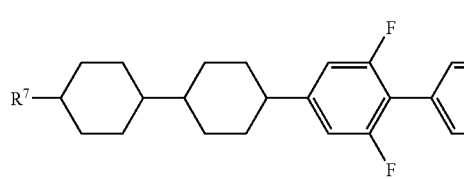
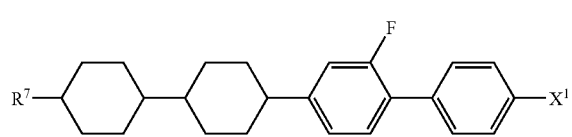

-continued
(4-9)
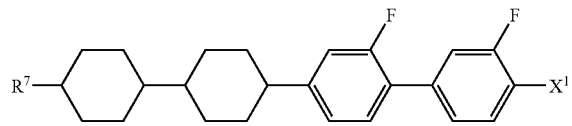
(4-10)
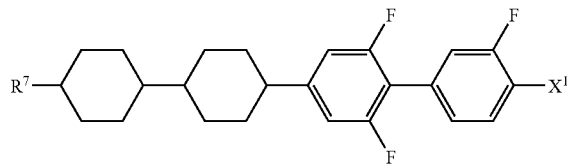
(4-11)
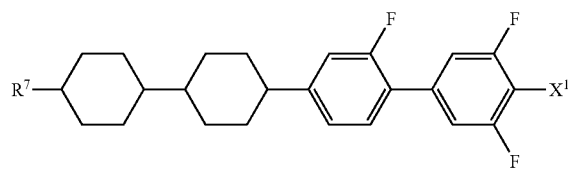
(4-12)
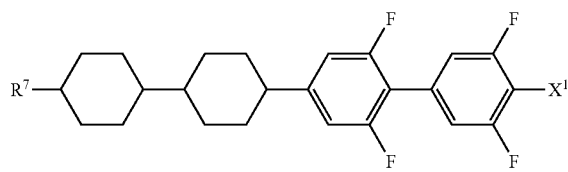
(4-13)
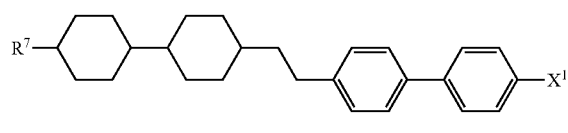
(4-14)
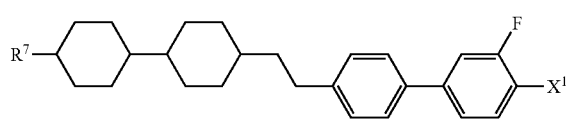
(4-15)
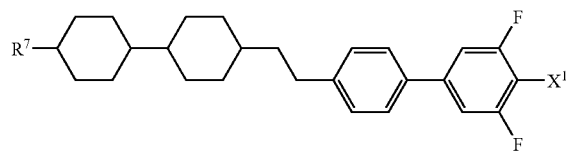
(4-16)
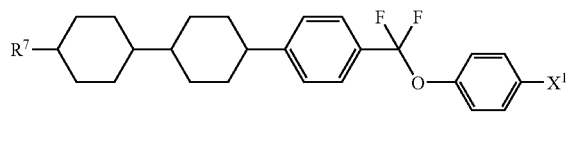
(4-17)
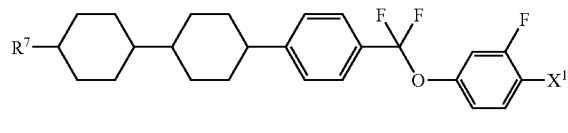
(4-18)
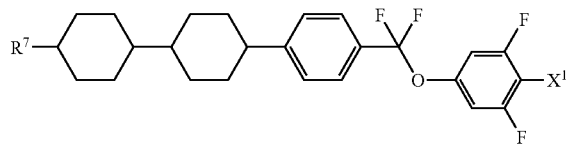
(4-19)
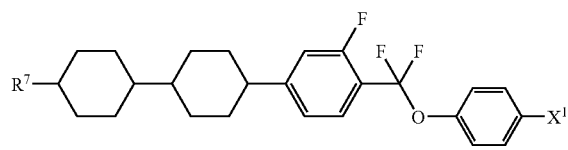
(4-20)
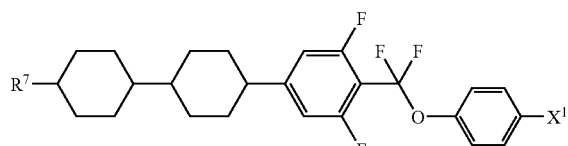
(4-21)
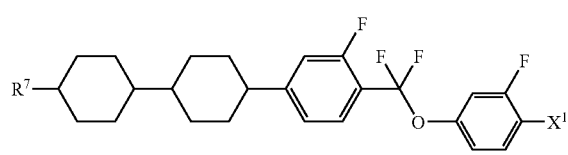
(4-22)
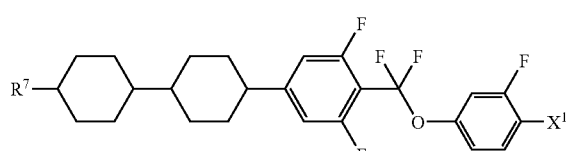
(4-23)
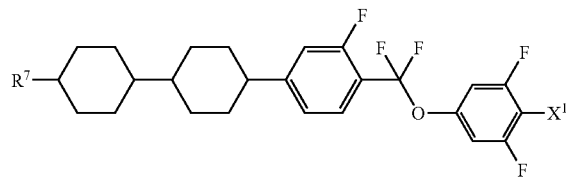
(4-24)
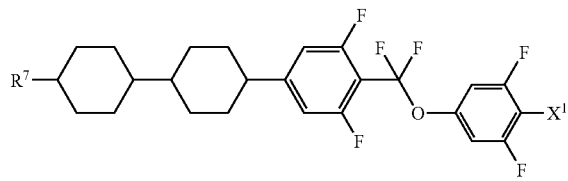
(4-25)
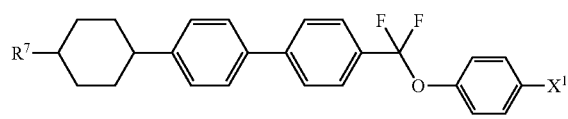
(4-26)
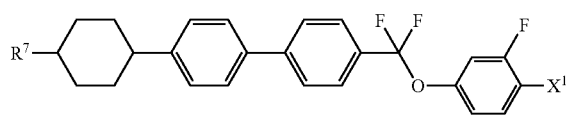

-continued
(4-27) 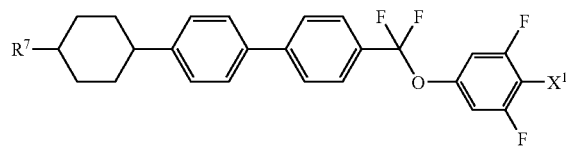
(4-28) 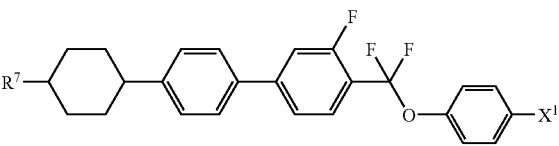
(4-29) 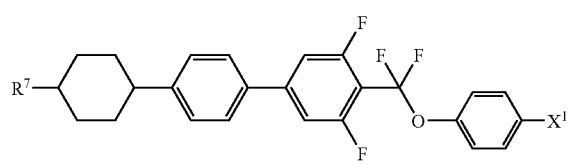
(4-30) 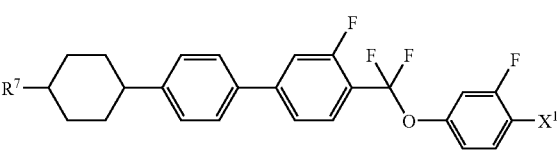
(4-31) 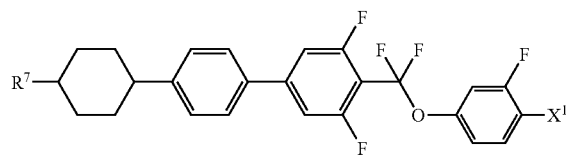
(4-32) 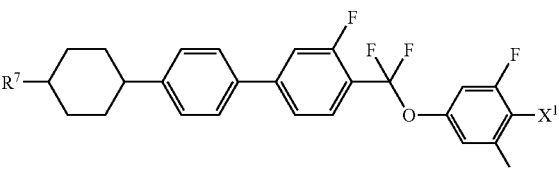
(4-33) 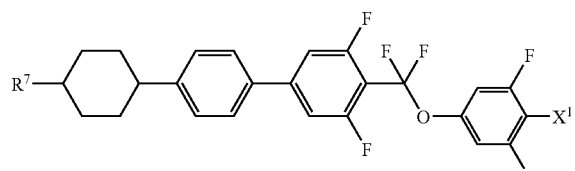
(5-1) 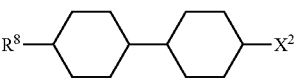
(5-2) 
(5-3) 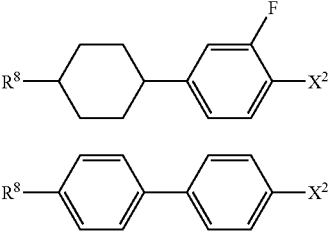
(5-4) 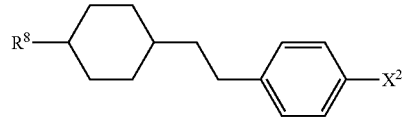
(5-5) 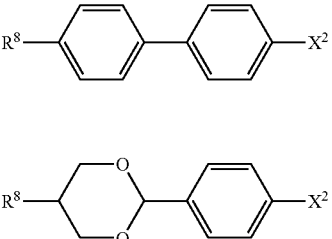
(5-6) 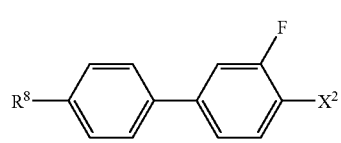
(5-7) 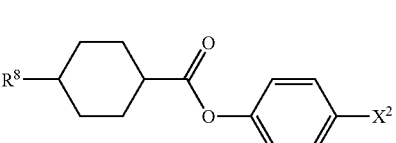
(5-8) 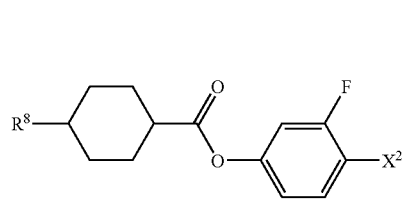
(5-9) 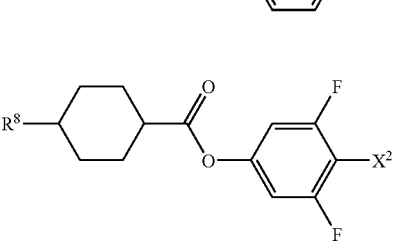
(5-10) 
(5-11)

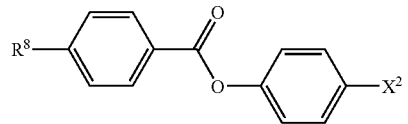
(5-12)
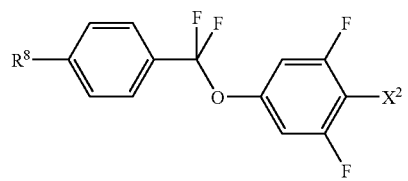
(5-14)
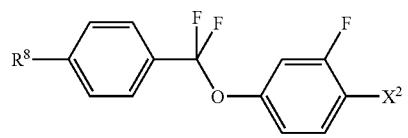
(5-16)
(5-18)
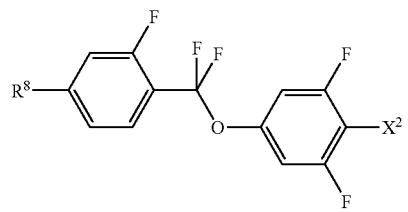
(5-20)
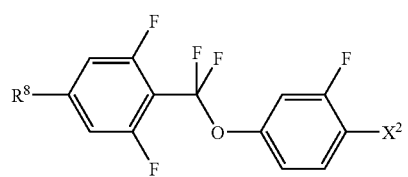
(5-22)
(5-24)
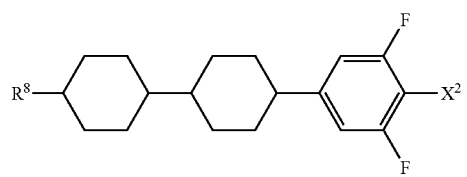
(5-26)
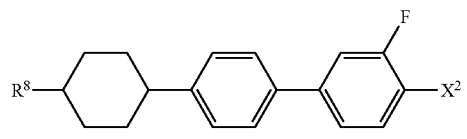
(5-28)
-continued
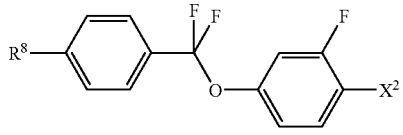
(5-13)
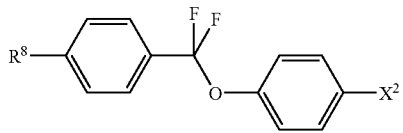
(5-15)
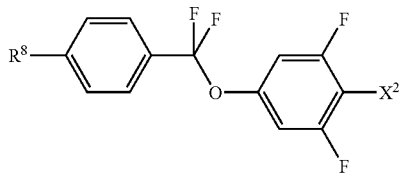
(5-17)
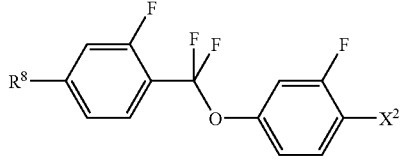
(5-19)
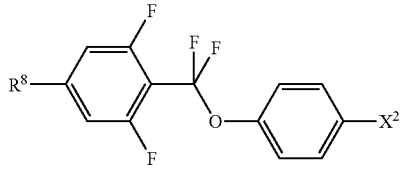
(5-21)
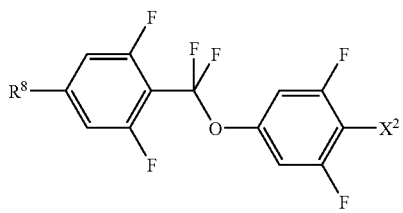
(5-23)
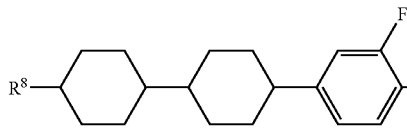
(5-25)
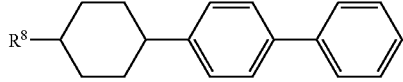
(5-27)
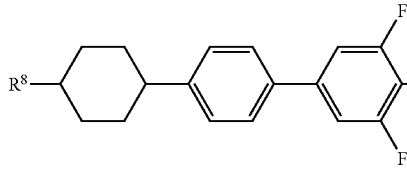
(5-29)

-continued
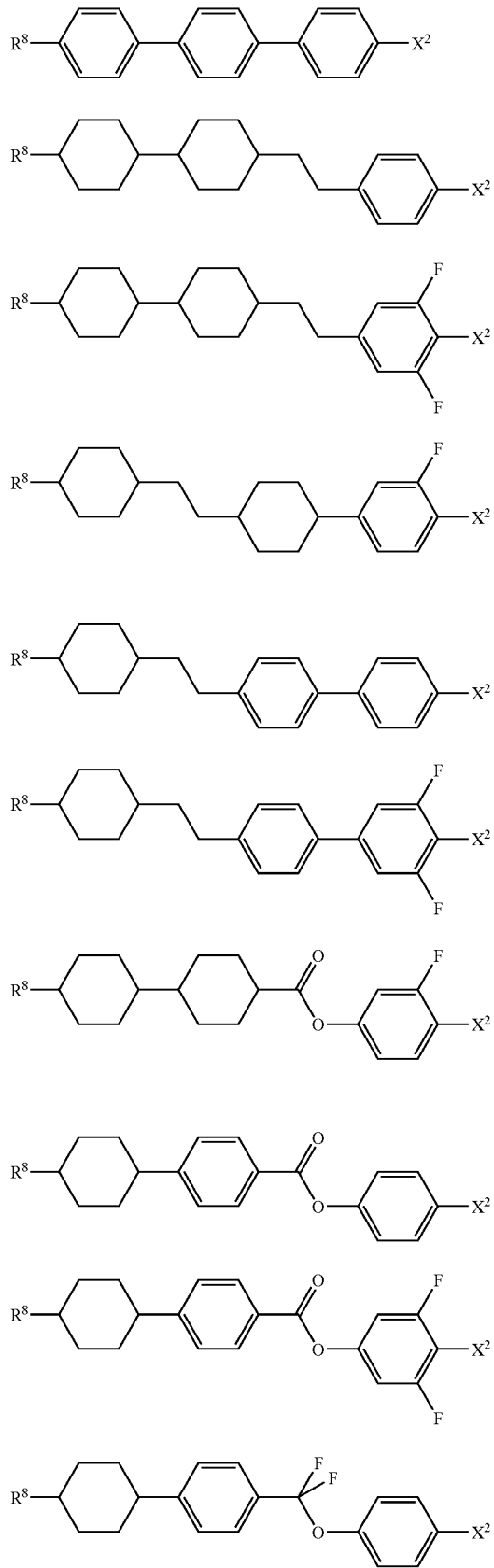
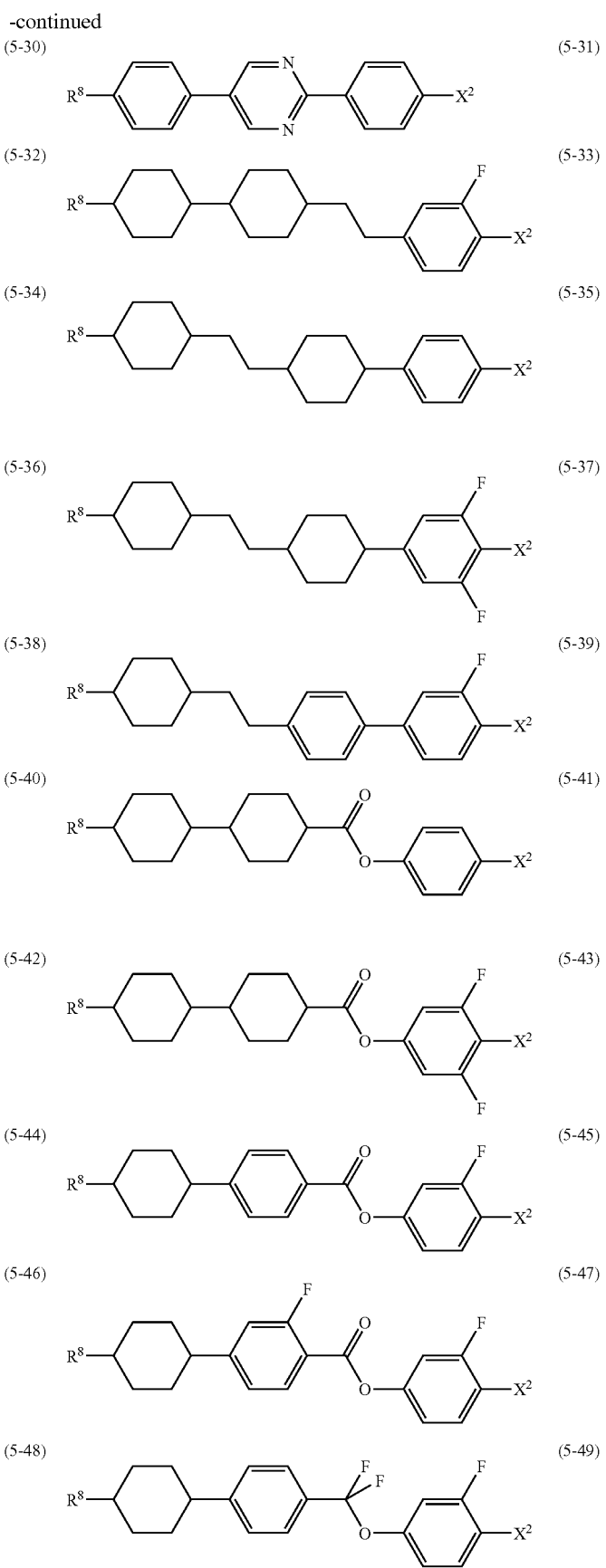

-continued
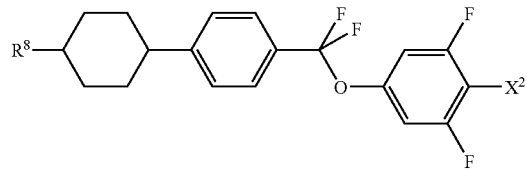 (5-50)
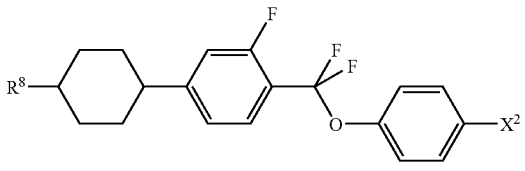 (5-51)
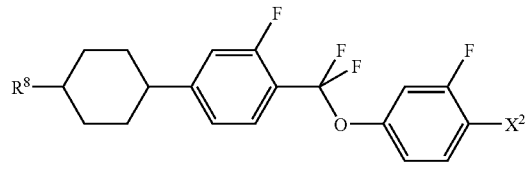 (5-52)
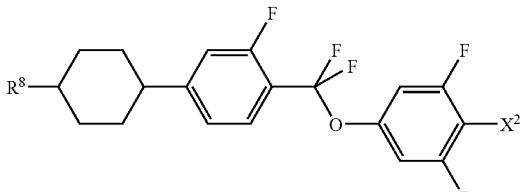 (5-53)
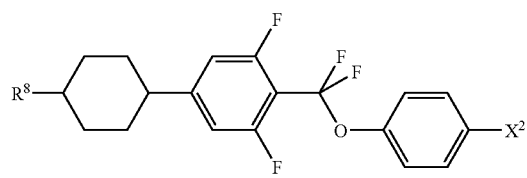 (5-54)
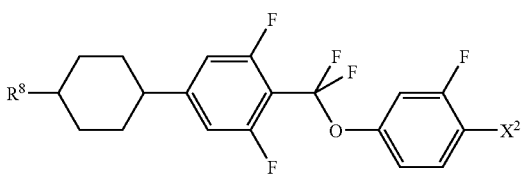 (5-55)
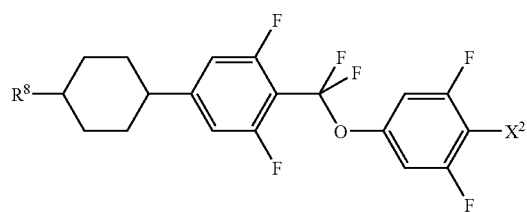 (5-56)
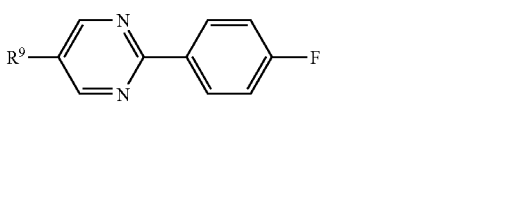 (6-1)
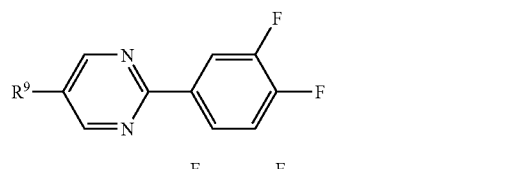 (6-2)
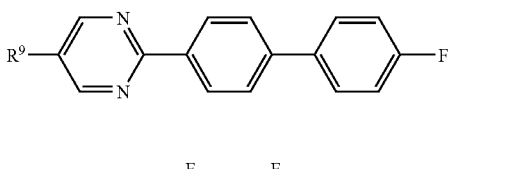 (6-3)
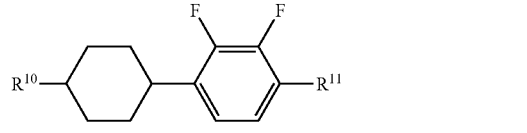 (7-1)
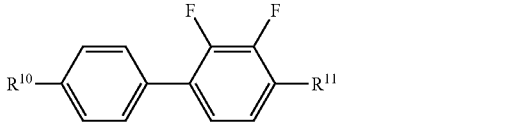 (7-2)
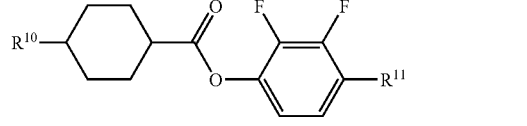 (7-3)
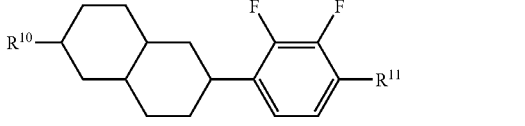 (7-4)
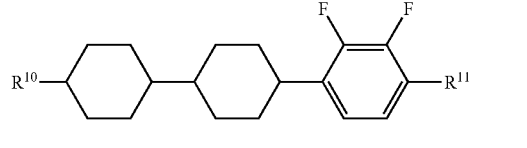 (8-1)
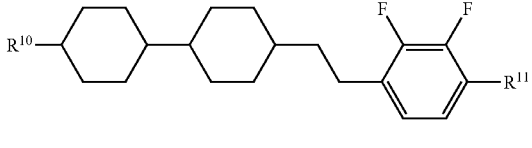 (8-2)
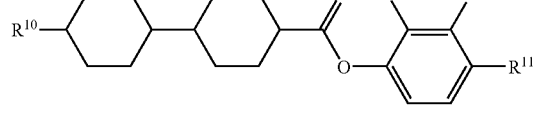 (8-3)
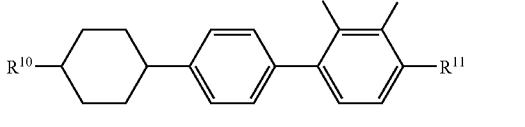 (8-4)
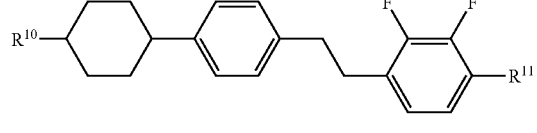 (8-5)
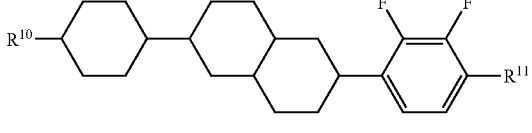 (8-6)

-continued

-continued
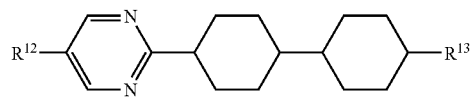 (13-6)
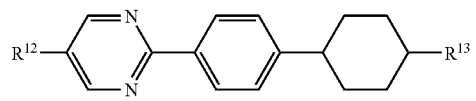 (13-7)
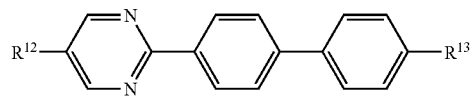 (13-8)
(13-9)
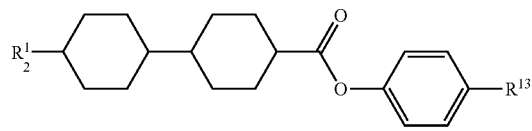 (13-10)
(13-11)
(13-12)
(13-13)
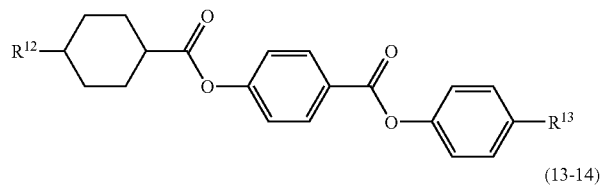 (13-14)
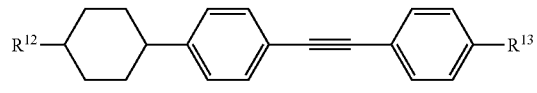 (13-15)
(13-16)
(13-17)
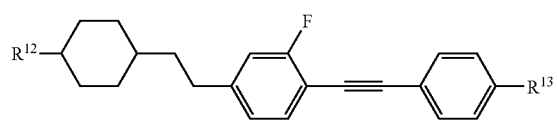 (13-18)
(13-19)
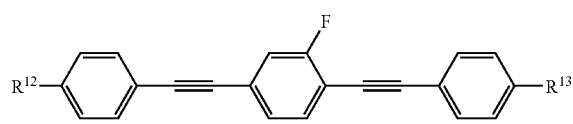 (13-20)
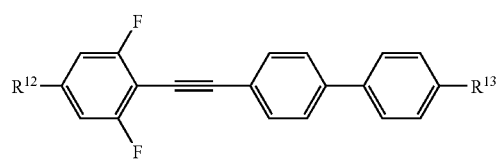 (13-21)
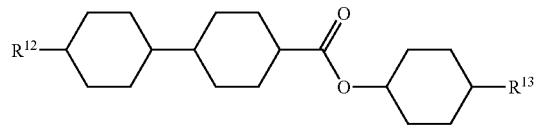 (14-1)
(14-2)
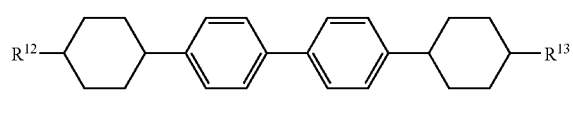 (14-3)
(14-4)
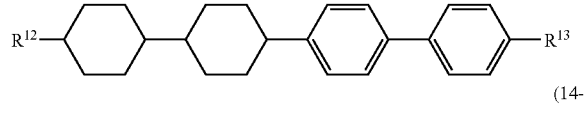 (14-5)
(14-6)
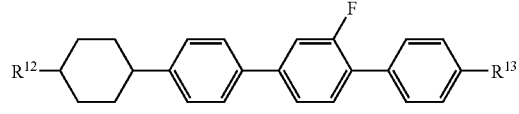
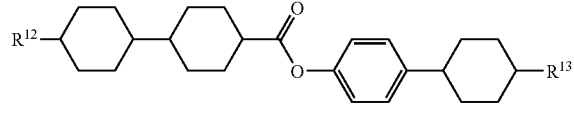

-continued
(Op-1)
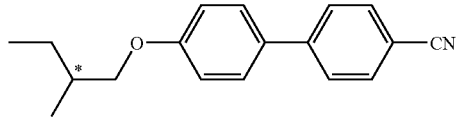
(Op-2)
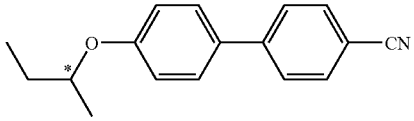
(Op-3)
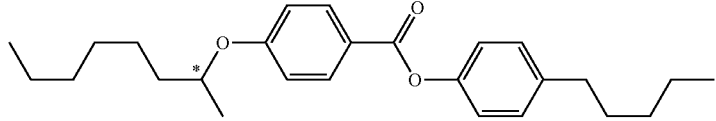
(Op-4)
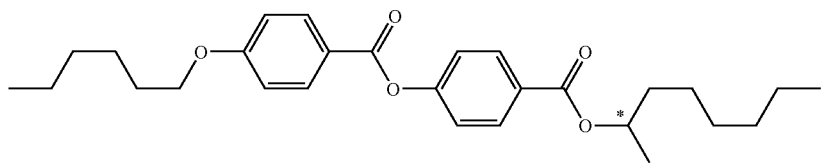
(Op-5)
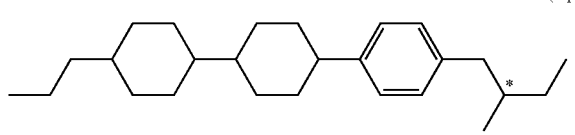
(Op-6)
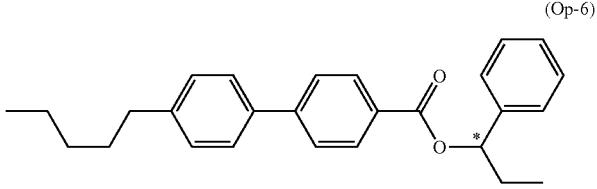
(Op-7)
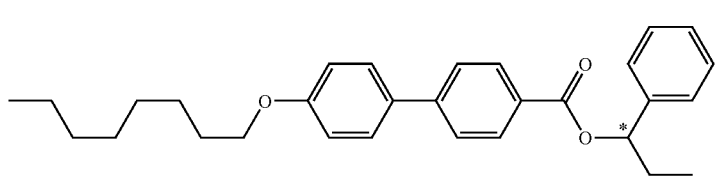
(Op-8)
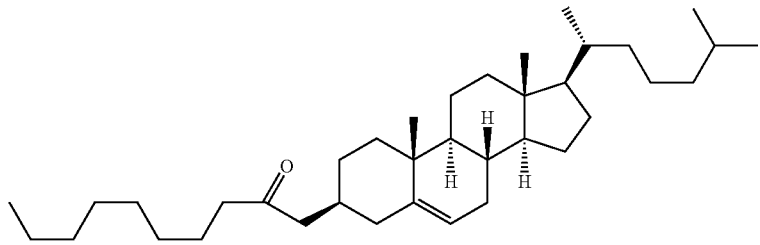
(Op-9)
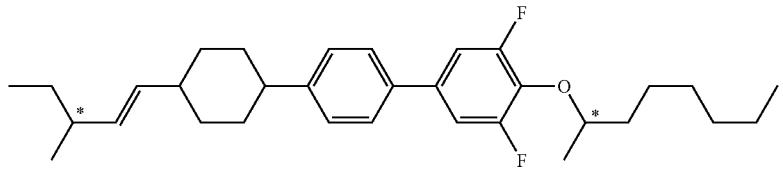
(Op-10)
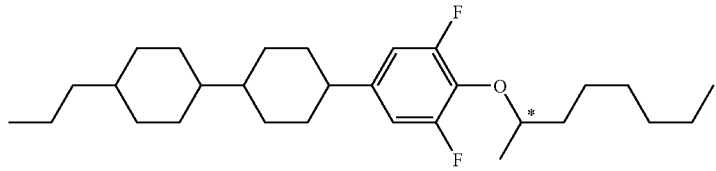
(Op-11)
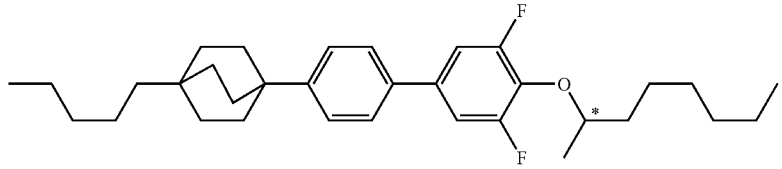

-continued

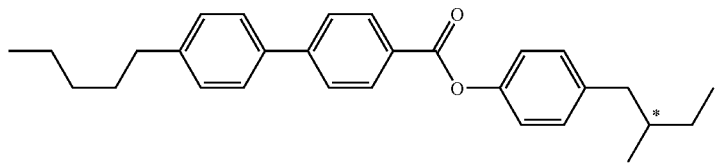
(Op-12)

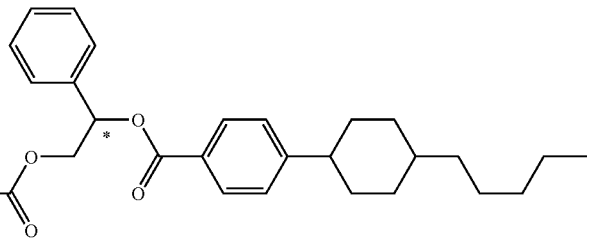
(Op-13)

The composition of the present invention is prepared by a known method. For example, the component compounds are mixed and dissolved by heating. Appropriate additives well known by one skilled in the art may be added to the composition to adjust physical properties of the composition. A dichroic pigment such as melocyanine, styryl, azo, azomethine, azoxy, quinophthalone, anthraquinone and tetrazine may be added to prepare a composition for a GH device. A chiral dopant may be added to offer a twist angle by inducing a spiral structure of the liquid crystal. An example of the chiral dopant is the optically active compounds (Op-1) to (Op-12).

A chiral dopant is added to the composition to adjust the pitch of twist. The pitch of twist for a TN device and a TN-TFT device is preferably in a range of from approximately 40 μm to approximately 200 μm. The pitch of twist for an STN device is preferably in a range of from approximately 6 μm to approximately 20 μm. The pitch of twist for a BTN device is preferably in a range of from approximately 1.5 μm to approximately 4 μm. A relatively large amount of a chiral dopant is added to a composition for a PC device. At least two chiral dopants may be added for adjusting the temperature dependency of the pitch.

The composition of the invention may be used in such devices as PC, TN, STN, BTN, ECB, OCB, IPS and VA devices. The driving mode of the devices may be either PM or AM. The composition may also be used in an NCAP (nematic curvilinear aligned phase) device, which is produced by microencapsulating the composition, and a PD (polymer dispersed) device, which is obtained by forming a three-dimensional network polymer in the composition, such as a PN (polymer network) device.

EXAMPLE

The invention will be further described with reference to the following examples, but the invention is not construed as being limited to the examples. The number of the compound, such as "No. 1", corresponds to the number of the compound shown in the table in Example 5. In the table, the steric configuration of 1,4-cyclohexylene and 1,3-dioxane-2,5-diyl is trans, and the steric configuration of the bonding group —CH=CH— is trans. The number in parentheses following the symbol corresponds to the number of the preferred compound. The symbol (-) means another compound. The proportions (in terms of percentage) of the compounds are in terms of percentage by weight (% by weight) based on the total weight of the composition. The characteristic values of the composition are summarized at the end.

The measurement of the characteristic values was carried out according to the following methods. Most of them are methods described in EIAJ ED-2521A of the Standard of Electric Industrial Association of Japan or methods obtained by modifying them.

A higher limit temperature of a nematic phase (NI; ° C.) A sample was placed on a hot plate in a melting point measuring apparatus equipped with a polarizing microscope and was heated at the rate of 1° C. per minute. A temperature was measured when a part of the sample began to change from a nematic phase into an isotropic liquid. A higher limit temperature of a nematic phase may be abbreviated to "a higher limit temperature".

A lower limit temperature of a nematic phase (Tc; ° C.): A sample having a nematic phase was kept in a freezer at temperatures of 0° C., −10° C., −20° C., −30° C., and −40° C. for ten days, respectively, and a liquid crystal phase was observed. For example, when the sample remained in a nematic phase at −20° C. and the sample changed to crystals or a smectic phase at −30° C., Tc was expressed as ≦−20° C. A lower limit temperature may be abbreviated to "a lower limit temperature".

Optical anisotropy (refractive index anisotropy; Δn; measured at 25° C.): An optical anisotropy was measured by means of an Abbe refractometer having a polarizing plate attached to the eyescope with a light having a wavelength of 589 nm. After rubbing the surface of the main prism in one direction, the sample was dropped on the main prism. The refractive index n∥ was measured when the polarizing direction was in parallel to the rubbing direction. The refractive index n⊥ was measured when the polarizing direction was perpendicular to the rubbing direction. A value of optical anisotropy was calculated from an equation: Δn=n∥−n⊥. In the case where the sample was a composition, the optical anisotropy was measured in the aforementioned manner. In the case where the sample was a compound, the compound was mixed with a suitable composition and then measured for optical anisotropy. The optical anisotropy of the compound is an extrapolation value.

Viscosity (η; mPa·s, measured at 20° C. and −10° C.): A viscosity was measured by means of an E-type viscometer. The value measured at 20° C. is expressed as ($\eta_{20}$), and a value measured at −10° C. is expressed as ($\eta_{-10}$).

Dielectric anisotropy (Δ∈; measured at 25° C.) for a compound having a positive dielectric anisotropy (Δ∈): A sample was poured into a TN device in which the cell gap between two glass plates was 9 μm and the twist angle was 80°. A dielectric constant (∈∥) in the major axis direction of the liquid crystal molecule was measured by applying a voltage of 10 V to the TN device. A dielectric constant (∈⊥) in the minor axis direction of the liquid crystal molecule was measured by applying a voltage of 0.5 V. A value of dielectric anisotropy was calculated from an equation: Δ∈=∈∥−∈⊥. A composition having a positive dielectric anisotropy was measured in the aforementioned manner. In the case where the sample was a compound, the compound was mixed with a suitable composition and then measured for dielectric anisotropy. The dielectric anisotropy of the compound is an extrapolation value.

Dielectric anisotropy (Δ∈; measured at 25° C.) for a compound having a negative dielectric anisotropy (Δ∈): A sample was poured into a VA device in which the cell gap between two glass plates was 20 μm. A dielectric constant (∈∥) in the major axis direction of the liquid crystal molecule was measured by applying a voltage of 0.5 V to the VA device. The sample was poured into a TN device in which the cell gap between two glass plates was 9 μm, and a dielectric constant (∈⊥) in the minor axis direction of the liquid crystal molecule was measured by applying a voltage of 0.5 V to the TN device. A value of dielectric anisotropy was calculated from an equation: Δ∈=∈∥−∈⊥. A composition having a negative dielectric anisotropy was measured in the aforementioned manner. In the case where the sample was a compound, the compound was mixed with a suitable composition and then measured for dielectric anisotropy. The dielectric anisotropy of the compound is an extrapolation value.

Threshold voltage (Vth; measured at 25° C.; V): A sample was poured into a TN device of a normally white mode, in which the cell gap between two glass plates was (0.5/Δn) μm and a twist angle was 80°. Δn is the value of optical anisotropy measured in the aforementioned manner. A rectangular wave having a frequency of 32 Hz was applied to the device. The applied voltage was increased, and a value of voltage at which the transmittance of light passing through the TN device was 90% was measured.

Helical pitch (measured at 25° C.; μm): For the measurement of helical pitch, Cano's wedge-shaped cell method was used. A sample was placed in Cano's wedge-shaped cell and interval (a; unit: μm) of disclination lines observed from the cell was measured. The helical pitch (P) was calculated from the formula P=2×a×tan θ. θ is an angle between two glass plates in the wedge-shaped cell.

Example 1

Synthesis of 2-Ethyl-5-(4-pentylcyclohexyl)tetrahydropyran (Compound No. 1-1-1-1)

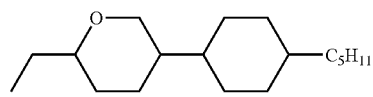

First Step (4-Pentylcyclohexyl)acetaldehyde (30.1 g) was dissolved in diethyl ether (40 mL), to which cyclohexylamine (15.2 g) and potassium carbonate (12 g) were added, and the system was stirred at room temperature over night. The resulting suspension was filtered with Celite, and the filtrate was concentrated under reduced pressure. Cyclohexyl-(2-(4-pentylcyclohexyl)ethylidene)amine (40.6 g) in a yellow oily form thus obtained was used in the second step without purification.

Second Step

Cyclohexyl-(2-(4-pentylcyclohexyl)ethylidene)amine (40.6 g) as a crude product obtained in the first step was dissolved in ethyl acrylate (40 mL), to which hydroquinone (0.6 g) was added, and the system was refluxed under heating at 105° C. for 10 hours. The system was cooled to room temperature, to which THF (500 mL) was added, and a saturated oxalic acid aqueous solution (300 mL) was gradually added, followed by extracting with diethyl ether. An organic layer was washed with water and dried over anhydrous magnesium sulfate, and then it was concentrated under reduced pressure. The resulting brown residue (44.93 g) was purified by silica gel column chromatography to obtain ethyl 5-oxa-4-(4-pentylcyclohexyl)pentanoate (27.4 g) in a yellow oily form.

Third Step

5-Oxa-4-(4-pentylcyclohexyl)pentanoate (27.4 g) obtained in the second step was dissolved in isopropanol (200 mL), to which sodium cyanoborohydride (6.5 g) was added, and the system was stirred at room temperature for 3 hours while the pH was constantly adjusted to about 3 with HCl (2 N). Water (100 mL) was added to the reaction liquid, and the system was extracted with toluene. The organic layer was washed with water and concentrated under reduced pressure. The resulting residue (23.3 g) in orange color was purified by silica gel column chromatography to obtain 5-(4-pentylcyclohexyl)tetrahydropyran-2-one (14.0 g) in a yellow oily form.

Fourth Step

Trimethylsilylacetylene (16.8 mL) was dissolved in THF (300 mL), to which n-butyllithium (1.5 M hexane solution, 74.2 mL) was then added dropwise at −70° C., followed by stirring at that temperature for 1 hour. To the resulting solution, 5-(4-pentylcyclohexyl)tetrahydropyran-2-one (14.0 g) obtained in the third step was added dropwise at −70° C., followed by stirring at that temperature for further 1 hour, and then the temperature of the system was gradually increased to room temperature. The reaction product was poured into 300 mL of a saturated ammonium chloride aqueous solution, followed by extracting with diethyl ether. The organic layer was washed with water and concentrated under reduced pressure. The resulting brown residue (20.2 g) was purified by silica gel column chromatography to obtain 5-(4-pentylcyclohexyl)-2-trimethylsilanylethynyltetrahydro pyran-2-ol (13.9 g) in a brown solid form.

Fifth Step 5-(4-Pentylcyclohexyl)-2-trimethylsilanylethynyltetrahydropyran-2-ol (13.9 g) obtained in the fourth step was dissolved in dichloromethane (150 mL) and acetonitrile (30 mL), to which triethylsilane (11.8 mL) was added dropwise at −50° C., and subsequently boron trifluoride diethyl ether complex (7 mL) was added dropwise. After gradually increasing the temperature of the system to 0° C., the system was poured into 300 mL of iced water, followed by extracting with n-heptane. The organic layer was washed with water and concentrated under reduced pressure. The resulting brown residue (11.0 g) was purified by silica gel column chromatography to obtain 2-ethynyl-5-(4-pentylcyclohexyl)tetrahydropyran (8.9 g) in a yellow oily form.

Sixth Step

2-Ethynyl-5-(4-pentylcyclohexyl)tetrahydropyran (2.9 g) obtained in the fifth step was dissolved in isopropanol (50 mL), to which 0.15 g of a Pd—C catalyst was added. After depressurizing the reaction vessel with a vacuum pump, hydrogen was introduced thereto under ordinary pressure, and the system was stirred at ordinary temperature overnight. The reaction liquid was filtered to remove the catalyst, and then concentrated under reduced pressure. The resulting colorless residue (2.7 g) was purified by silica gel column chromatography to obtain 2-ethyl-5-(4-pentylcyclohexyl)tetrahydropyran (2.4 g) in a colorless oily form. The resulting product was purified by subjecting to recrystallization repeatedly to obtain pure 2-ethyl-5-(4-pentylcyclohexyl)tetrahydropyran (0.5 g).

Example 2

Synthesis of 2-Vinyl-5-(4-pentylcyclohexyl)tetrahydropyran (Compound No. 1-1-1-4)

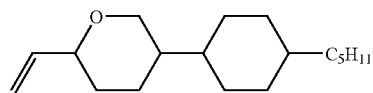

2-Ethynyl-5-(4-pentylcyclohexyl)tetrahydropyran (2.7 g) obtained in the fifth step of Example 1 was dissolved in n-heptane (30 mL), to which quinoline (0.4 mL) and 0.04 g of a Lindlar catalyst were added. After depressurizing the reaction vessel with a vacuum pump, hydrogen was introduced thereto under ordinary pressure, and the system was stirred at ordinary temperature for 90 minutes. The reaction liquid was filtered to remove the catalyst, and then concentrated under reduced pressure. The resulting light yellow residue (2.5 g) was purified by silica gel column chromatography to obtain 2-vinyl-5-(4-pentylcyclohexyl)tetrahydropyran (2.2 g) in a colorless oily form. The resulting product was purified by subjecting to recrystallization repeatedly to obtain pure 2-vinyl-5-(4-pentylcyclohexyl)tetrahydropyran (1.2 g).

Example 3

Synthesis of 2-Vinyl-5-(4-pentylcyclohexyl)tetrahydropyran (Compound No. 1-1-1-5)

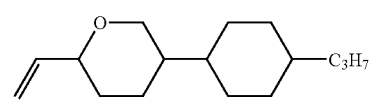

2-Vinyl-S-(4-pentylcyclohexyl)tetrahydropyran was synthesized same as example 1 in place of (4-pentylcyclohexyl)acetaldehyde making use of (4-propylcyclohexyl)acetaldehyde.

Example 4

Synthesis of 2-Ethyl-S-(4'-propyl-bicyclohexyl-4-yl)tetrahydropyran (Compound No. 1-4-1-2)

2-Ethyl-5-(4'-propyl-bicyclohexyl-4-yl)tetrahydropyran was synthesized same as example 1 in place of (4-pentylcyclohexyl)acetaldehyde making use of (4'-Propyl-bicyclohexyl-4-yl)acetaldehyde.

Example 5

Synthesis of 5-(4'-Propyl-bicyclohexyl-4-yl)-2-vinyl-tetrahydropyran (Compound No. 1-4-1-6)

5-(4'-Propyl-bicyclohexyl-4-yl)-2-vinyl-tetrahydropyran was synthesized same as example 2 in place of (4-pentylcyclohexyl)acetaldehyde making use of (4'-Propyl-bicyclohexyl-4-yl)acetaldehyde.

Example 6

Synthesis of 2-Propyl-5-(4'-vinyl-bicyclohexyl-4-yl)tetrahydropyran (Compound No. 1-4-1-4)

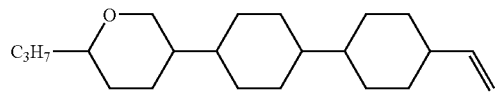

First Step

Methoxymethyltryphenylphosphonium chloride (17.9 g) was suspended in THF (150 mL), to which THF solution (150 mL) of potassium tert-butoxide was then added dropwise at −20° C., followed by stirring at that temperature for 0.5 hour. To the resulting mixture, THF solution (100 mL) of 4'-Vinyl-bicyclohexyl-4-carbaldehyde (9.0 g) was added dropwise at −20° C., followed by stirring at that temperature for further 1 hour, and then the temperature of the system was gradually increased to room temperature. To the resulting solution, water (300 mL) was added, followed by extracting with toluene. The organic layer was washed with water and concentrated in about 300 mL under reduced pressure, and then the resulting solution was poured into 1000 mL of n-heptane with vigorous stirring. The resulting suspension was filtered under reduced pressure, and then the filtrate was concentrated under reduced pressure. The resulting colorless yellow residue was purified by silica gel column chromatography to obtain 4-(2-methoxy-vinyl)-4'-vinylbicyclohexyl (8.9 g) in a colorless yellow oily form.

Second Step 4-(2-methoxy-vinyl)-4'-vinylbicyclohexyl (8.9 g) obtained in the first step was dissolved in acetone (100 mL), to which 6 mL of HCl (2N) was added, and the system was stirred at room temperature for 2 hour. To the resulting solution, water (100 mL) was added, followed by extracting with toluene. The organic layer was washed with water and concentrated under reduced pressure. The resulting colorless yellow residue was purified by silica gel column chromatography to obtain (4'-vinylbicyclohexyl-4-yl)acetaldehyde (8.2 g) in a colorless yellow oily form.

Third Step (4'-vinylbicyclohexyl-4-yl)acetaldehyde (8.2 g) obtained in the second step was dissolved in THF (100 mL), to which cyclohexylamine (3.5 g) and calcium carbonate (3.0 g) was added, and the system was stirred at room temperature overnight. The resulting suspension was filtered with Celite, and the filtrate was concentrated under reduced pressure. Cyclohexyl-(2-(4'-vinylcyclohexyl-4-yl)ethylidene)amine (11.3 g) in a yellow oily form thus obtained was used in the second step without purification.

Fourth Step

Cyclohexyl-(2-(4'-vinylcyclohexyl-4-yl)ethylidene) amine (11.3 g) as a crude product obtained in the Third step was dissolved in ethyl acrylate (20 mL), to which hydroquinone (0.2 g) was added, and the system was refluxed under heating at 110° C. for 15 hours. The system was cooled to room temperature, to which THF (50 mL) was added, and a saturated oxalic acid aqueous solution (100 mL) was gradually added, followed by extracting with diethyl ether. An organic layer was washed with water and dried over anhydrous magnesium sulfate, and then it was concentrated under reduced pressure. The resulting brown residue (11.9 g) was purified by silica gel column chromatography to obtain ethyl 5-oxa-4-(4'-vinylcyclohexyl-4-yl)pentanoate (7.8 g) in a colorless solid form.

Fifth Step 5-oxa-4-(4'-vinylcyclohexyl-4-yl)pentanoate (7.8 g) obtained in the fourth step was dissolved in isopropanol (40 mL), to which sodium cyanoborohydride (1.2 g) was added, and the system was stirred at room temperature for 3 hours while the pH was constantly adjusted to about 3 with HCl (2 N). Water (100 mL) was added to the reaction liquid, and the system was extracted with toluene. The organic layer was washed with water and concentrated under reduced pressure. The resulting colorless residue (7.3 g) was purified by silica gel column chromatography to obtain 5-(4-vinyl-bicyclohexyl-4-yl)tetrahydropyran-2-one (6.0 g) in a colorless oily form.

Sixth Step

Lithium wire (0.85 g) which is carved finely was added to the THF (50 mL), to which THF solution (30 mL) of 1-bromopropane (7.4 g) was then added dropwise slowly at room temperature in order for the reaction liquid to reflux loosely, followed by stirring at that temperature for 1 hour. The resulting mixture was put in place gently, the skim was used for the following reaction. THF solution of 5-(4-vinyl-bicyclohexyl-4-yl)tetrahydropyran-2-one (6.0 g) obtained in the fifth step was thrown to another reactor, to which the skim which is obtained some time ago was added dropwise at −70° C., followed by stirring at that temperature for 1 hour, and then the temperature of the system was gradually increased to room temperature. The reaction product was poured into 100 mL of a saturated ammonium chloride aqueous solution, followed by extracting with diethyl ether. The organic layer was washed with water and concentrated under reduced pressure. The resulting white residue (5.4 g) was purified by silica gel column chromatography to obtain 2-propyl-5-(4'-vinyl-cyclohexyl-4-yl)-2-tetrahydropyran-2-o 1 (1.8 g) in a white solid form.

Seventh Step 2-propyl-5-(4'-vinylcyclohexyl-4-yl)-2-tetrahydropyran-2-ol (1.8 g) obtained in the sixth step was dissolved in dichloromethane (50 mL) and acetonitrile (10 mL), to which triethylsilane (1.5 mL) was added dropwise at −50° C., and subsequently boron trifluoride diethyl ether complex (0.9 mL) was added dropwise. After gradually increasing the temperature of the system to 0° C., the system was poured into 50 mL of iced water, followed by extracting with diethyl ether. The organic layer was washed with water and concentrated under reduced pressure. The resulting white residue (1.8 g) was purified by silica gel column chromatography to obtain 2-propyl-5-(4'-vinylcyclohexyl-4-yl)tetrahydropyran (1.4 g) in a white solid form. The resulting product was purified by subjecting to recrystallization repeatedly to obtain pure 2-propyl-5-(4'-vinylcyclohexyl-4-yl)tetrahydropyran (0.6 g).

Example 7

Synthesis of 2-(2-(4-Ethylcyclohexyl)ethyl)-5-(4-pentylcyclohexyl)tetrahydropyran (Compound No. 1-5-1-10)

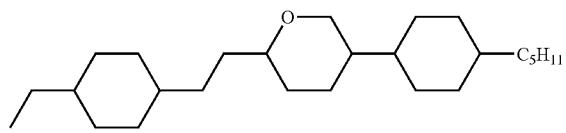

First Step

1-Ethyl-4-ethynylcyclohexane (3.5 g) was dissolved in THF (100 mL), to which n-butyllithium (1.5 M hexane solution, 16.0 mL) was then added dropwise at −70° C., followed by stirring at that temperature for 1 hour. To the resulting solution, 5-(4-pentylcyclohexyl)tetrahydropyran-2-one (5.4 g) obtained in the third step of Example 1 was added dropwise at −70° C., followed by stirring at that temperature for further 1 hour, and then the temperature of the system was gradually increased to room temperature. The reaction product was poured into 100 mL of a saturated ammonium chloride aqueous solution, followed by extracting with diethyl ether. The organic layer was washed with water and concentrated under reduced pressure. The resulting brown residue (7.9 g) was purified by silica gel column chromatography to obtain 2-(4-ethylhexylethynyl)-5-(4-pentylcyclohexyl)tetrahydropyran-2-ol (7.4 g) in a brown solid form.

Second Step 2-(4-Ethylhexylethynyl)-5-(4-pentylcyclohexyl)tetrahydropyran-2-ol (7.4 g) obtained in the first step was dissolved in dichloromethane (50 mL) and acetonitrile (10 mL), to which triethylsilane (5.4 mL) was added dropwise at −50° C., and subsequently boron trifluoride diethyl ether complex (3.2 mL) was added dropwise. After gradually increasing the temperature of the system to 0° C., the system was poured into 50 mL of iced water, followed by extracting with n-heptane. The organic layer was washed with water and concentrated under reduced pressure. The resulting brown residue (7.2 g) was purified by silica gel column chromatography to obtain 2-(4- ethylcyclohexylethynyl)-5-(4-pentylcyclohexyl)tetrahydropyran (6.6 g) in a yellow oily form.

Third Step 2-(4-Ethylcyclohexylethynyl)-5-(4-pentylcyclohexyl)tetrahydropyran (3.0 g) obtained in the second step was dissolved in n-heptane (30 mL), to which 0.15 g of a Pd—C catalyst was added. After depressurizing the reaction vessel with a vacuum pump, hydrogen was introduced thereto under ordinary pressure, and the system was stirred at ordinary temperature over night. The reaction liquid was filtered to remove the catalyst, and then concentrated under reduced pressure. The resulting light yellow residue (2.8 g) was purified by silica gel column chromatography to obtain 2-(2-(4-ethylcyclohexyl)ethyl)-5-(4-pentylcyclohexyl)tetrahydropyran (2.5 g) in a colorless solid form. The resulting product was purified by subjecting to recrystallization repeatedly to obtain pure 2-(2-(4-ethylcyclohexyl)ethyl)-5-(4-pentylcyclohexyl)tetrahydropyran (1.5 g).

Example 8

Synthesis of 2-(2-(4-Ethylcyclohexyl)vinyl-5-(4-pentylcyclohexyl)tetrahydropyran (Compound No. 1-5-1-19)

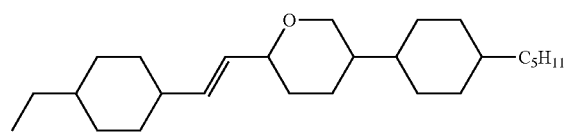

2-(4-Ethylcyclohexylethynyl)-5-(4-pentylcyclohexyl)tetrahydropyran (3.6 g) obtained in the second step of Example 3 was dissolved in diethyl ether (10 mL) and ethanol (10 mL). The system was cooled with a Dewar cooling vessel having a dry-ice/methanol cooling medium, and dried ammonia gas was introduced into the system to accumulate about 100 mL of liquid ammonia therein, to which 0.7 g of lithium was gradually added. After stirring for 3 hours, 50 g of ammonium chloride was added, and the system was taken out from the Dewar cooling vessel to remove ammonia from the system under a nitrogen stream. 100 mL of a saturated ammonium chloride aqueous solution was added to the resulting residue, followed by extracting with dichloromethane. The organic layer was washed with water and concentrated under reduced pressure. The resulting yellow residue (3.3 g) was purified by silica gel column chromatography to obtain 2-(2-(4-ethylcyclohexyl)vinyl)-5-(4-pentylcyclohexyl)tetrahydropyran (2.9 g) in a colorless solid form. The resulting product was purified by subjecting to recrystallization repeatedly to obtain pure 2-(2-(4-ethylcyclohexyl)vinyl)-5-(4-pentylcyclohexyl)tetrahydropyran (1.8 g).

Example 9

The following Compounds Nos. 1-1-1-1 to 1-6-3-27 were synthesized based on Examples 1 to 4 and the disclosed synthesis methods. The compound obtained in Examples 1 to 4 (Compounds Nos. 1-1-1-1, 1-1-1-4, 1-5-1-10 and 1-5-1-19) are also listed below.

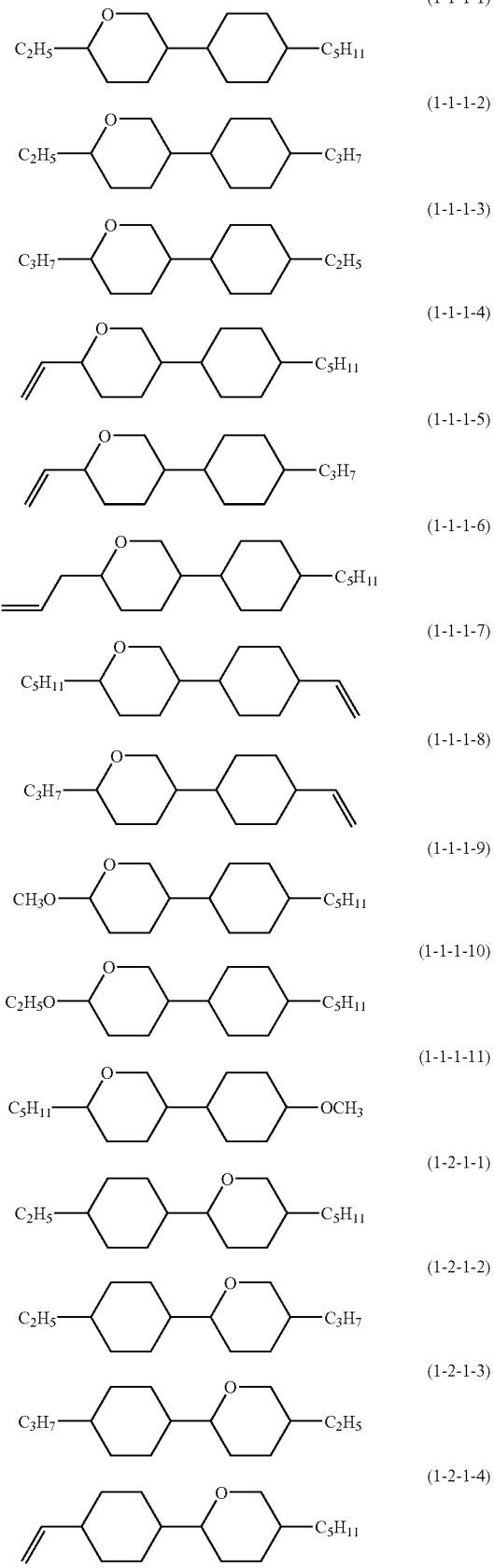

-continued
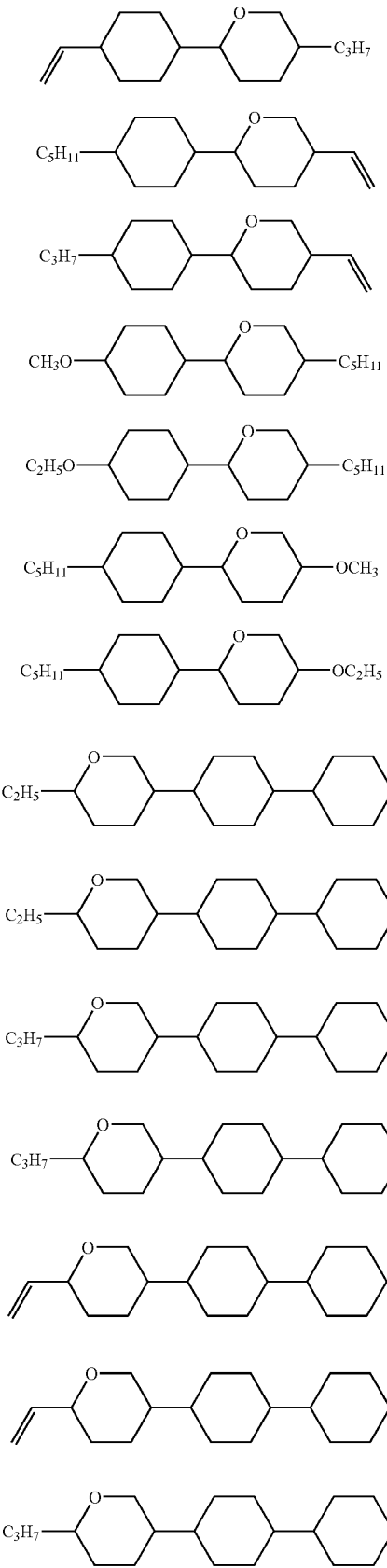
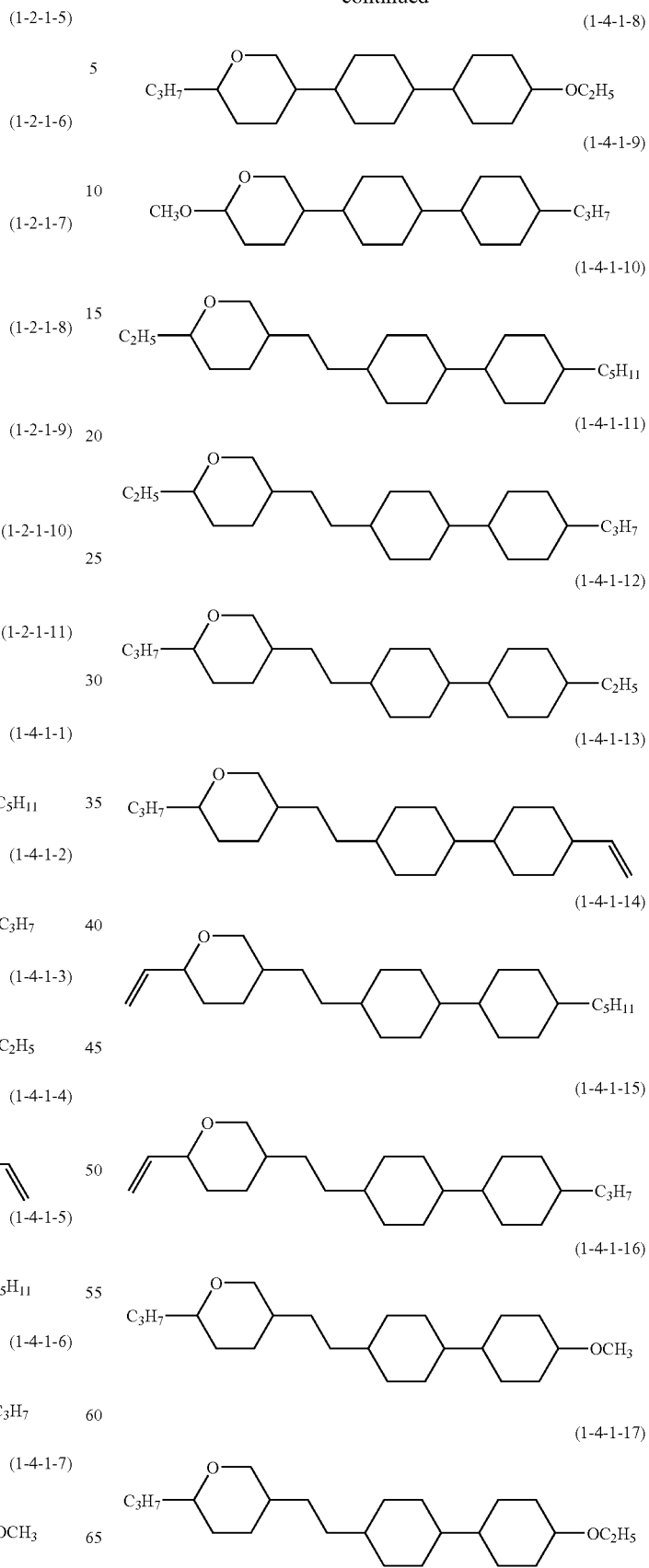

-continued
(1-4-1-18)
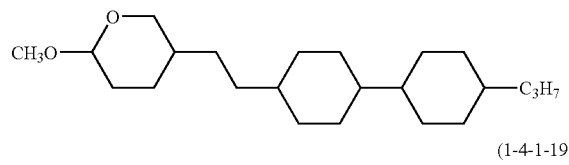
(1-4-1-19)
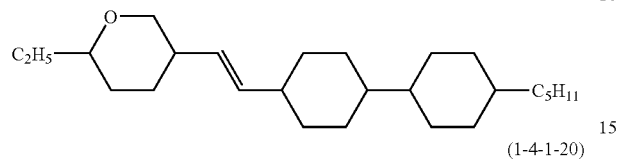
(1-4-1-20)
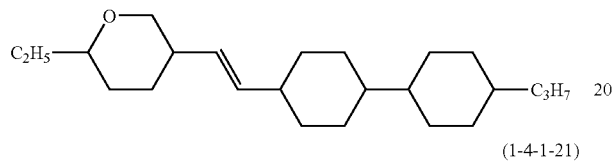
(1-4-1-21)
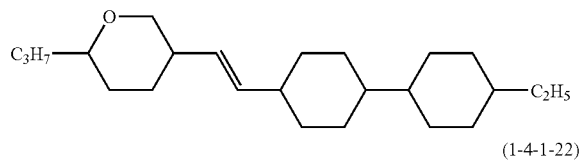
(1-4-1-22)
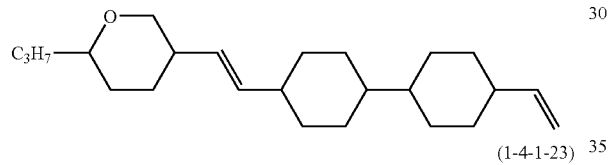
(1-4-1-23)
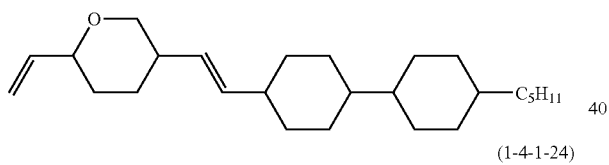
(1-4-1-24)
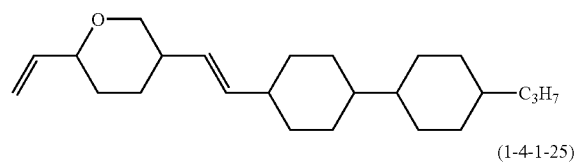
(1-4-1-25)
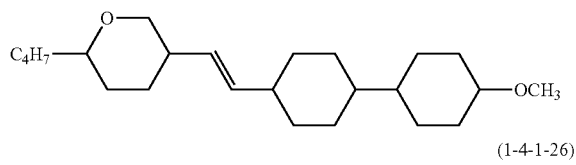
(1-4-1-26)
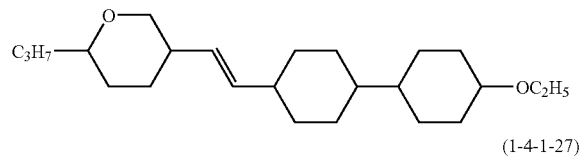
(1-4-1-27)
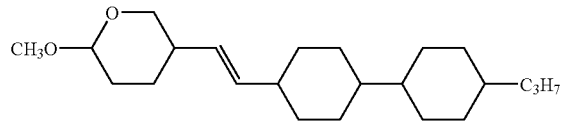
-continued
(1-4-1-28)
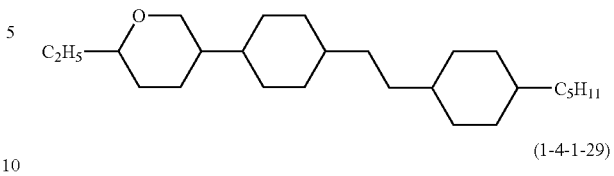
(1-4-1-29)
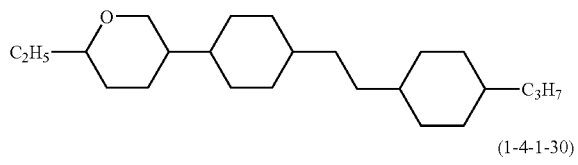
(1-4-1-30)
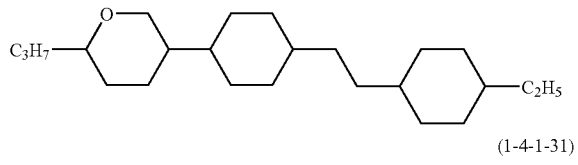
(1-4-1-31)
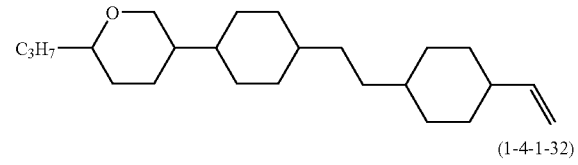
(1-4-1-32)
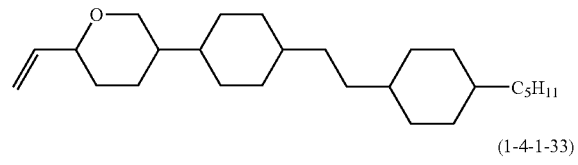
(1-4-1-33)
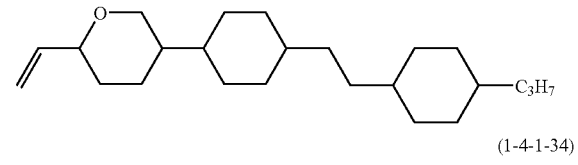
(1-4-1-34)
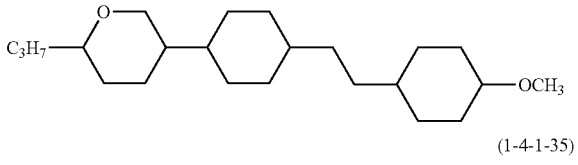
(1-4-1-35)
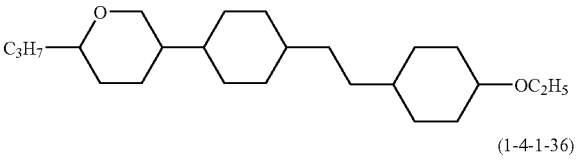
(1-4-1-36)
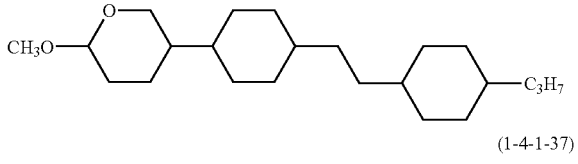
(1-4-1-37)
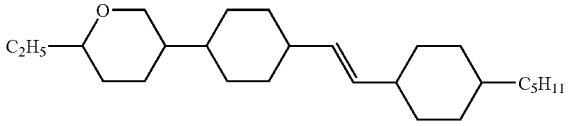

-continued
(1-4-1-38)
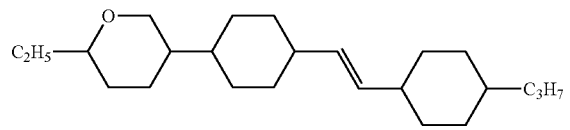
(1-4-1-39)
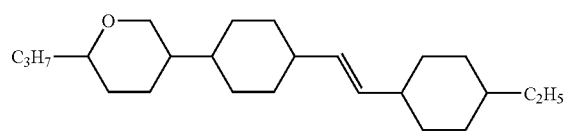
(1-4-1-40)
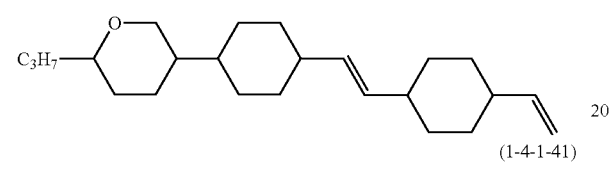
(1-4-1-41)
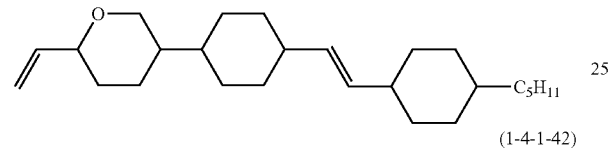
(1-4-1-42)
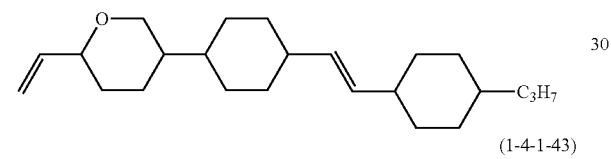
(1-4-1-43)
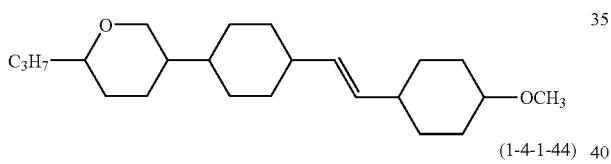
(1-4-1-44)
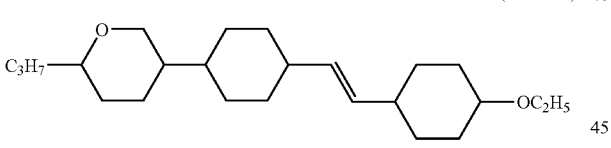
(1-4-1-45)
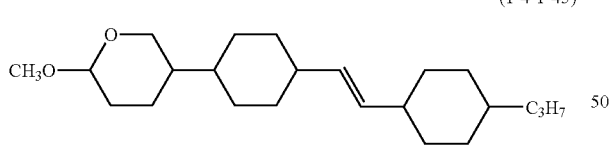
(1-4-2-1)
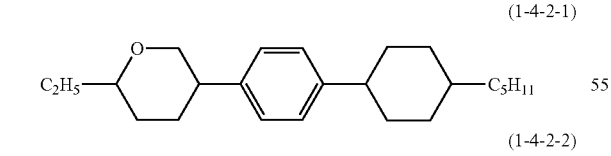
(1-4-2-2)
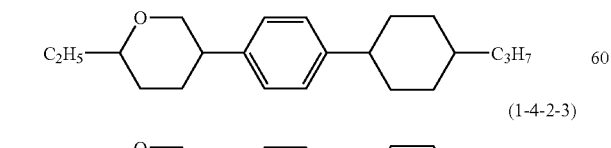
(1-4-2-3)
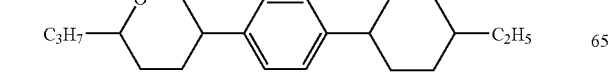
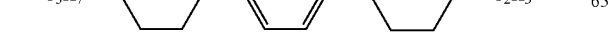
-continued
(1-4-2-4)
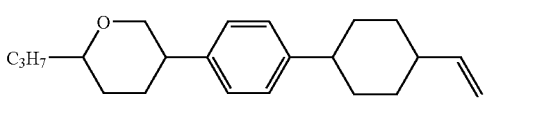
(1-4-2-5)
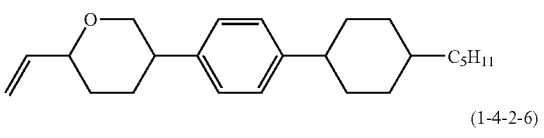
(1-4-2-6)
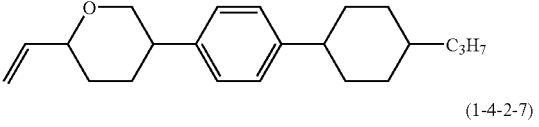
(1-4-2-7)
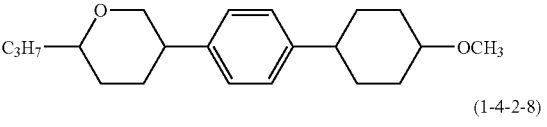
(1-4-2-8)
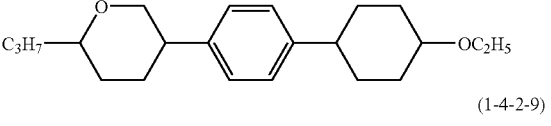
(1-4-2-9)
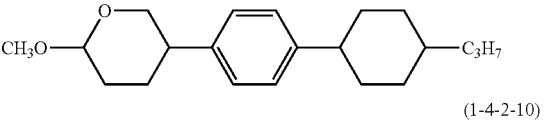
(1-4-2-10)
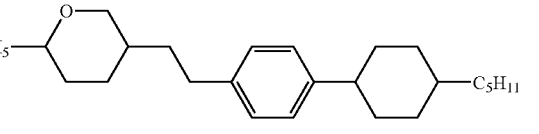
(1-4-2-11)
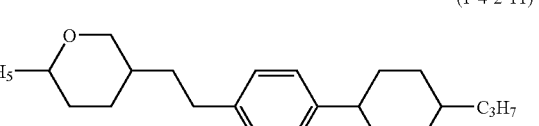
(1-4-2-12)
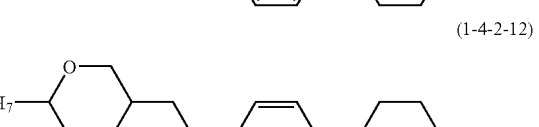
(1-4-2-13)
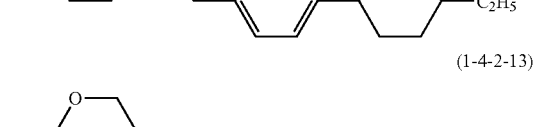
(1-4-2-14)
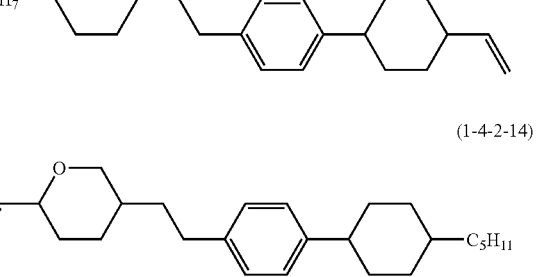

-continued

-continued
(1-4-3-10)
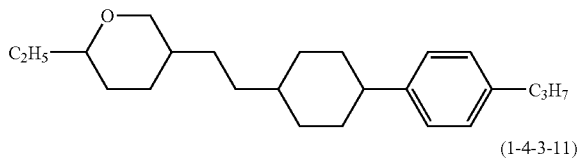
(1-4-3-11)
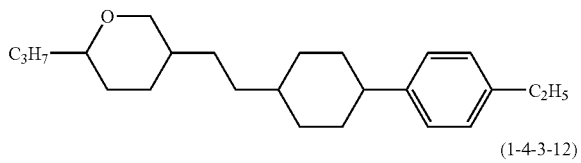
(1-4-3-12)
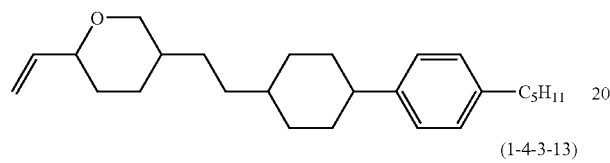
(1-4-3-13)
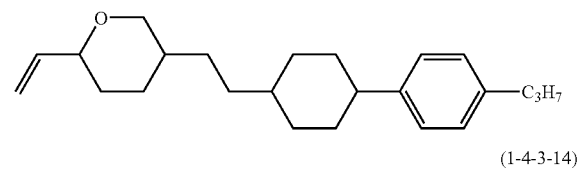
(1-4-3-14)
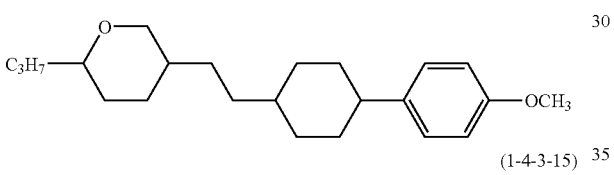
(1-4-3-15)
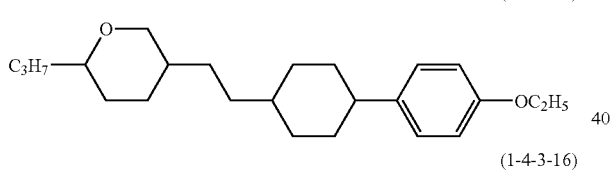
(1-4-3-16)
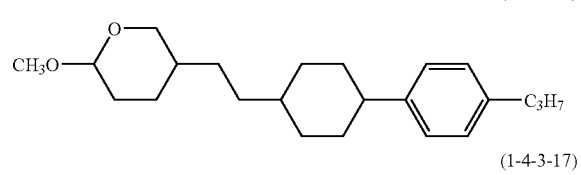
(1-4-3-17)
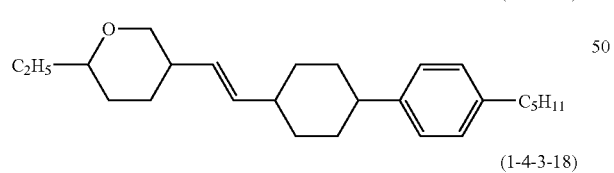
(1-4-3-18)
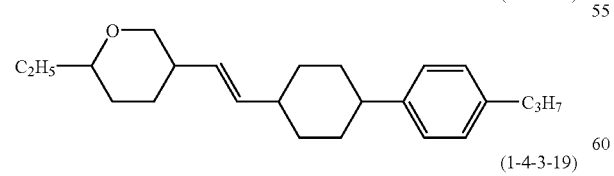
(1-4-3-19)
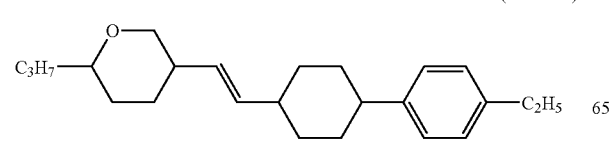
-continued
(1-4-3-20)
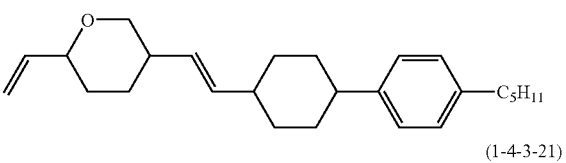
(1-4-3-21)
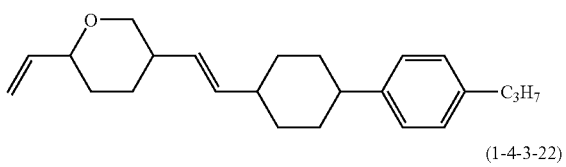
(1-4-3-22)
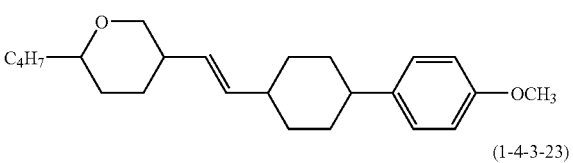
(1-4-3-23)
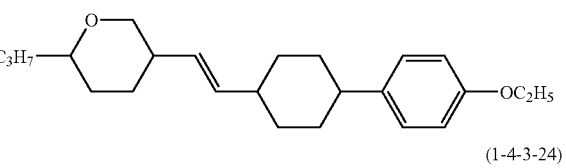
(1-4-3-24)
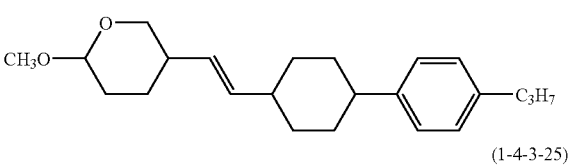
(1-4-3-25)
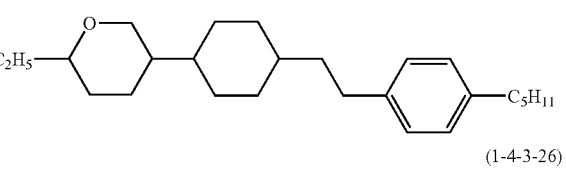
(1-4-3-26)
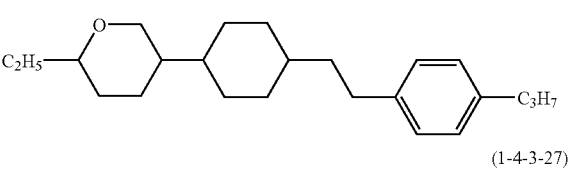
(1-4-3-27)
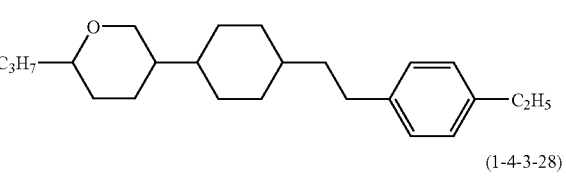
(1-4-3-28)
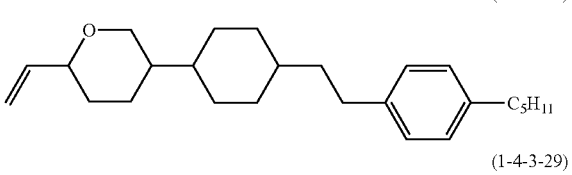
(1-4-3-29)
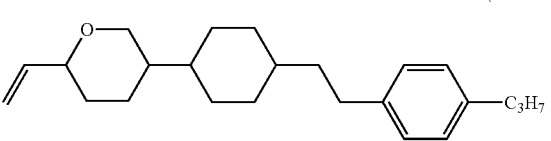

-continued
(1-4-3-30)
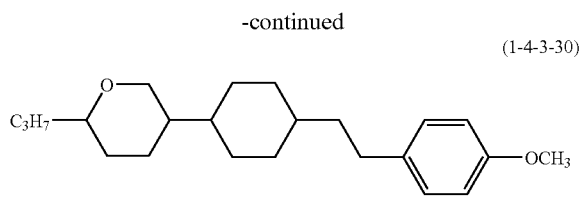
(1-4-3-31)
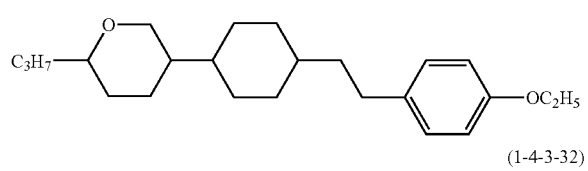
(1-4-3-32)
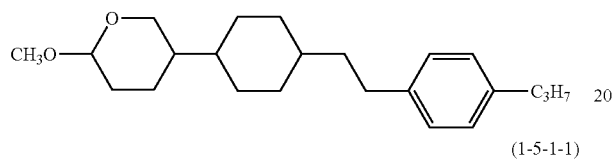
(1-5-1-1)
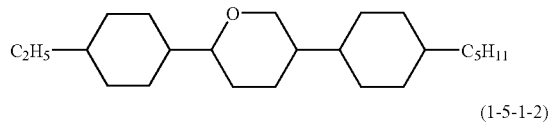
(1-5-1-2)
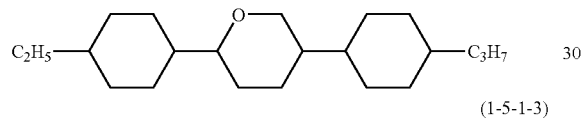
(1-5-1-3)
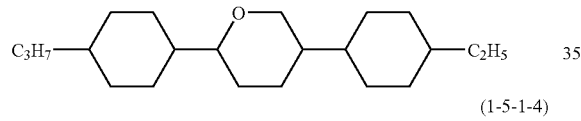
(1-5-1-4)
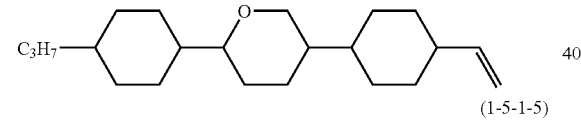
(1-5-1-5)
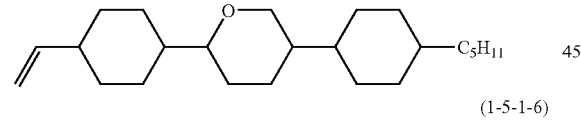
(1-5-1-6)
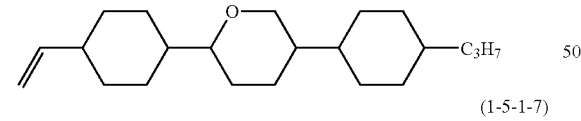
(1-5-1-7)
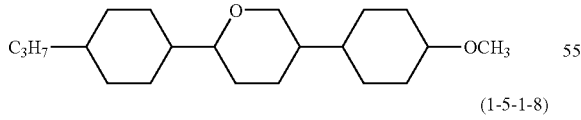
(1-5-1-8)
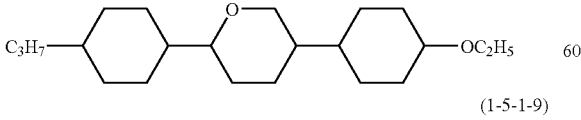
(1-5-1-9)
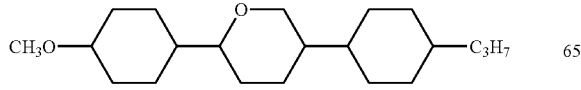
-continued
(1-5-1-10)
(1-5-1-11)
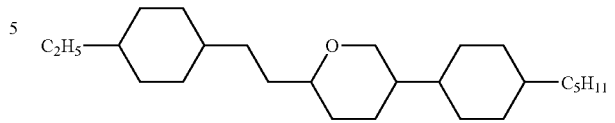
(1-5-1-12)
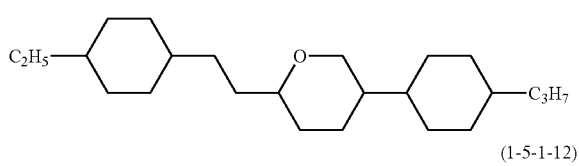
(1-5-1-13)
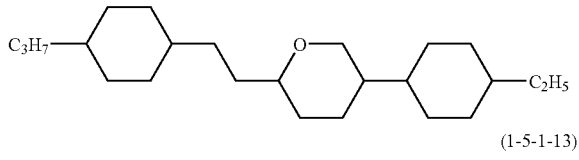
(1-5-1-14)
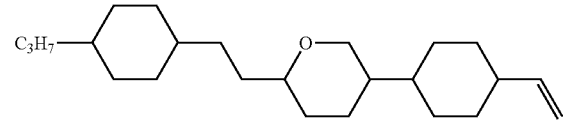
(1-5-1-15)
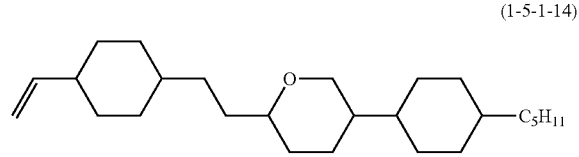
(1-5-1-16)
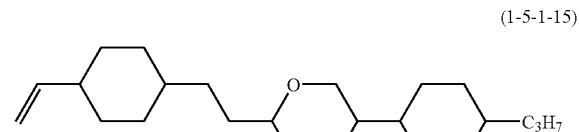
(1-5-1-17)
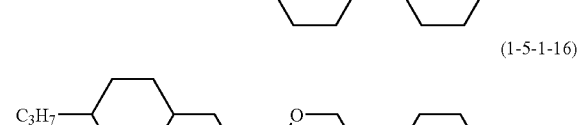
(1-5-1-18)
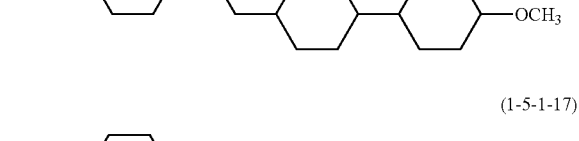
(1-5-1-19)
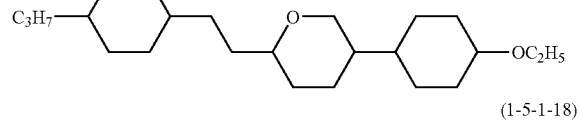
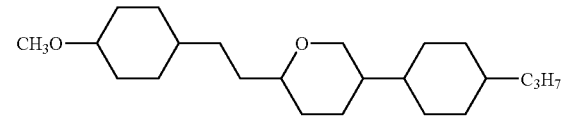

(1-5-1-21)
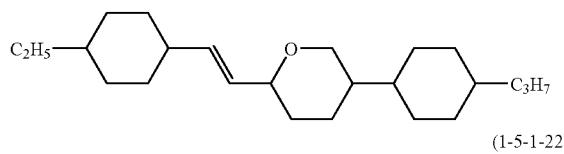
(1-5-1-22)
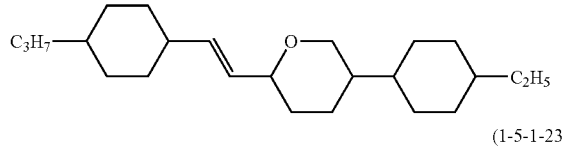
(1-5-1-23)
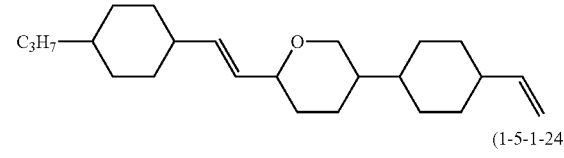
(1-5-1-24)
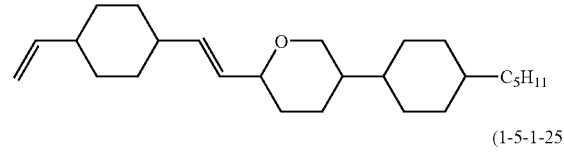
(1-5-1-25)
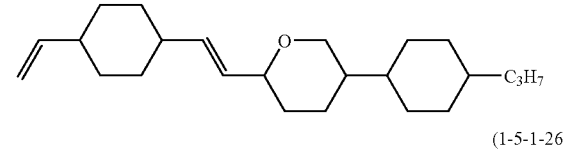
(1-5-1-26)
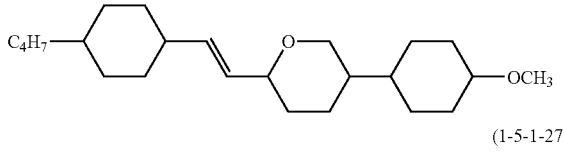
(1-5-1-27)
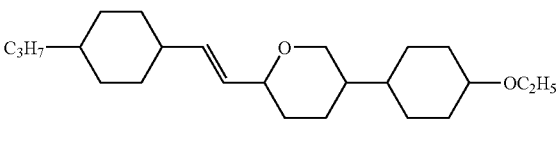
(1-5-1-28)
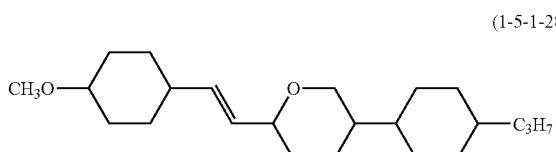
(1-5-1-29)
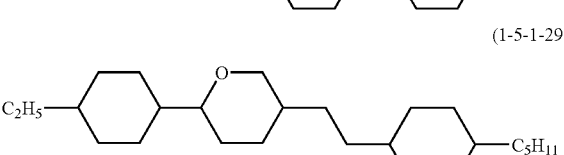
(1-5-1-30)
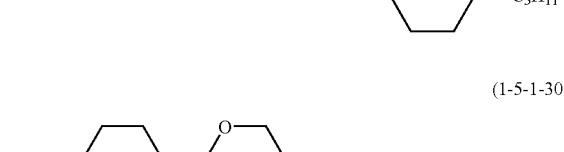
(1-5-1-31)
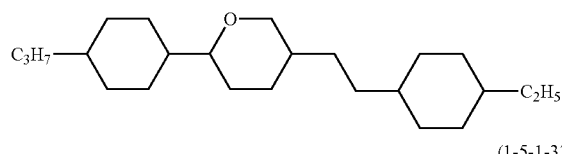
(1-5-1-32)
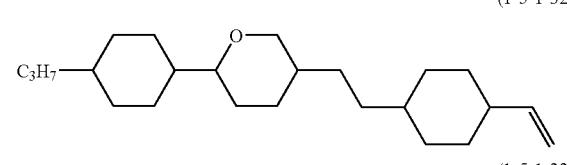
(1-5-1-33)
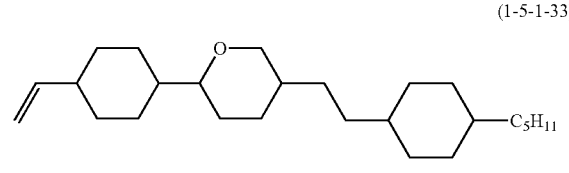
(1-5-1-34)
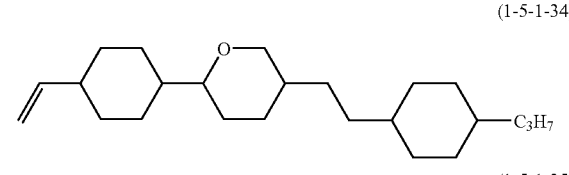
(1-5-1-35)
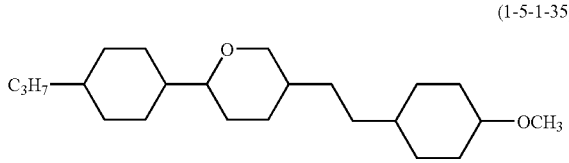
(1-5-1-36)
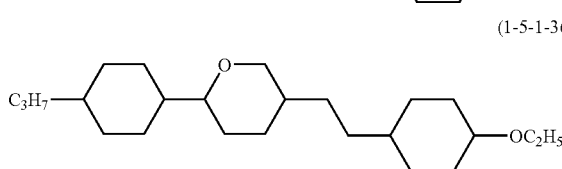
(1-5-1-37)
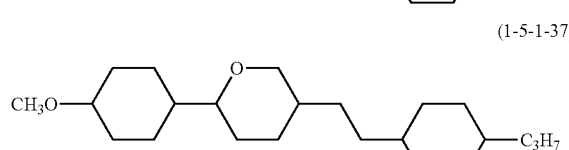
(1-5-1-38)
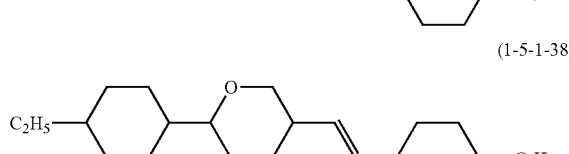
(1-5-1-39)
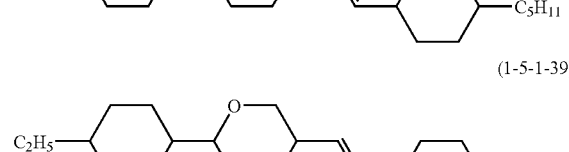
(1-5-1-40)
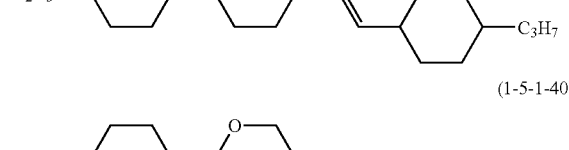

(1-5-1-41) 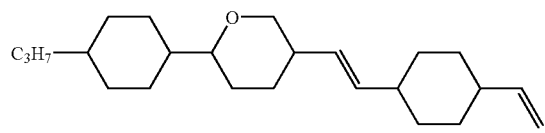
(1-5-1-42) 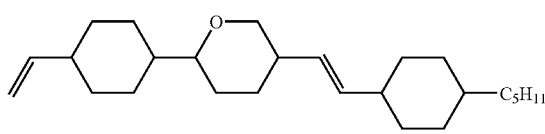
(1-5-1-43) 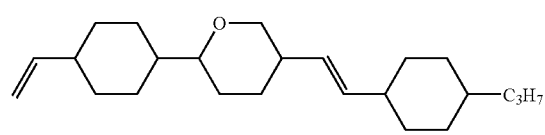
(1-5-1-44) 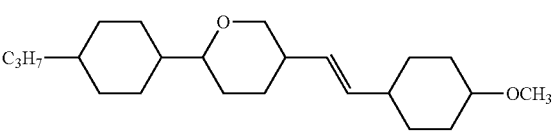
(1-5-1-45) 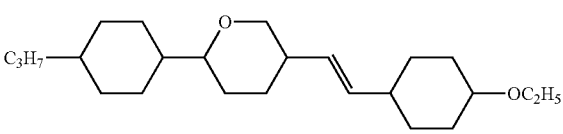
(1-5-1-46) 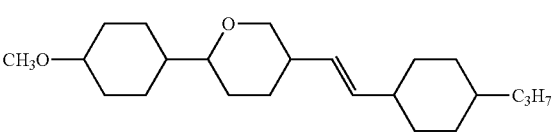
(1-5-2-1) 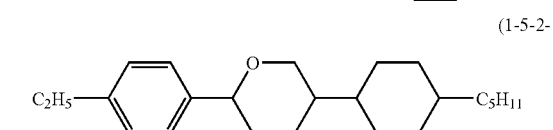
(1-5-2-2) 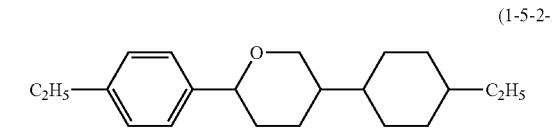
(1-5-2-3) 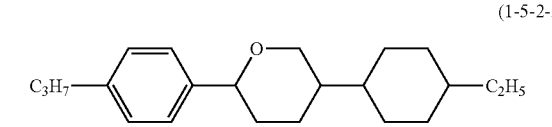
(1-5-2-4) 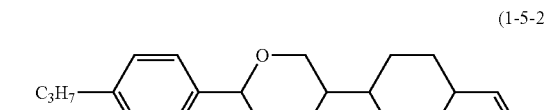
(1-5-2-5) 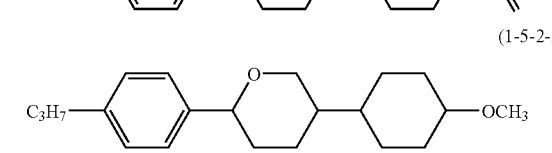
(1-5-2-6) 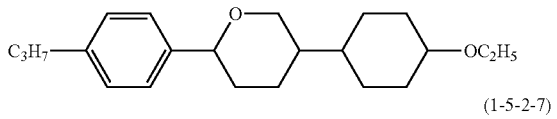
(1-5-2-7) 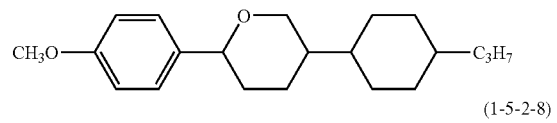
(1-5-2-8) 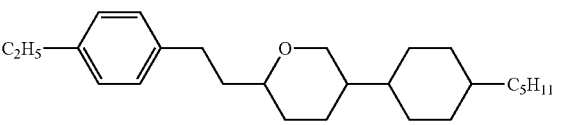
(1-5-2-9) 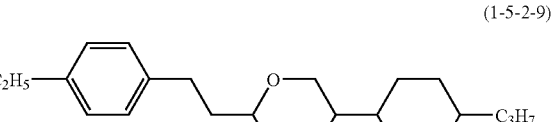
(1-5-2-10) 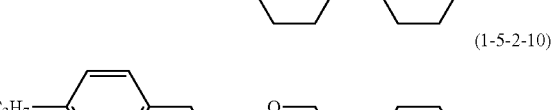
(1-5-2-11) 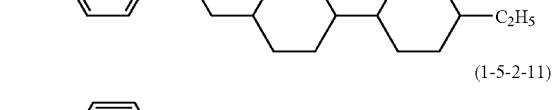
(1-5-2-12) 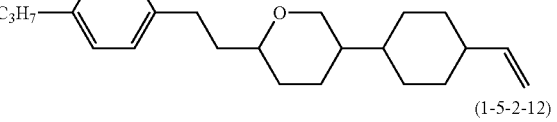
(1-5-2-13) 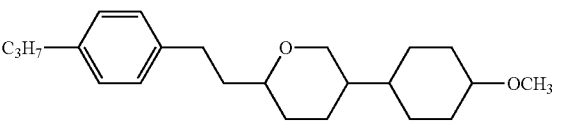
(1-5-2-14) 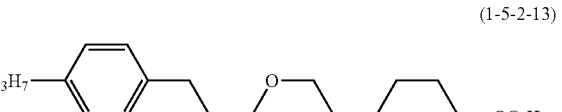
(1-5-2-15) 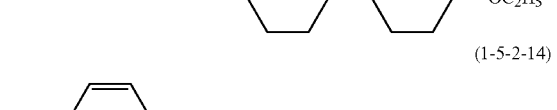

-continued
(1-5-2-17)
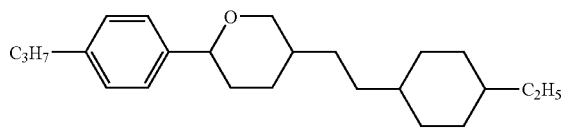
(1-5-2-18)
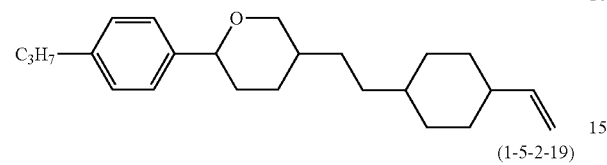
(1-5-2-19)
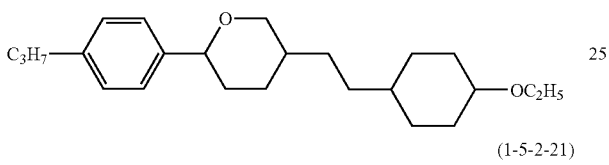
(1-5-2-20)
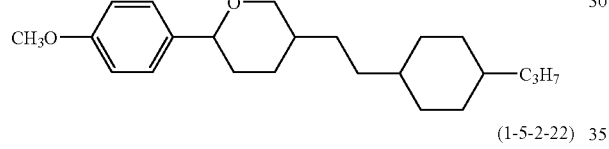
(1-5-2-21)
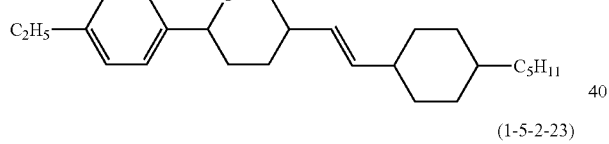
(1-5-2-22)
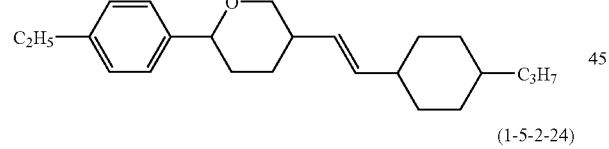
(1-5-2-23)
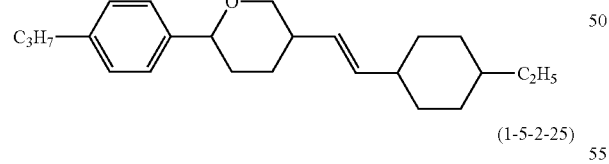
(1-5-2-24)
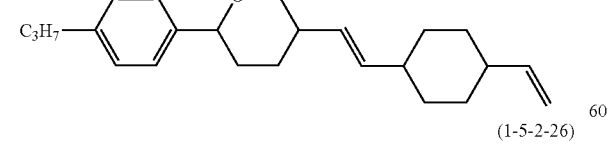
(1-5-2-25)
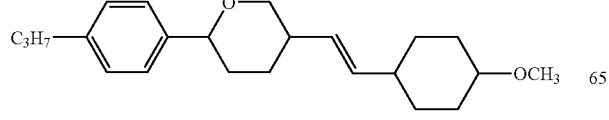
(1-5-2-26)
-continued
(1-5-2-27)
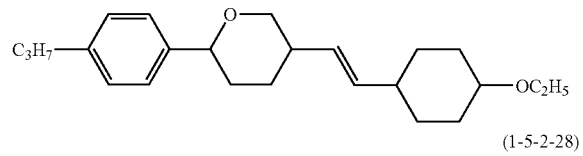
(1-5-2-28)
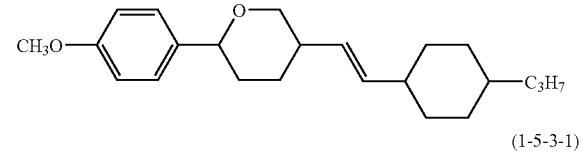
(1-5-3-1)
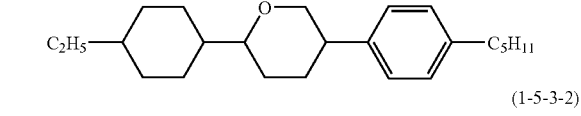
(1-5-3-2)
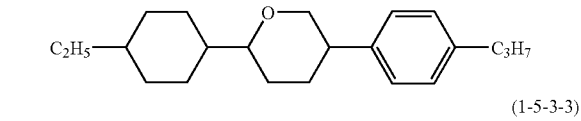
(1-5-3-3)
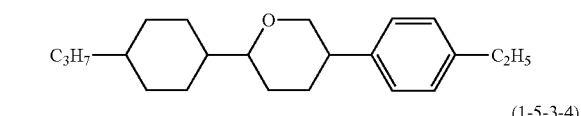
(1-5-3-4)
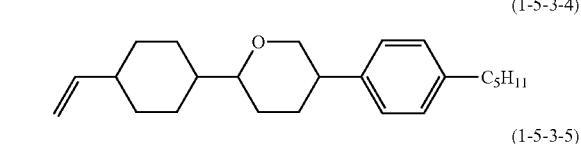
(1-5-3-5)
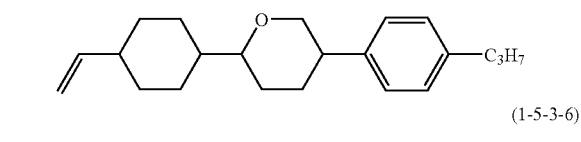
(1-5-3-6)
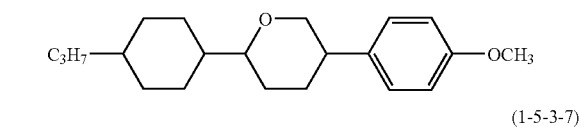
(1-5-3-7)
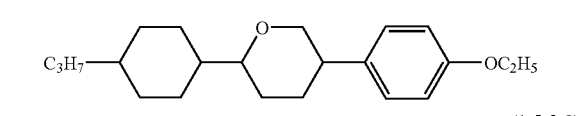
(1-5-3-8)
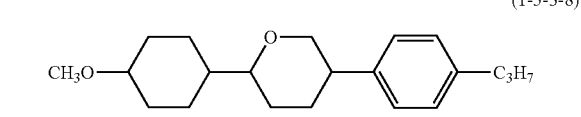
(1-5-3-9)
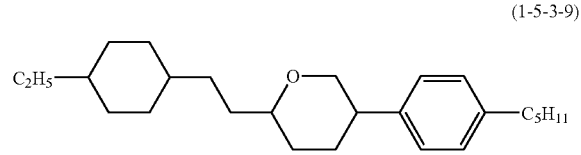
(1-5-3-10)
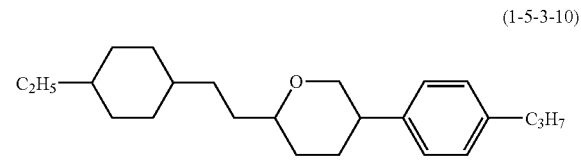

-continued
(1-5-3-11)
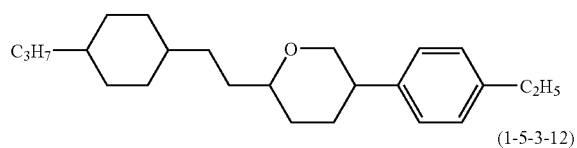
(1-5-3-12)
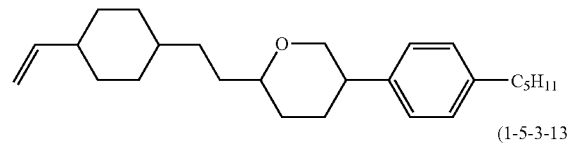
(1-5-3-13)
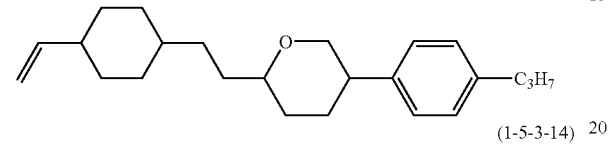
(1-5-3-14)
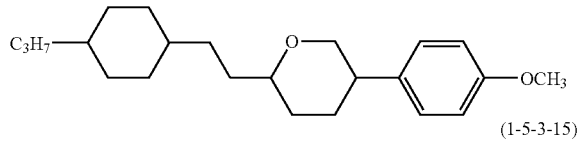
(1-5-3-15)
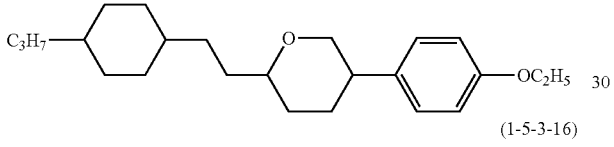
(1-5-3-16)
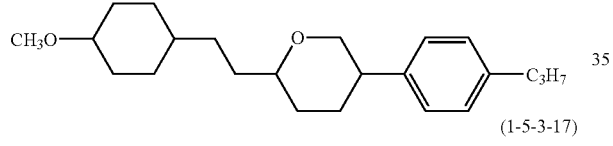
(1-5-3-17)
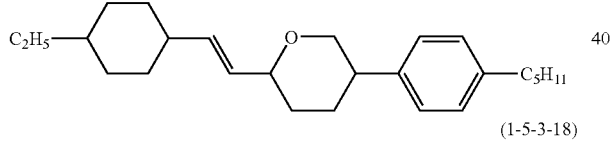
(1-5-3-18)
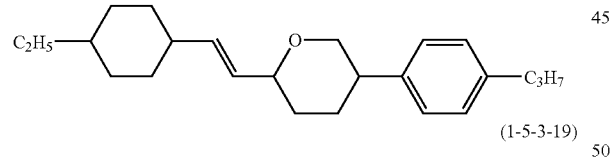
(1-5-3-19)
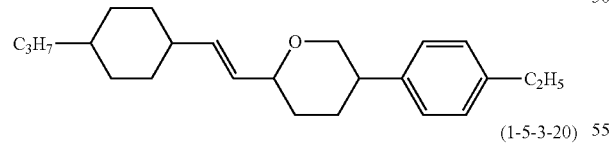
(1-5-3-20)
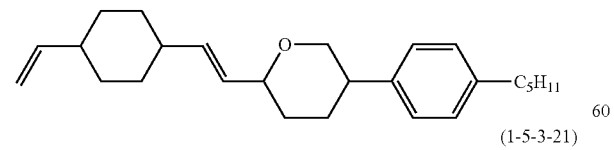
(1-5-3-21)
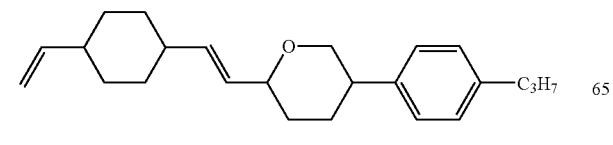
-continued
(1-5-3-22)
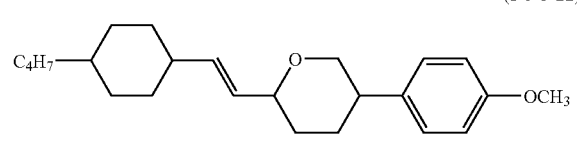
(1-5-3-23)
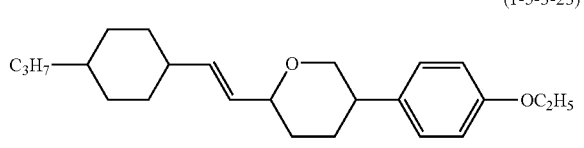
(1-5-3-24)
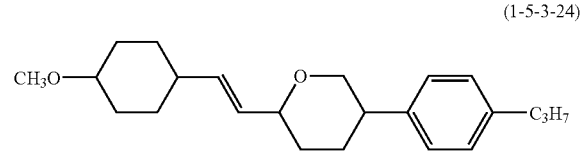
(1-5-3-25)
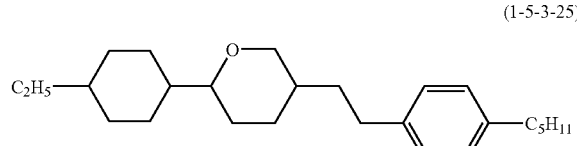
(1-5-3-26)
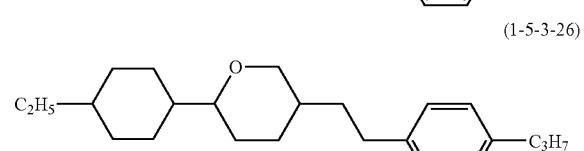
(1-5-3-27)
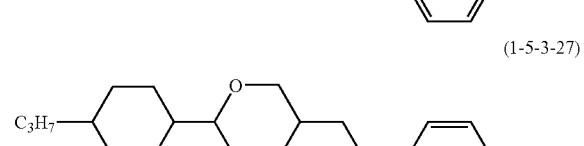
(1-5-3-28)
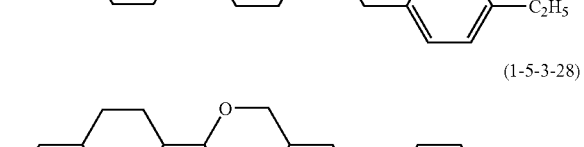
(1-5-3-29)
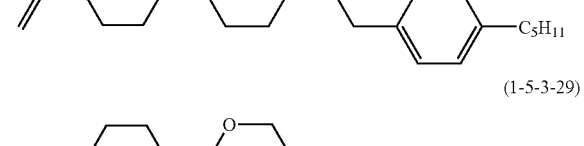
(1-5-3-30)
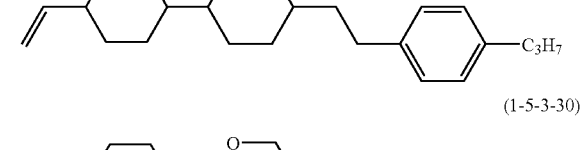
(1-5-3-31)
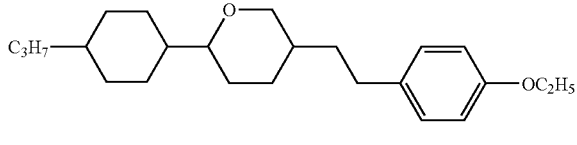

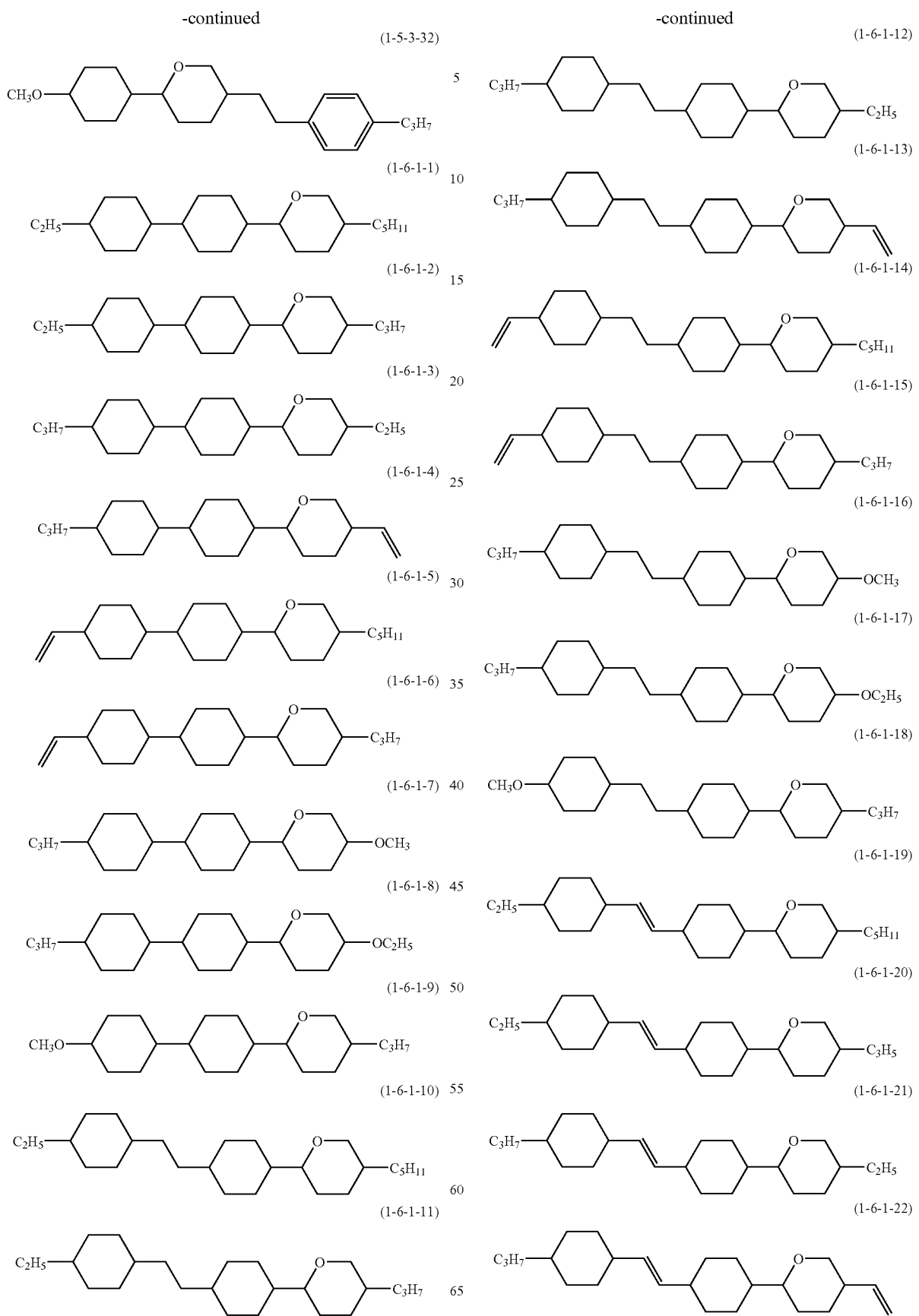

-continued
(1-6-1-23)
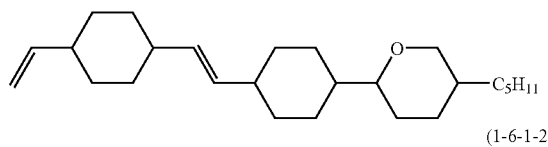
(1-6-1-24)
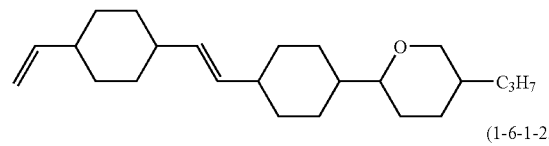
(1-6-1-25)
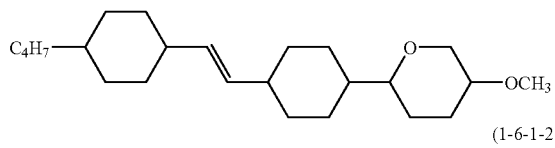
(1-6-1-26)
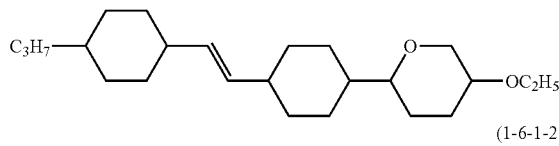
(1-6-1-26)
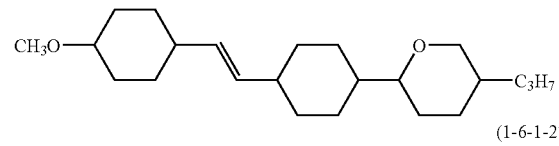
(1-6-1-27)
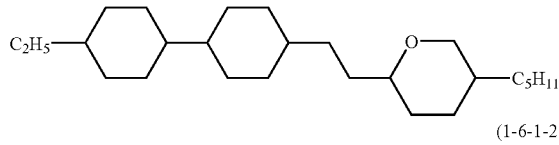
(1-6-1-28)
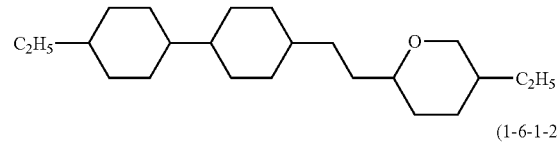
(1-6-1-29)
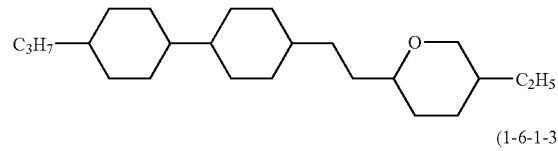
(1-6-1-30)
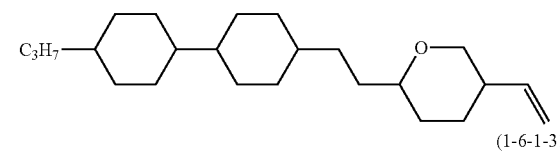
(1-6-1-31)
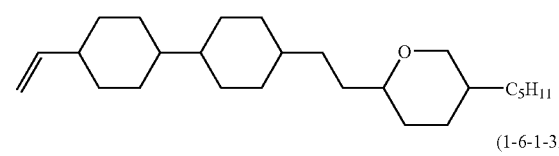
(1-6-1-32)
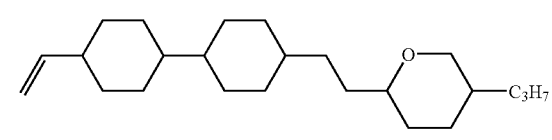
-continued
(1-6-1-33)
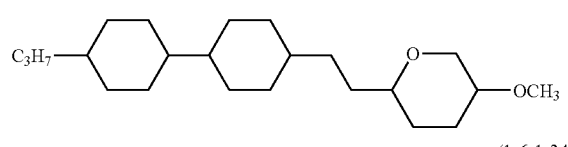
(1-6-1-34)
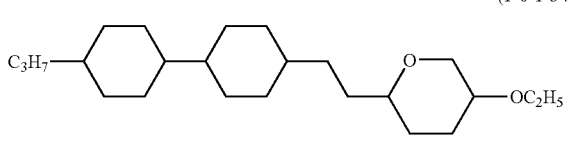
(1-6-1-35)
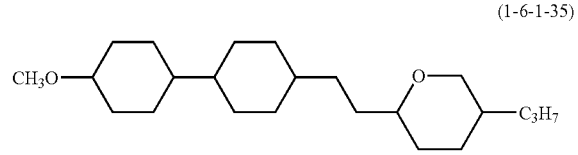
(1-6-1-36)
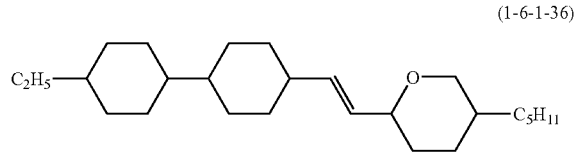
(1-6-1-37)
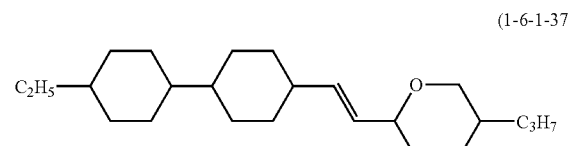
(1-6-1-38)
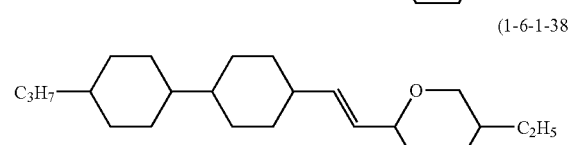
(1-6-1-39)
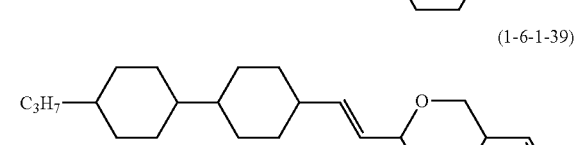
(1-6-1-40)
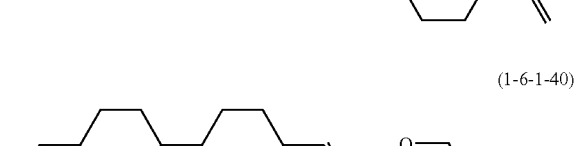
(1-6-1-41)
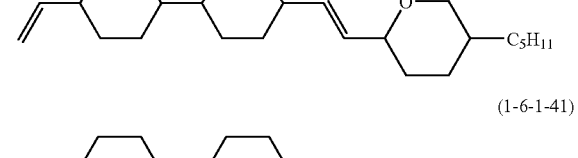
(1-6-1-42)
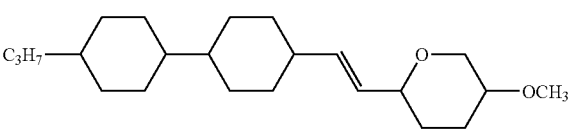

-continued
(1-6-1-43)
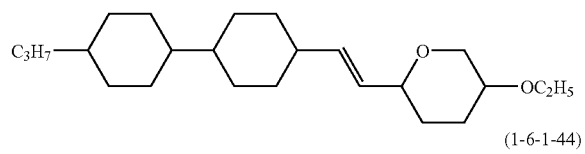
(1-6-1-44)
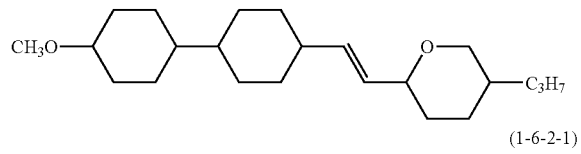
(1-6-2-1)
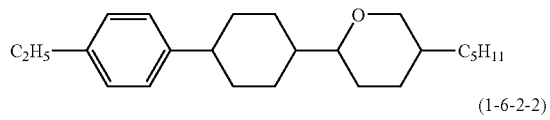
(1-6-2-2)
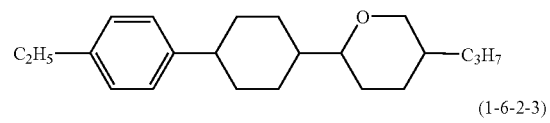
(1-6-2-3)
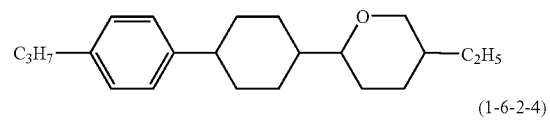
(1-6-2-4)
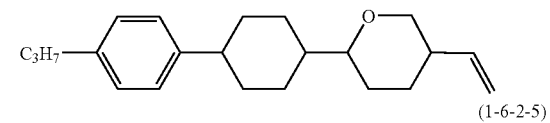
(1-6-2-5)
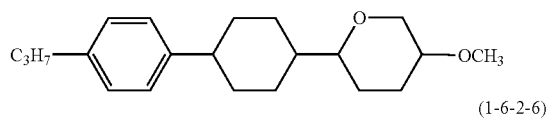
(1-6-2-6)
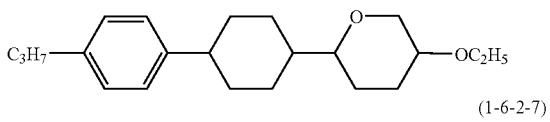
(1-6-2-7)
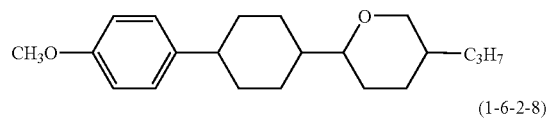
(1-6-2-8)
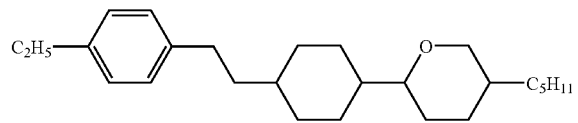
(1-6-2-9)
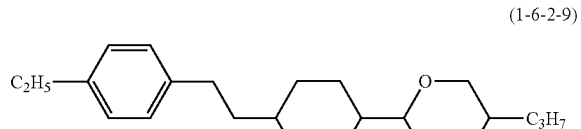
(1-6-2-10)
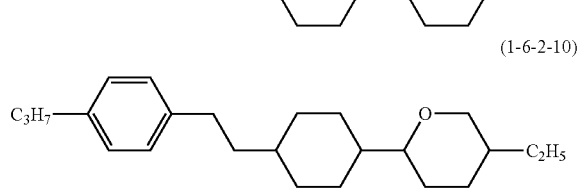
-continued
(1-6-2-11)
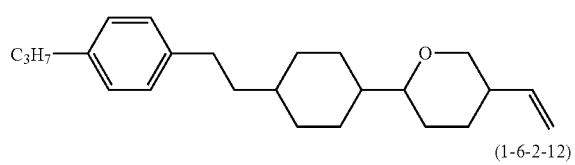
(1-6-2-12)
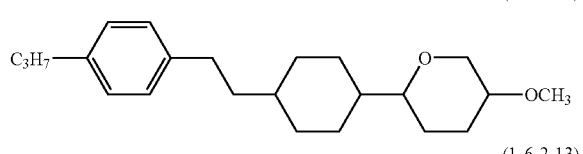
(1-6-2-13)
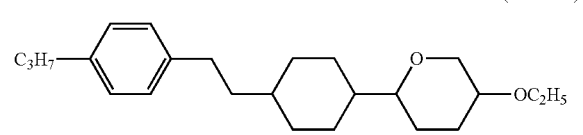
(1-6-2-14)
(1-6-2-15)
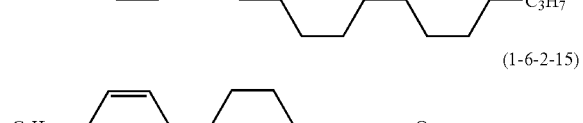
(1-6-2-16)
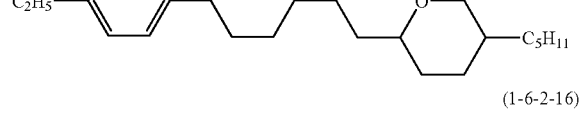
(1-6-2-17)
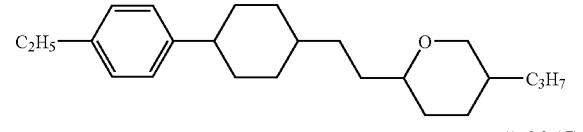
(1-6-2-18)
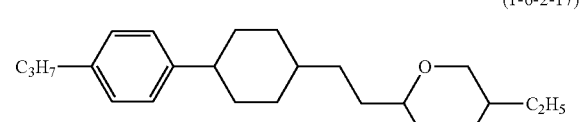
(1-6-2-19)
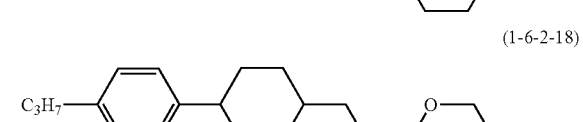
(1-6-2-20)
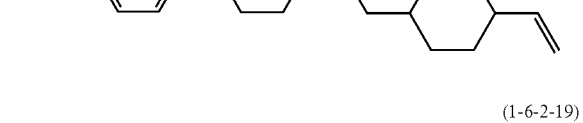

(1-6-2-21) 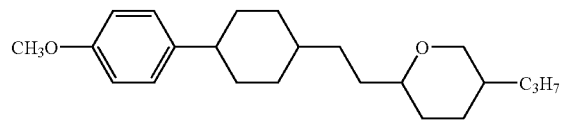
(1-6-2-22) 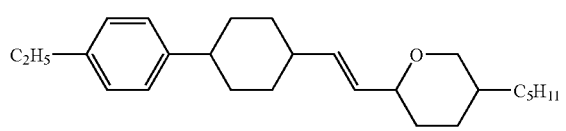
(1-6-2-23) 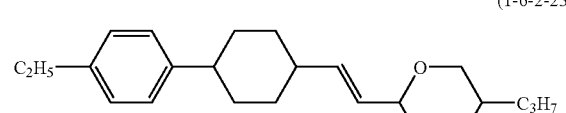
(1-6-2-24) 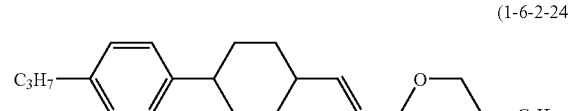
(1-6-2-25) 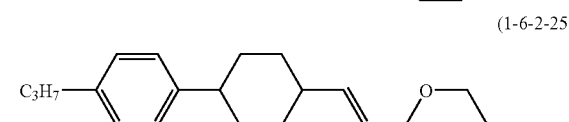
(1-6-2-26) 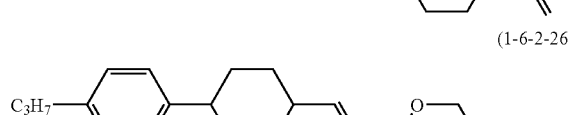
(1-6-2-27) 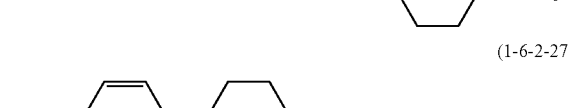
(1-6-2-28) 
(1-6-3-1) 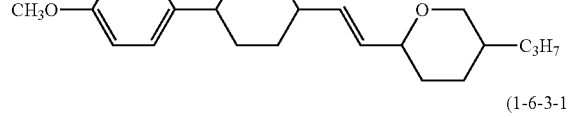
(1-6-3-2) 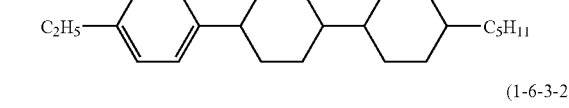
(1-6-3-3) 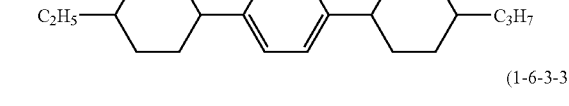
(1-6-3-4) 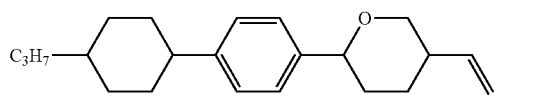
(1-6-3-5) 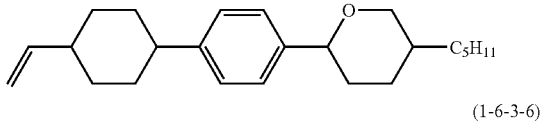
(1-6-3-6) 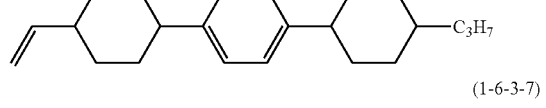
(1-6-3-7) 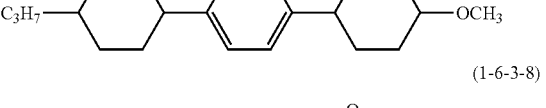
(1-6-3-8) 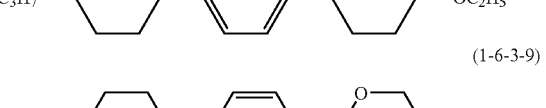
(1-6-3-9) 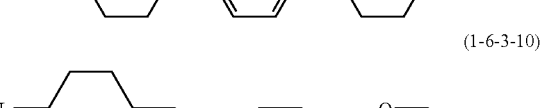
(1-6-3-10) 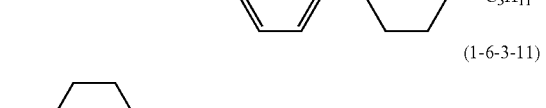
(1-6-3-11) 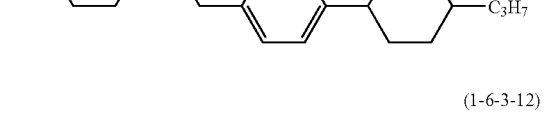
(1-6-3-12) 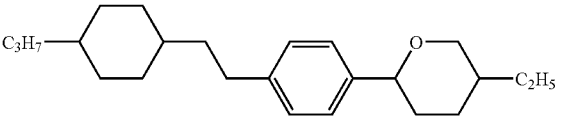
(1-6-3-13) 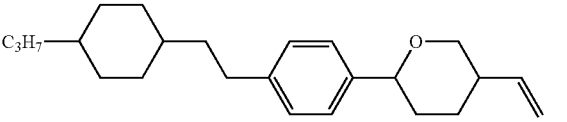
(1-6-3-14) 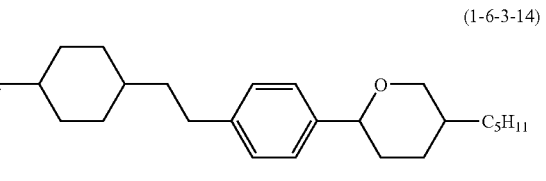

-continued (1-6-3-15)
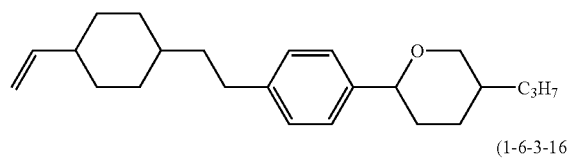

(1-6-3-16)
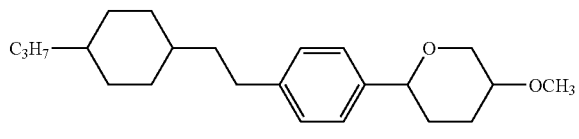

(1-6-3-17)
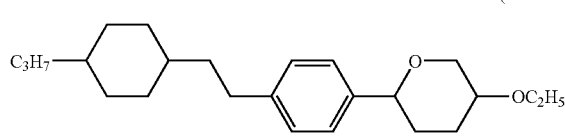

(1-6-3-18)
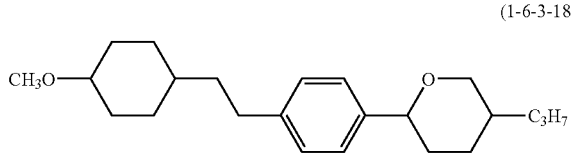

(1-6-3-19)
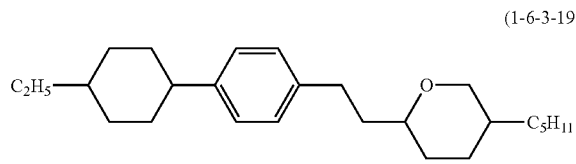

(1-6-3-20)
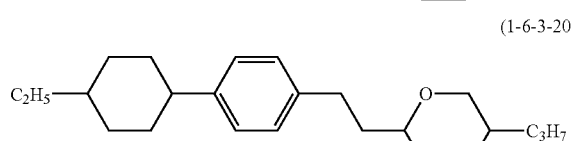

(1-6-3-21)
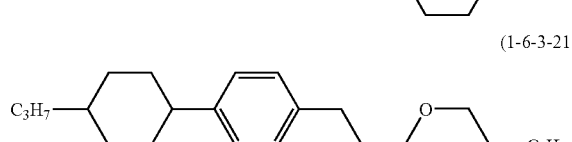

(1-6-3-22)
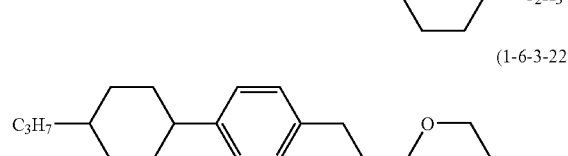

(1-6-3-23)
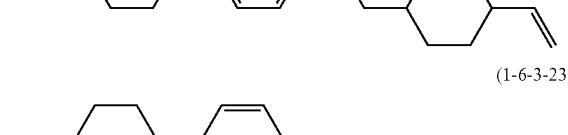

(1-6-3-24)
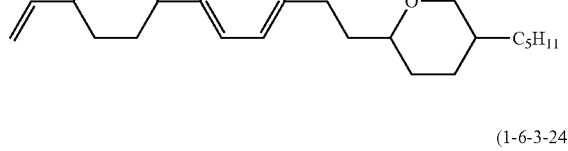

-continued (1-6-3-25)
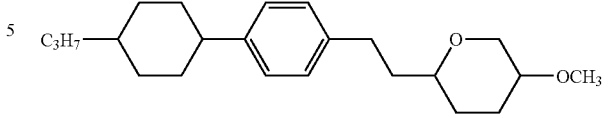

(1-6-3-26)
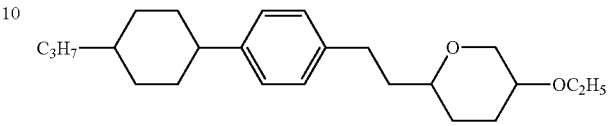

(1-6-3-27)
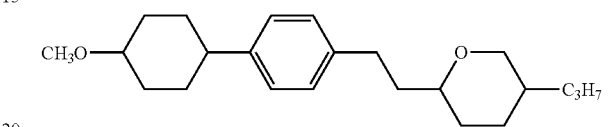

Preparation Example

Four compounds were mixed to prepare a composition A (mother liquid crystal) having a nematic phase. The four compounds used were 4-(4-propylcyclohexyl)benzonitrile (24%), 4-(4-pentylcyclohexyl)benzonitrile (36%), 4-(4-heptylcyclohexyl)benzonitrile (25%) and 4-(4-(4-pentylcyclohexyl)phenyl)benzonitrile (15%). The physical properties of the composition A were as follows.

Upper limit temperature (NI): 71.7° C.

Viscosity ($\eta_{20}$): 27.0 mPa·s

Dielectric anisotropy ($\Delta\epsilon$): 11.0

Optical anisotropy ($\Delta n$): 0.137

Example 10

A composition B containing 85% of the composition A described in Preparation Example and 15% of 2-ethyl-5-(4-pentylcyclohexyl)tetrahydropyran (Compound No. 1-1-1-1) obtained in Example 1 was prepared. The measured physical properties of the composition B were extrapolated to calculate the physical properties of the Compound No. 1-1-1-4.

Upper limit temperature (NI): 31.0° C.

Dielectric anisotropy ($\Delta\epsilon$): −0.6

Optical anisotropy ($\Delta n$): 0.024

Example 11

A composition C containing 85% of the composition A described in Preparation Example and 15% of 2-vinyl-5-(4-pentylcyclohexyl)tetrahydropyran (Compound No. 1-1-1-4) obtained in Example 2 was prepared. The measured physical properties of the composition C were extrapolated to calculate the physical properties of the Compound No. 1-1-1-4.

Upper limit temperature (NI): 51.0° C.

Viscosity ($\eta_{20}$): 2.8 mPa·s

Dielectric anisotropy ($\Delta\epsilon$): 0.3

Optical anisotropy ($\Delta n$): 0.050

Example 12

A composition D containing 85% of the composition A described in Preparation Example and 15% of 2-vinyl-5-(4-propylcyclohexyl)tetrahydropyran (Compound No. 1-1-1-5) obtained in Example 3 was prepared. The measured physical properties of the composition D were extrapolated to calculate the physical properties of the Compound No. 1-1-1-5.

Upper limit temperature (NI): 37.7° C.

Dielectric anisotropy ($\Delta\varepsilon$): −0.4

Optical anisotropy ($\Delta n$): 0.044

Example 13

A composition E containing 85% of the composition A described in Preparation Example and 15% of 2-Ethyl-5-(4'-propyl-bicyclohexyl-4-yl)tetrahydropyran (Compound No. 1-4-1-2) obtained in Example 4 was prepared. The measured physical properties of the composition E were extrapolated to calculate the physical properties of the Compound No. 1-4-1-2.

Upper limit temperature (NI): 175.0° C.

Viscosity ($\eta_{20}$): 45.5 mPa·s

Dielectric anisotropy ($\Delta\varepsilon$): 0.3

Optical anisotropy ($\Delta n$): 0.077

Example 14

A composition F containing 85% of the composition A described in Preparation Example and 15% of 5-(4'-Propyl-bicyclohexyl-4-yl)-2-vinyl-tetrahydropyran (Compound No. 1-4-1-6) obtained in Example 5 was prepared. The measured physical properties of the composition F were extrapolated to calculate the physical properties of the Compound No. 1-4-1-6.

Upper limit temperature (NI): 196.4° C.

Dielectric anisotropy ($\Delta\varepsilon$): 2.1

Optical anisotropy ($\Delta n$): 0.097

Example 15

A composition G containing 85% of the composition A described in Preparation Example and 15% of 2-Propyl-5-(4'-vinyl-bicyclohexyl-4-yl)tetrahydropyran (Compound No. 1-4-1-4) obtained in Example 6 was prepared. The measured physical properties of the composition G were extrapolated to calculate the physical properties of the Compound No. 1-4-1-4.

Upper limit temperature (NI): 182.4° C.

Dielectric anisotropy ($\Delta\varepsilon$): 1.4

Optical anisotropy ($\Delta n$): 0.084.

Example 16

A composition H containing 85% of the composition A described in Preparation Example and 15% of 2-(2-(4-Ethyl-cyclohexyl)ethyl)-5-(4-pentylcyclohexyl)tetrahydropyran (Compound No. 1-5-1-10) obtained in Example 7 was prepared. The measured physical properties of the composition H were extrapolated to calculate the physical properties of the Compound No. 1-5-1-10.

Upper limit temperature (NI): 141.0° C.

Viscosity ($\eta_{20}$): 36.5

Dielectric anisotropy ($\Delta\varepsilon$): −1.7

Optical anisotropy ($\Delta n$): 0.044

Example 17

A composition E containing 85% of the composition A described in Preparation Example and 15% of 2-(2-(4-ethyl-cyclohexyl)vinyl)-5-(4-pentylcyclohexyl)tetrahydropyran (Compound No. 1-5-1-19) obtained in Example 8 was prepared. The measured physical properties of the composition E were extrapolated to calculate the physical properties of the Compound No. 1-5-1-19.

Upper limit temperature (NI): 174.4° C.

Viscosity ($\eta_{20}$): 34.3 mPa·s

Dielectric anisotropy ($\Delta\varepsilon$): 1.4

Optical anisotropy ($\Delta n$): 0.070

Representative examples of the composition of the invention are shown below as Compositions 1 to 15. The compounds as the components of the composition and the amounts thereof (in terms of % by weight) are shown. The compounds are shown according to the method described in Table 1 below, i.e., the structures thereof are shown by the symbols corresponding to the left end group, the bonding group, the ring structure and the right end group.

TABLE 1

| Method for Description of Compounds Using Symbols |
|---|
| R—(A1)—Z1— - - - —Zn—(An)—X |

1) Left end group R—

| | |
|---|---|
| CnH2n+1— | n— |
| CnH2n+1OCmH2m— | nOm— |
| CH2=CH— | V— |
| CnH2n+1CH=CH— | nV— |
| CH2=CHCnH2n— | Vn— |
| CnH2n+1CH=CHCmH2m— | nVm— |
| CF2=CH— | VFF— |
| CF2=CHCnH2n— | VFFn— |

| 2) Ring Structure —$A_n$— | Symbol |
|---|---|
|  | B |
| 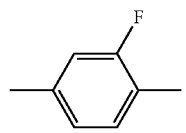 | B(F) |

TABLE 1-continued

Method for Description of Compounds Using Symbols

R—(A1)—Z1———···———Zn—(An)—X

| Structure | Symbol |
|---|---|
| 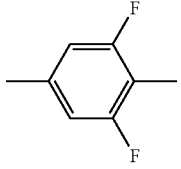 | B(F, F) |
| 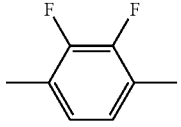 | B(2F, 3F) |
| 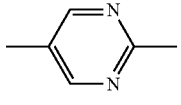 | Py |
| 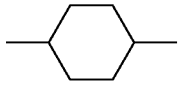 | H |
| 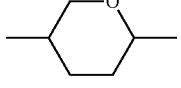 | dh |
| 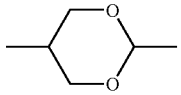 | G |

| 3) Bonding group —Zn— | Symbol |
|---|---|
| —C2H4— | 2 |
| —C4H8— | 4 |
| —CH=CH— | V |
| —COO— | E |
| —C≡C— | T |
| —CF2O— | X |

| 4) Right end group —X | Symbol |
|---|---|
| —F | —F |
| —Cl | —CL |
| —OCF2H | —OCF2H |
| —OCF3 | —OCF3 |
| —CF3 | —CF3 |
| —CnH2n+1 | —n |
| —OCnH2n+1 | —On |
| —CH=CH2 | —V |
| —CnH2nCH=CH2 | —nV |
| —CnH2nCH=CHCmH2m+1 | —nVm |
| —CH=CF2 | —VFF |
| —COOCH3 | —EMe |

5) Examples of Description

Example 1   7-HB(F)—F

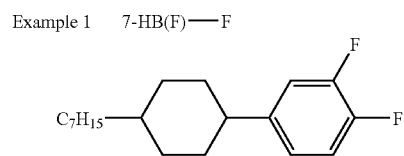

Example 2   1O1-HBBH-5

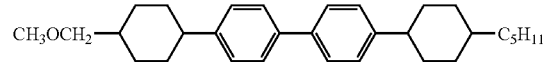

Example 3   2-HdhH-3

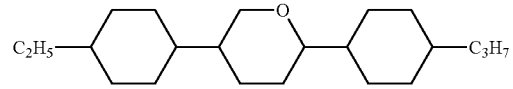

Composition 1

| | | |
|---|---|---|
| 5-Hdh2H-2 | (1-5-1-10) | 10% |
| 2-HdhH-3 | (1-5-1-3) | 5% |
| 5-HB-CL | (2-1) | 16% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 5% |
| 4-HHB(F)-F | (3-2) | 5% |
| 5-HHB(F)-F | (3-2) | 5% |
| 7-HHB(F)-F | (3-2) | 5% |
| 5-HBB(F)-F | (3-23) | 5% |
| 1O1-HBBH-5 | (14-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 121.2° C.; Δn = 0.087; (η20) = 20.8 mPa·s; Δε = 2.7; Vth = 2.84 V

When an optically active compound (Op-5) in an amount of 0.25% to the composition was added in the above Composition 1, the value of the helical pitch was 60.0 μm.

Composition 2

| | | |
|---|---|---|
| 5-Hdh-V | (1-1-1-4) | 3% |
| V-Hdh-5 | (1-1-1-7) | 3% |
| V-HdhVH-3 | (1-5-1-23) | 3% |
| 3-HHB(F,F)-F | (3-3) | 9% |
| 3-H2HB(F,F)-F | (3-15) | 9% |
| 4-H2HB(F,F)-F | (3-15) | 8% |
| 5-H2HB(F,F)-F | (3-15) | 8% |
| 3-HBB(F,F)-F | (3-24) | 20% |
| 5-HBB(F,F)-F | (3-24) | 14% |
| 3-H2BB(F,F)-F | (3-27) | 7% |
| 5-HHBB(F,F)-F | (4-6) | 3% |
| 5-HHEBB-F | (4) | 2% |
| 3-HH2BB(F,F)-F | (4-15) | 3% |
| 1O1-HBBH-4 | (14-1) | 4% |
| 1O1-HBBH-5 | (14-1) | 4% |

Composition 3

| | | |
|---|---|---|
| 5-Hdh-2 | (1-1-1-1) | 5% |
| 5-Hdh2B-2 | (1-5-2-8) | 5% |
| 5-HB-F | (2-1) | 12% |

-continued

| | | |
|---|---|---|
| 6-HB-F | (2-1) | 9% |
| 7-HB-F | (2-1) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 5% |
| 5-HBB(F)-F | (3-23) | 5% |
| 5-HBBH-3 | (14-1) | 3% |
| 3-HB(F)BH-3 | (14-2) | 3% |

Composition 4

| | | |
|---|---|---|
| 5-Hdh-1V | (1-1-1-6) | 5% |
| 3-HdhB-2 | (1-5-2) | 4% |
| 5-HB-CL | (2-1) | 7% |
| 3-HH-4 | (12-1) | 8% |
| 3-HHB-1 | (13-1) | 5% |
| 3-HHB(F,F)-F | (3-3) | 8% |
| 3-HBB(F,F)-F | (3-24) | 20% |
| 5-HBB(F,F)-F | (3-24) | 10% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-36) | 3% |
| 3-HBEB(F,F)-F | (3-36) | 5% |
| 5-HBEB(F,F)-F | (3-36) | 3% |
| 3-HHBB(F,F)-F | (4-6) | 6% |

Composition 5

| | | |
|---|---|---|
| V-Hdh2H-3 | (1-5-1-13) | 4% |
| 5-Hdh2B-2 | (1-5-2-8) | 6% |
| 3-HB-CL | (2-1) | 3% |
| 5-HB-CL | (2-1) | 2% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-15) | 7% |
| 2-H2BB(F)-F | (3-26) | 5% |
| 3-H2BB(F)-F | (3-26) | 5% |
| 3-HBEB(F,F)-F | (3-36) | 5% |

Composition 6

| | | |
|---|---|---|
| 5-Hdh-V | (1-1-1-4) | 4% |
| 5-Hdh2H-2 | (1-5-1-10) | 5% |
| 3-HdhB-2 | (1-5-2) | 5% |
| 5-HB-CL | (2-1) | 13% |
| 7-HB(F,F)-F | (2-3) | 3% |
| 3-HH-4 | (12-1) | 10% |
| 3-HH-5 | (12-1) | 5% |
| 3-HB-O2 | (12-5) | 5% |
| 3-HHB-1 | (13-1) | 8% |
| 3-HHB-O1 | (13-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Composition 7

| | | |
|---|---|---|
| 2-HdhH-3 | (1-5-1-3) | 5% |
| V-HdhVH-3 | (1-5-1-23) | 5% |
| 5-HB-CL | (2-1) | 3% |
| 7-HB(F)-F | (2-2) | 7% |
| 3-HH-4 | (12-1) | 9% |
| 3-HH-Eme | (—) | 13% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-91) | 5% |
| 5-HGB(F,F)-F | (3-91) | 6% |
| 2-H2GB(F,F)-F | (3-94) | 4% |
| 3-H2GB(F,F)-F | (3-94) | 5% |
| 5-GHB(F,F)-F | (3-97) | 7% |

Composition 8

| | | |
|---|---|---|
| 5-Hdh-1V | (1-1-1-6) | 5% |
| 5-HdhVH-2 | (1-5-1-19) | 5% |
| 3-HH-4 | (12-1) | 8% |
| 3-HHB-1 | (13-1) | 6% |
| 3-HHB(F,F)-F | (3-3) | 10% |
| 3-H2HB(F,F)-F | (3-15) | 9% |
| 3-HBB(F,F)-F | (3-24) | 15% |
| 3-BB(F,F)XB(F,F)-F | (3-85) | 25% |
| 1O1-HBBH-5 | (14-1) | 7% |
| 2-HHBB(F,F)-F | (4-6) | 3% |
| 3-HHBB(F,F)-F | (4-6) | 3% |
| 3-HH2BB(F,F)-F | (4-15) | 4% |

NI = 90.6° C.; $\Delta n$ = 0.108; $(\eta_{20})$ = 26.3 mPa · s;; $\Delta \epsilon$ = 9.6; Vth = 1.52 V.

Composition 9

| | | |
|---|---|---|
| 5-Hdh2H-2 | (1-5-1-10) | 4% |
| 2-HdhH-3 | (1-5-1-3) | 4% |
| 3-HH-4 | (12-1) | 5% |
| 3-HH-5 | (12-1) | 5% |
| 3-HH-O1 | (12-1) | 6% |
| 3-HH-O3 | (12-1) | 6% |
| 3-HB-O1 | (12-5) | 5% |
| 3-HB-O2 | (12-5) | 5% |
| 3-HB(2F,3F)-O2 | (7-1) | 10% |
| 5-HB(2F,3F)-O2 | (7-1) | 10% |
| 3-HHEH-3 | (13-20) | 4% |
| 3-HHEH-5 | (13-20) | 3% |
| 4-HHEH-3 | (13-20) | 3% |
| 2-HHB(2F,3F)-1 | (8-1) | 4% |
| 3-HHB(2F,3F)-2 | (8-1) | 4% |
| 3-HHB(2F,3F)-O2 | (8-1) | 12% |
| 5-HHB(2F,3F)-O2 | (8-1) | 10% |

NI = 85.6° C.; $\Delta n$ = 0.075; $(\eta_{20})$ = 27.4 mPa · s; $\Delta \epsilon$ = −3.3.

Composition 10

| | | |
|---|---|---|
| 2-HdhH-3 | (1-5-1-3) | 5% |
| 3-dh2BH-2 | (1-6-3-20) | 5% |
| 5-HB-CL | (2-1) | 3% |
| 7-HB(F)-F | (5-3) | 7% |
| 3-HH-4 | (12-1) | 9% |
| 3-HH-Eme | (—) | 13% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-91) | 5% |
| 5-HGB(F,F)-F | (3-91) | 6% |
| 2-H2GB(F,F)-F | (3-94) | 4% |
| 3-H2GB(F,F)-F | (3-94) | 5% |
| 5-GHB(F,F)-F | (3-97) | 7% |

Composition 11

| | | |
|---|---|---|
| 3-dhdh-V | (1-3) | 5% |
| 3-HdhB-2 | (1-5-2) | 4% |
| 5-HB-CL | (2-1) | 7% |
| 3-HH-4 | (12-1) | 8% |
| 3-HHB-1 | (13-1) | 5% |
| 3-HHB(F,F)-F | (3-3) | 8% |
| 3-HBB(F,F)-F | (3-24) | 20% |
| 5-HBB(F,F)-F | (3-24) | 10% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-36) | 3% |
| 3-HBEB(F,F)-F | (3-36) | 5% |
| 5-HBEB(F,F)-F | (3-36) | 3% |
| 3-HHBB(F,F)-F | (4-6) | 6% |

Composition 12

| | | |
|---|---|---|
| 5-Hdh-1V | (1-1-1-6) | 4% |
| 5-Hdh2H-2 | (1-5-1-10) | 4% |
| 5-HdhVH-2 | (1-5-1-19) | 3% |
| 2-BEB(F)-C | (5) | 5% |
| 3-BEB(F)-C | (5) | 4% |
| 4-BEB(F)-C | (5) | 12% |
| 1V2-BEB(F,F)-C | (5) | 16% |
| 3-HB-O2 | (12-5) | 3% |
| 3-HH-4 | (12-1) | 3% |
| 3-HHB-F | (3-1) | 3% |
| 3-HHB-1 | (13-1) | 4% |
| 3-HHB-O1 | (13-1) | 4% |
| 3-HBEB-F | (3-34) | 4% |
| 3-HHEB-F | (3-34) | 7% |
| 5-HHEB-F | (3-34) | 7% |
| 3-H2BTB-2 | (13-15) | 4% |
| 3-H2BTB-3 | (13-15) | 4% |
| 3-H2BTB-4 | (13-15) | 4% |
| 3-HB(F)TB-2 | (13-14) | 5% |

NI = 92.7° C.;
Δn = 0.138;
(η20) = 41.7 mPa · s;
Δε = 28.0;
Vth = 1.07 V.

Composition 13

| | | |
|---|---|---|
| V-Hdh-5 | (1-1-1-7) | 10% |
| 5-Hdh2B-2 | (1-5-2-8) | 5% |

-continued

| | | |
|---|---|---|
| 3-BEB(F)-C | (5) | 8% |
| 3-HB-C | (5-2) | 8% |
| V-HB-C | (5-2) | 8% |
| 1V-HB-C | (5-2) | 8% |
| 3-HB-O2 | (12-5) | 3% |
| 3-HH-2V | (12-1) | 9% |
| 3-HH-2V1 | (12-1) | 3% |
| V2-HHB-1 | (13-1) | 9% |
| 3-HHB-1 | (13-1) | 5% |
| 3-HHEB-F | (3-10) | 7% |
| 3-H2BTB-2 | (13-15) | 6% |
| 3-H2BTB-3 | (13-15) | 6% |
| 3-H2BTB-4 | (13-15) | 5% |

Composition 14

| | | |
|---|---|---|
| V-Hdh2H-3 | (1-5-1-13) | 10% |
| V-HdhVH-3 | (1-5-1-23) | 8% |
| 5-BEB(F)-C | (5) | 5% |
| V-HB-C | (5-2) | 11% |
| 5-PyB-C | (5-8) | 6% |
| 4-BB-3 | (12-8) | 11% |
| 3-HH-2V | (12-1) | 10% |
| 5-HH-V | (12-1) | 11% |
| V-HHB-1 | (13-3) | 7% |
| V2-HHB-1 | (13-3) | 3% |
| 3-HHB-1 | (13-3) | 3% |
| 1V2-HBB-2 | (13-4) | 10% |
| 3-HHEBH-3 | (14-6) | 5% |

Composition 15

| | | |
|---|---|---|
| 5-Hdh-2 | (1-1-1-1) | 5% |
| V-Hdh-5 | (1-1-1-7) | 6% |
| 1V2-BEB(F,F)-C | (5) | 8% |
| 3-HB-C | (5-2) | 18% |
| 2-BTB-1 | (12-10) | 10% |
| 5-HH-VFF | (12-1) | 20% |
| 3-HHB-1 | (13-1) | 6% |
| VFF-HHB-1 | (13-1) | 6% |
| VFF2-HHB-1 | (13-1) | 6% |
| 3-H2BTB-2 | (13-15) | 5% |
| 3-H2BTB-3 | (13-15) | 5% |
| 3-H2BTB-4 | (13-15) | 5% |

What is claimed is:
1. A compound represented by the following formula (1):

(1)

wherein
R¹ and R² are independently hydrogen or alkyl having from 1 to 10 carbons, provided that in the alkyl arbitrary —CH₂— may be replaced by —O—, —S—, —CO— or —SiH₂—, and arbitrary —(CH₂)₂— may be replaced by —CH=CH— or —C≡C—;
T¹, T² and T³ are independently tetrahydropyran-2,5-diyl or tetrahydropyran-3,6-diyl;
A¹ and A² are independently 1,4-cyclohexylene, 1,4-phenylene, decahydronaphthalene-2,6-diyl, 1,2,3,4-tetrahydronaphthalene-2,6-diyl or naphthalene-2,6-diyl, provided that in these rings one of —CH₂— may be replaced by —O—, —S—, —CO— or —SiH$_2$—, and arbitrary —(CH$_2$)$_2$— may be replaced by —CH=CH—, and in the 1,4-phenylene one of —CH= may be replaced by —N=;

$Z^1$, $Z^2$, $Z^3$ and $Z^4$ are independently a single bond or alkylene having from 1 to 4 carbons, provided that in the alkylene arbitrary —CH$_2$— may be replaced by —O—, —S—, —CO— or —SiH$_2$—, and arbitrary —(CH$_2$)$_2$— may be replaced by —CH=CH— or —C≡C—;

i is 0 or 1;

j, k and m are independently 0, 1 or 2;

n is 0 or 1;

i+j+k+m+n is 2, 3 or 4; and i+k+n is 1, 2, 3 or 4, wherein when i is 0, j is 1 or 2;

when n is 0, m is 1 or 2, and $Z^4$ is a single bond;

when i is 1, $R^1$ is alkyl having from 1 to 10 carbons, provided that in the alkyl arbitrary —CH$_2$— may be replaced by —O—, —S—, —CO— or —SiH$_2$—, and arbitrary —(CH$_2$)$_2$— may be replaced by —CH=CH— or —C≡C—;

when i+k+n is 1, $T^1$, $T^2$ and $T^3$ are independently tetrahydropyran-2,5-diyl;

when i+j+k+m+n is 2, j, k and m are independently 0 or 1, and $A^1$ and $A^2$ are independently 1,4-cyclohexylene or decahydronaphthalene-2,6-diyl, provided that in these rings one of —CH$_2$— may be replaced by —O—, —S—, —CO— or —SiH$_2$—;

when i+j+k+m+n is 3, j, k and m are independently 0 or 1, and at least one of $A^1$ and $A^2$ is 1,4-cyclohexylene or decahydronaphthalene-2,6-diyl, provided that in these rings one of —CH$_2$— may be replaced by —O—, —S—, —CO— or —SiH$_2$—, wherein when i+j+k+m+n is 3, i+k is 0, $A^1$ is 1,4-cyclohexylene and $A^2$ is 1,4-phenylene, at least one of $R^1$ and $R^2$ is alkenyl; and when i+j+k+m+n is 4, at least two of $A^1$ and $A^2$ each is 1,4-cyclohexylene or decahydronaphthalene-2,6-diyl, provided that in these rings one of —CH$_2$— may be replaced by —O—, —S—, —CO— or —SiH$_2$—, wherein when i+j+k+m+n is 4, j+m is 3 and n is 1, j is 1.

2. The compound according to claim 1, wherein the compound is represented by one of the following formulae (1-1), (1-2), (1-4) to (1-6) and (1-11) to (1-14):

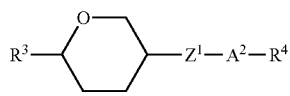

(1-1)

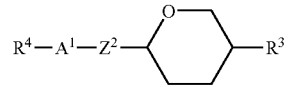

(1-2)

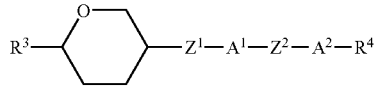

(1-4)

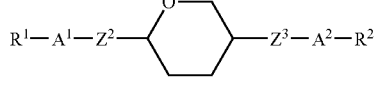

(1-5)

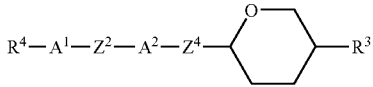

(1-6)

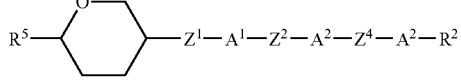

(1-11)

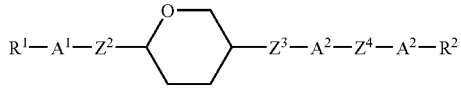

(1-12)

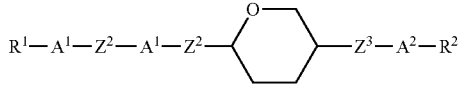

(1-13)

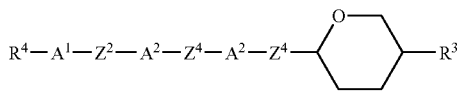

(1-14)

wherein $R^1$, $R^2$ and $R^4$ are independently hydrogen or alkyl having from 1 to 10 carbons, provided that in the alkyl arbitrary —CH$_2$— may be replaced by —O—, —S—, —CO— or —SiH$_2$—, and arbitrary —(CH$_2$)$_2$— may be replaced by —CH=CH— or —C≡C—; $R^3$ and $R^5$ are independently alkyl having from 1 to 10 carbons, provided that in the alkyl arbitrary —CH$_2$— may be replaced by —O—, —S—, —CO— or —SiH$_2$—, and arbitrary —(CH$_2$)$_2$— may be replaced by —CH=CH— or —C≡C—; $A^1$ and $A^2$ are independently 1,4-cyclohexylene, 1,4-phenylene, decahydronaphthalene-2,6-diyl, 1,2,3,4-tetrahydronaphthalene-2,6-diyl or naphthalene-2,6-diyl, provided that in these rings one of —CH$_2$— may be replaced by —O—, —S—, —CO— or —SiH$_2$—, and arbitrary —(CH$_2$)$_2$— may be replaced by —CH=CH—, and in the 1,4-phenylene one of —CH= may be replaced by —N=; $Z^1$, $Z^2$, $Z^3$ and $Z^4$ are independently a single bond or alkylene having from 1 to 4 carbons, provided that in the alkylene arbitrary —CH$_2$— may be replaced by —O—, —S—, —CO— or —SiH$_2$—, and arbitrary —(CH$_2$)$_2$— may be replaced by —CH=CH— or —C≡C—; in the formula (1-6) when $A^1$ is 1,4-cyclohexylene and $A^2$ is 1,4-phenylene, at least one of $R^3$ and $R^4$ is alkenyl; and in the formula (1-14) when $A^1$ is 1,4-cyclohexylene and $A^2$ is 1,4-phenylene, at least one of $R^3$ and $R^4$ is alkenyl.

3. The compound according to claim 2, wherein in the formulae (1-1), (1-2), (1-4) to (1-6) and (1-11) to (1-14), $R^1$ to $R^5$ are independently alkyl having from 2 to 10 carbons, alkenyl having from 2 to 10 carbons, alkoxy having from 1 to 9 carbons, alkoxyalkyl having from 2 to 9 carbons, alkenyloxy having from 3 to 9 carbons, polyfluoroalkyl having from 2 to 10 carbons; $A^1$ and $A^2$ are independently 1,4-cyclohexylene, 1,4-phenylene, decahydronaphthalene-2,6-diyl, 1,2,3,4-tetrahydro-naphthalene-2,6-diyl or naphthalene-2,6-diyl; and $Z^1$, $Z^2$, $Z^3$ and $Z^4$ are independently a single bond, —(CH$_2$)$_2$—, —CH=CH—, —CH$_2$O—, —OCH$_2$—, —(CH$_2$)$_4$—, —C≡C—, —COO—, —OCO—, —C≡C—, —CH$_2$CO—, —COCH$_2$—, —CH$_2$SiH$_2$—, —SiH$_2$CH$_2$—, —O(CH$_2$)$_2$O—, —(CH$_2$)$_2$COO—, —(CH$_2$)$_2$OCO—, —COO(CH$_2$)$_2$—, —OCO(CH$_2$)$_2$—, —CH=CH—CH$_2$O— or —OCH$_2$—CH=CH—.

4. The compound according to claim 2, wherein in the formulae (1-1), (1-2), (1-4) to (1-6) and (1-11) to (1-14), $R^1$ to $R^5$ are independently alkyl having from 2 to 10 carbons, alkenyl having from 2 to 10 carbons, alkoxy having from 1 to 9 carbons, alkoxyalkyl having from 2 to 9 carbons or alkenyloxy having from 3 to 9 carbons; $A^1$ and $A^2$ are independently 1,4-cyclohexylene or 1,4-phenylene; and $Z^1$, $Z^2$, $Z^3$ and $Z^4$ are independently a single bond, —$(CH_2)_2$—, —CH=CH—, —$CH_2O$—, —$OCH_2$—, —$(CH_2)_4$— or —C≡C—.

5. The compound according to claim 2, wherein in the formulae (1-1), (1-2), (1-4) to (1-6) and (1-11) to (1-14), $R^1$ to $R^5$ are independently alkyl having from 2 to 10 carbons, alkenyl having from 2 to 10 carbons or alkoxy having from 1 to 9 carbons; $A^1$ and $A^2$ are independently 1,4-cyclohexylene or 1,4-phenylene; and $Z^1$, $Z^2$, $Z^3$ and $Z^4$ are independently a single bond, —$(CH_2)_2$— or —CH=CH—.

6. The compound according to claim 2, wherein in the formulae (1-1) and (1-2), $A^1$ and $A^2$ are 1,4-cyclohexylene; in the formulae (1-4) to (1-6), $A^1$ and $A^2$ are independently 1,4-cyclohexylene or 1,4-phenylene, and at least one of $A^1$ and $A^2$ is 1,4-cyclohexylene; and in the formulae (1-11) to (1-14), $A^1$ and $A^2$ are independently 1,4-cyclohexylene or 1,4-phenylene, and at least two of $A^1$ and $A^2$ are 1,4-cyclohexylene.

7. The compound according to claim 2, wherein the compound is represented by one of the following formulae (1-1-1), (1-2-1), (1-4-1) to (1-4-3), (1-5-1) to (1-5-3), (1-6-1) to (1-6-3), (1-11-1) to (1-11-4), (1-12-1) to (1-12-4), (1-13-1) to (1-13-4), and (1-14-1) to (1-14-4):

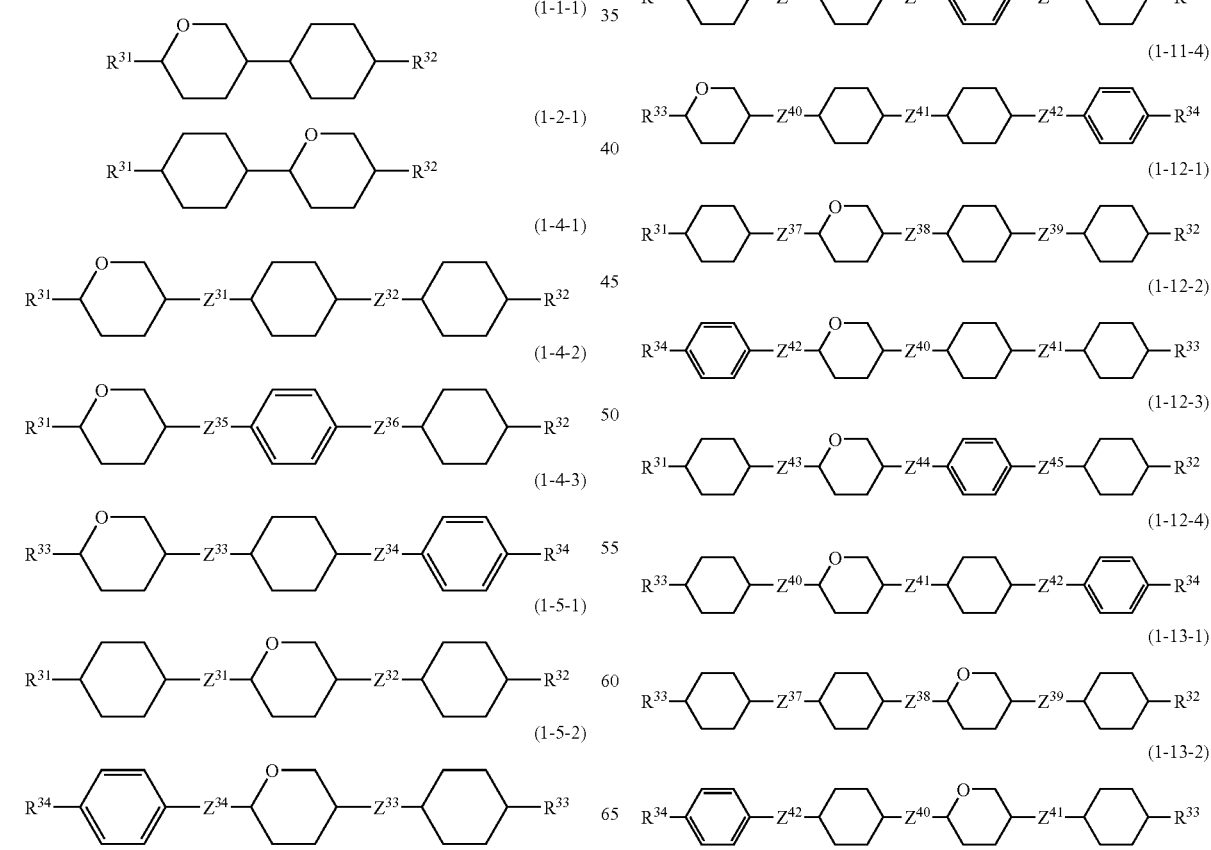

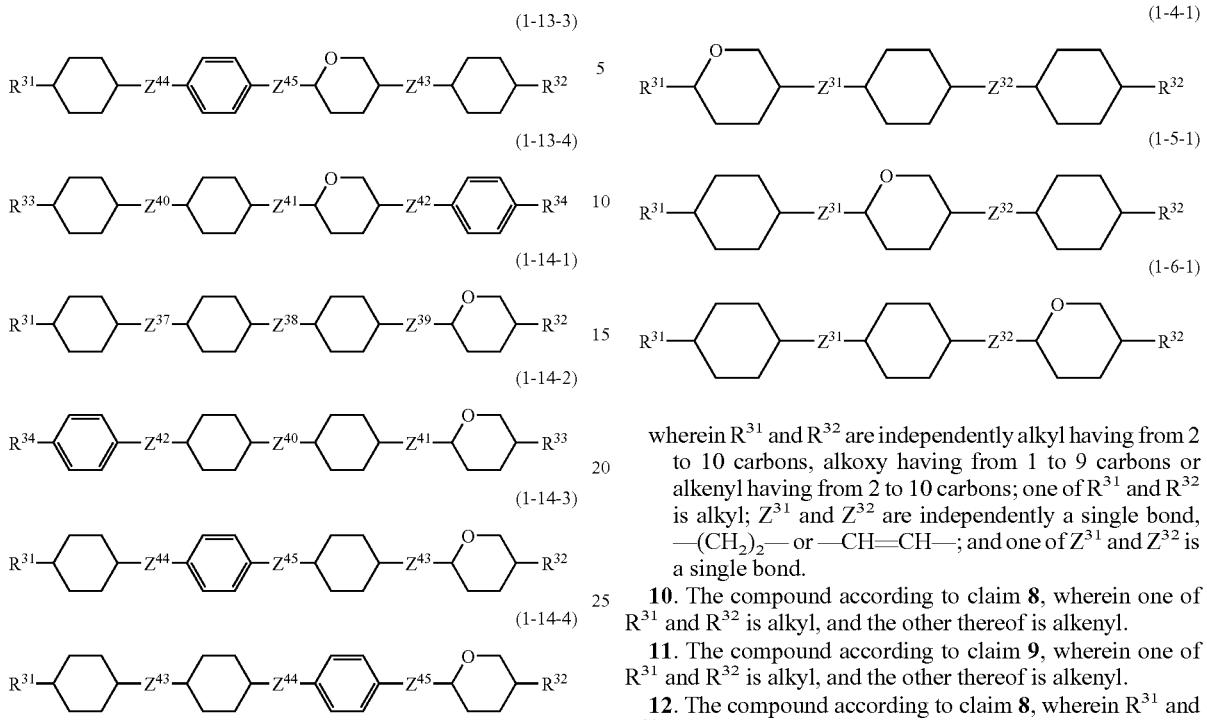

wherein $R^{31}$, $R^{32}$ and $R^{33}$ are independently alkyl having from 2 to 10 carbons, alkoxy having from 1 to 9 carbons or alkenyl having from 2 to 10 carbons; $R^{34}$ is alkyl having from 2 to 10 carbons, alkoxy having from 1 to 9 carbons or alkenyl having from 2 to 10 carbons other than 1-alkenyl; one of $R^{31}$ and $R^{32}$ is alkyl; one of $R^{33}$ and $R^{34}$ is alkyl; $Z^{31}, Z^{32}, Z^{33}, Z^{37}, Z^{38}, Z^{39}, Z^{40}, Z^{41}$ and $Z^{43}$ are independently a single bond, $—(CH_2)_2—$ or $—CH=CH—$; $Z^{34}, Z^{35}, Z^{36}, Z^{42}, Z^{44}$ and $Z^{45}$ are independently a single bond or $—(CH_2)_2—$; one of $Z^{31}$ and $Z^{32}$ is a single bond; one of $Z^{33}$ and $Z^{34}$ is a single bond; one of $Z^{35}$ and $Z^{36}$ is a single bond; two of $Z^{37}, Z^{38}$ and $Z^{39}$ is a single bond; two of $Z^{40}, Z^{41}$ and $Z^{42}$ are a single bond; and two of $Z^{43}, Z^{44}$ and $Z^{45}$ are a single bond.

8. A compound represented by any one of the following formulae (1-1-1) and (1-2-1):

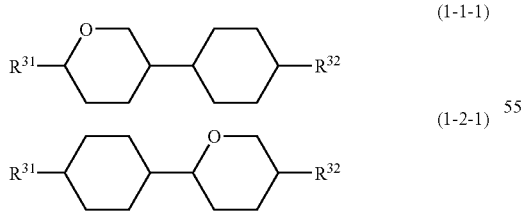

wherein $R^{31}$ and $R^{32}$ are independently alkyl having from 2 to 10 carbons, alkoxy having from 1 to 9 carbons or alkenyl having from 2 to 10 carbons; and one of $R^{31}$ and $R^{32}$ is alkyl.

9. A compound represented by any one of the following formulae (1-4-1), (1-5-1) and (1-6-1):

wherein $R^{31}$ and $R^{32}$ are independently alkyl having from 2 to 10 carbons, alkoxy having from 1 to 9 carbons or alkenyl having from 2 to 10 carbons; one of $R^{31}$ and $R^{32}$ is alkyl; $Z^{31}$ and $Z^{32}$ are independently a single bond, $—(CH_2)_2—$ or $—CH=CH—$; and one of $Z^{31}$ and $Z^{32}$ is a single bond.

10. The compound according to claim 8, wherein one of $R^{31}$ and $R^{32}$ is alkyl, and the other thereof is alkenyl.

11. The compound according to claim 9, wherein one of $R^{31}$ and $R^{32}$ is alkyl, and the other thereof is alkenyl.

12. The compound according to claim 8, wherein $R^{31}$ and $R^{32}$ each represent alkenyl.

13. The compound according to claim 9, wherein $R^{31}$ and $R^{32}$ each represent alkenyl.

14. A liquid crystal composition, comprising at least one compound represented by the formula (1) according to claim 1.

15. The liquid crystal composition according to claim 14, wherein the composition further comprises at least one compound selected from compounds represented by the following formulae (2), (3) and (4):

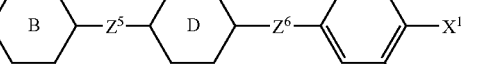

wherein $R^7$ is alkyl having from 1 to 10 carbons, provided that in the alkyl arbitrary $—CH_2—$ may be replaced by $—O—$ or $—CH=CH—$, and arbitrary hydrogen may be replaced by fluorine; $X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$; ring B and ring D are independently 1,4-cyclohexylene, 1,3-dioxane-2,5-diyl or 1,4-phenylene, provided that in the 1,4-phenylene arbitrary hydrogen may be replaced by fluorine; ring E is 1,4-cyclohexylene or 1,4-phenylene, provided that in the 1,4-phenylene arbitrary hydrogen may be replaced by fluorine; $Z^5$ and $Z^6$ are independently —$(CH_2)_2$—, —$(CH_2)_4$—, —COO—, —$CF_2O$—, —$OCF_2$—, —CH=CH— or a single bond; and $L^1$ and $L^2$ are independently hydrogen or fluorine.

16. The liquid crystal composition according to claim 14, wherein the composition further comprises at least one compound selected from compounds represented by the following formulae (5) and (6):

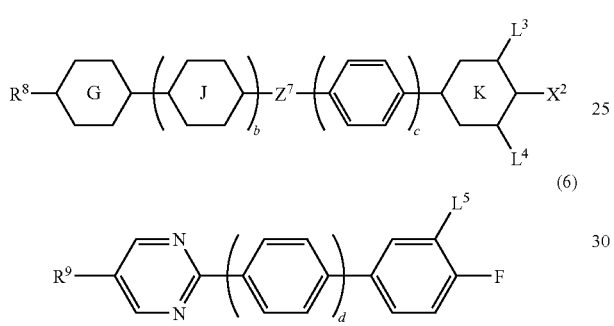

(5)

(6)

wherein $R^8$ and $R^9$ are independently alkyl having from 1 to 10 carbons, provided that in the alkyl arbitrary —$CH_2$— may be replaced by —O— or —CH=CH—, and arbitrary hydrogen may be replaced by fluorine; $X^2$ is —CH or —C≡C—CN; ring G is 1,4-cyclohexylene, 1,4-phenylene, 1,3-dioxane-2,5-diyl or pyrimidine-2,5-diyl; ring J is 1,4-cyclohexylene, pyrimidine-2,5-diyl or 1,4-phenylene, provided that in the 1,4-phenylene arbitrary hydrogen may be replaced by fluorine; ring K is 1,4-cyclohexylene or 1,4-phenylene; $Z^7$ is —$(CH_2)_2$—, —COO—, —$CF_2O$—, —$OCF_2$— or a single bond; $L^3$, $L^4$ and $L^5$ are independently hydrogen or fluorine; and b, c and d are independently 0 or 1.

17. The liquid crystal composition according to claim 14, wherein the composition further comprises at least one compound selected from compounds represented by the following formulae (7), (8), (9), (10) and (11):

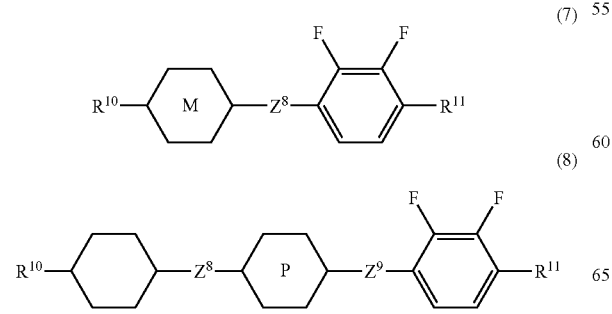

(7)

(8)

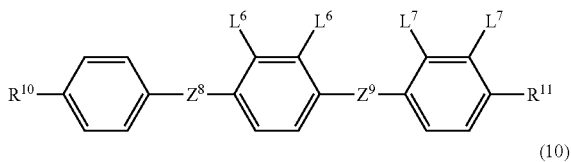

(9)

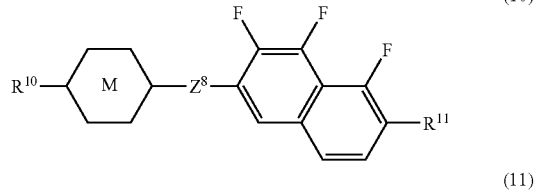

(10)

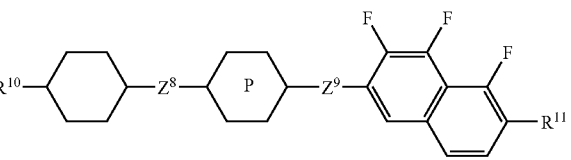

(11)

wherein $R^{10}$ and $R^{11}$ are independently alkyl having from 1 to 10 carbons, provided that in the alkyl arbitrary —$CH_2$— may be replaced by —O— or —CH=CH—, and arbitrary hydrogen may be replaced by fluorine, and $R^{10}$ may be fluorine; ring M and ring P are independently 1,4-cyclohexylene, 1,4-phenylene or decahydro-2,6-naphthylene; $Z^8$ and $Z^9$ are independently —$(CH_2)_2$—, —COO— or a single bond; $L^6$ and $L^7$ are independently hydrogen or fluorine; and at least one of $L^6$ and $L^7$ is fluorine.

18. The liquid crystal composition according to claim 14, wherein the composition further comprises at least one compound selected from compounds represented by the following formulae (12), (13) and (14):

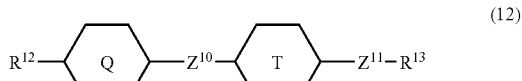

(12)

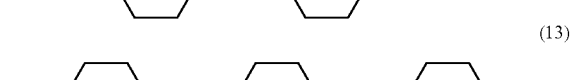

(13)

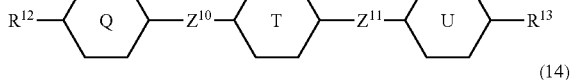

(14)

wherein $R^{12}$ and $R^{13}$ are independently alkyl having from 1 to 10 carbons, provided that in the alkyl arbitrary —$CH_2$— may be replaced by —O— or —CH=CH—, and arbitrary hydrogen may be replaced by fluorine; ring Q, ring T and ring U are independently 1,4-cyclohexylene, pyrimidine-2,5-diyl or 1,4-phenylene, provided that in the 1,4-phenylene arbitrary hydrogen may be replaced by fluorine; and $Z^{10}$ and $Z^{11}$ are independently —C≡C—, —COO—, —$(CH_2)_2$—, —CH=CH— or a single bond.

19. The liquid crystal composition according to claim 15, wherein the composition further comprises at least one compound selected from compounds represented by the following formulae (5) and (6):

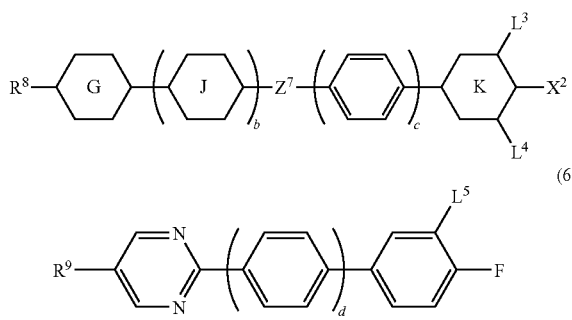

(5)

(6)

wherein $R^8$ and $R^9$ are independently alkyl having from 1 to 10 carbons, provided that in the alkyl arbitrary —$CH_2$— may be replaced by —O— or —CH=CH—, and arbitrary hydrogen may be replaced by fluorine; $X^2$ is —CH or —C≡C—CN; ring G is 1,4-cyclohexylene, 1,4-phenylene, 1,3-dioxane-2,5-diyl or pyrimidine-2,5-diyl; ring J is 1,4-cyclohexylene, pyrimidine-2,5-diyl or 1,4-phenylene, provided that in the 1,4-phenylene arbitrary hydrogen may be replaced by fluorine; ring K is 1,4-cyclohexylene or 1,4-phenylene; $Z^7$ is —$(CH_2)_2$—, —COO—, —$CF_2O$—, —$OCF_2$— or a single bond; $L^3$, $L^4$ and $L^5$ are independently hydrogen or fluorine; and b, c and d are independently 0 or 1.

20. The liquid crystal composition according to claim 15, wherein the composition further comprises at least one compound selected from compounds represented by the following formulae (12), (13) and (14):

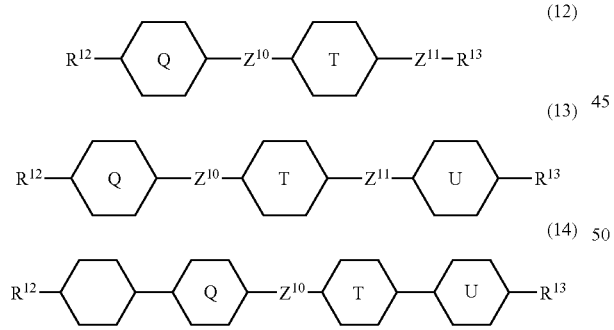

(12)

(13)

(14)

wherein $R^{12}$ and $R^{13}$ are independently alkyl having from 1 to 10 carbons, provided that in the alkyl arbitrary —$CH_2$— may be replaced by —O— or —CH=CH—, and arbitrary hydrogen may be replaced by fluorine; ring Q, ring T and ring U are independently 1,4-cyclohexylene, pyrimidine-2,5-diyl or 1,4-phenylene, provided that in the 1,4-phenylene arbitrary hydrogen may be replaced by fluorine; and $Z^{10}$ and $Z^{11}$ are independently —C≡C—, —COO—, —$(CH_2)_2$—, —CH=CH— or a single bond.

21. The liquid crystal composition according to claim 16, wherein the composition further comprises at least one compound selected from compounds represented by the following formulae (12), (13) and (14):

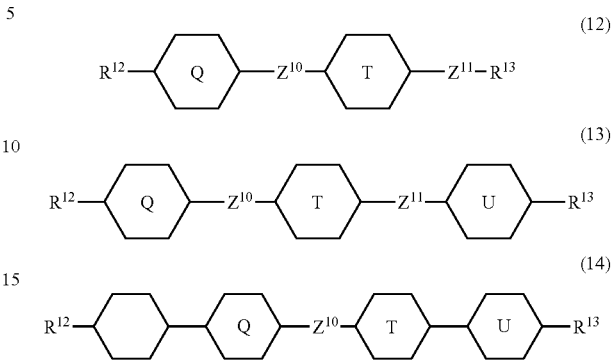

(12)

(13)

(14)

wherein $R^{12}$ and $R^{13}$ are independently alkyl having from 1 to 10 carbons, provided that in the alkyl arbitrary —$CH_2$— may be replaced by —O— or —CH=CH—, and arbitrary hydrogen may be replaced by fluorine; ring Q, ring T and ring U are independently 1,4-cyclohexylene, pyrimidine-2,5-diyl or 1,4-phenylene, provided that in the 1,4-phenylene arbitrary hydrogen may be replaced by fluorine; and $Z^{10}$ and $Z^{11}$ are independently —C≡C—, —COO—, —$(CH_2)_2$—, —CH=CH— or a single bond.

22. The liquid crystal composition according to claim 17, wherein the composition further comprises at least one compound selected from compounds represented by the following formulae (12), (13) and (14):

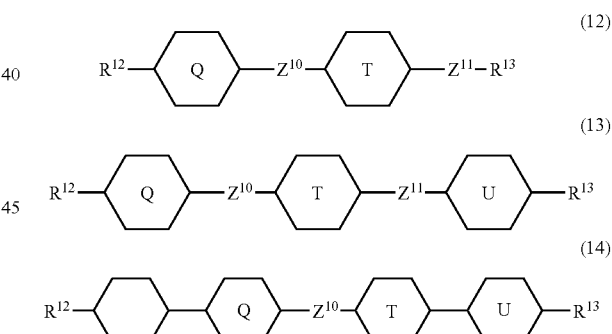

(12)

(13)

(14)

wherein $R^{12}$ and $R^{13}$ are independently alkyl having from 1 to 10 carbons, provided that in the alkyl arbitrary —$CH_2$— may be replaced by —O— or —CH=CH—, and arbitrary hydrogen may be replaced by fluorine; ring Q, ring T and ring U are independently 1,4-cyclohexylene, pyrimidine-2,5-diyl or 1,4-phenylene, provided that in the 1,4-phenylene arbitrary hydrogen may be replaced by fluorine; and $Z^{10}$ and $Z^{11}$ are independently —C≡C—, —COO—, —$(CH_2)_2$—, —CH=CH— or a single bond.

23. The liquid crystal composition according to claim 14, wherein the composition further comprises at least one optically active compound.

24. The liquid crystal composition according to claim 14, wherein the composition comprises the at least one compound represented by the formula (1) in an amount of from approximately 5% to approximately 90% by weight based on the total weight of the liquid crystal composition.

25. A liquid crystal display device comprising the liquid crystal composition according to claim 14.

26. The liquid crystal display device according to claim 25, wherein the display device is driven by active matrix based on a VA or ECB effect.

\* \* \* \* \*